United States Patent [19]

Kojima et al.

[11] Patent Number: 5,302,621
[45] Date of Patent: Apr. 12, 1994

[54] AZASTEROID COMPOUNDS FOR THE TREATMENT OF PROSTATIC HYPERTROPHY, THEIR PREPARATION AND USE

[75] Inventors: Koichi Kojima; Hitoshi Kurata; Hiroyoshi Horikoshi; Takakazu Hamada, all of Tokyo, Japan

[73] Assignee: Sankyo Company, Limited, Tokyo, Japan

[21] Appl. No.: 23,871

[22] Filed: Feb. 26, 1993

Related U.S. Application Data

[63] Continuation of Ser. No. 781,982, Oct. 24, 1991, abandoned.

Foreign Application Priority Data

Oct. 29, 1990 [JP] Japan ............................... 2-291401

[51] Int. Cl.$^5$ .................... A61K 31/58; C07J 73/00
[52] U.S. Cl. .................... 514/284; 514/253; 514/256; 544/238; 544/295; 544/296; 544/333; 544/335; 544/336; 544/405; 546/77
[58] Field of Search ................ 546/77; 544/238, 295, 544/296, 333, 335, 336, 405; 514/253, 256, 284

[56] References Cited

U.S. PATENT DOCUMENTS

| | | | |
|---|---|---|---|
| 4,179,453 | 12/1979 | Johnston | 260/397.1 |
| 4,220,775 | 9/1980 | Rasmusson | 552/519 |
| 4,377,584 | 3/1983 | Rasmusson | 540/576 |
| 4,732,897 | 3/1988 | Cainelli et al. | 546/77 |
| 4,760,071 | 7/1988 | Rasmusson | 546/77 |
| 5,021,575 | 6/1991 | King | 546/77 |

FOREIGN PATENT DOCUMENTS

| | | |
|---|---|---|
| 0004949 | 10/1979 | European Pat. Off. |
| 0155096 | 9/1985 | European Pat. Off. |
| 63-65080 | 11/1985 | Japan |

OTHER PUBLICATIONS

Padilla, *The Prostate* 6, 129–143 (1985).
Petrow *The Prostate*, 6, 169–182 (1985).
Rasmusson et al, "Azasteroids: Structure–Activity Relationships for Inhibition of 5α-Reductase and of Androgen Receptor Binding", 1986, vol. 29, pp. 2298–2315, Journal of Medicinal Chemistry.

*Primary Examiner*—Mark L. Berch
*Attorney, Agent, or Firm*—Frishauf, Holtz, Goodman & Woodward

[57] ABSTRACT

Compounds of formula (I):

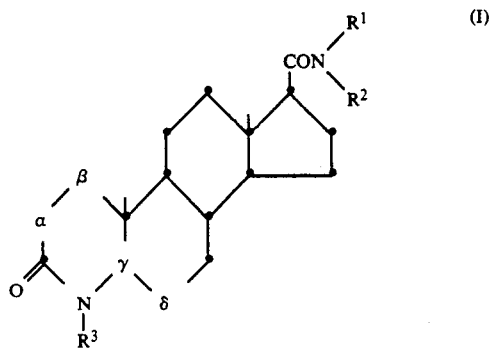

(in which: $R^1$ is a hydrogen atom, an unsubstituted alkyl group, an aryl-substituted alkyl group or a heterocyclic-substituted alkyl group; $R^2$ is an aryl-substituted alkyl group, a heterocyclic-substituted alkyl group or a diarylamino group; $R^3$ is a hydrogen atom, an unsubstituted alkyl group, an aryl-substituted alkyl group or an alkenyl group having from 3 to 6 carbon atoms; and each of the bonds represented by α-β and γ-δ is a carbon-carbon single bond or a carbon-carbon double bond;) and pharmaceutically acceptable salts and esters thereof are useful for the treatment and prophylaxis of prostatic hypertrophy. We also provide processes for their preparation.

101 Claims, No Drawings

AZASTEROID COMPOUNDS FOR THE TREATMENT OF PROSTATIC HYPERTROPHY, THEIR PREPARATION AND USE

This application is a continuation of application Ser. No. 07/781,982, filed Oct. 24, 1991, abandoned.

BACKGROUND TO THE INVENTION

The present invention relates to a series of new azasteroid compounds which are useful for the treatment and prophylaxis of prostatic hypertrophy, and provides methods and compositions using them as well as processes for their preparation.

Available treatment for prostatic hypertrophy is very limited, although it has been shown that compounds which inhibit the activity of testosterone 5α-reductase may be useful for the treatment and prophylaxis of prostatic hypertrophy, and U.S. Pat. No. 4,179,453 and 4,760,071 disclose several compounds which have this type of activity and which may thus be useful for this purpose. Of these compounds, those which are the most active and are believed to be closest to the compounds of the present invention are the compounds of formula (A):

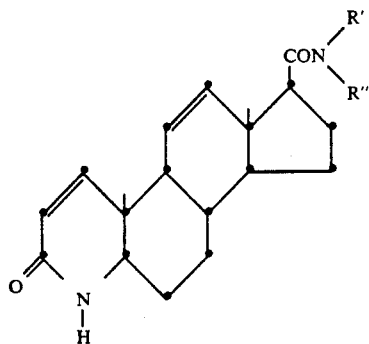

in which R' and R" both represent ethyl groups (Compound A₁), or R' represents a hydrogen atom and R" represents a t-butyl group (Compound A₂). However, whilst these compounds do have quite a potent activity, there is a need to develop compounds having greater activity.

We have now discovered that compounds having certain specific carbamoyl substituents at the 17-position of the azasteroid skeleton have excellent 5α-reductase inhibitory activity, and can therefore be used for the type of treatment and prophylaxis referred to above.

BRIEF SUMMARY OF INVENTION

It is therefore an object of the present invention to provide a series of new azasteroid compounds which may be useful for the treatment and prophylaxis of prostatic hypertrophy.

It is a further and more specific object of the present invention to provide a series of new azasteroid compounds having improved activity for the treatment and prophylaxis of prostatic hypertrophy.

The compounds of the present invention are those azasteroid compounds which have the formula (I):

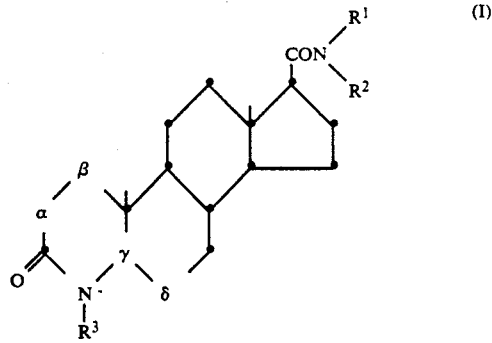

in which:

$R^1$ represents a hydrogen atom, an unsubstituted alkyl group having from 1 to 6 carbon atoms or a substituted alkyl group having from 1 to 6 carbon atoms which is substituted by at least one substituent selected from the group consisting of aryl groups as defined below, aromatic heterocyclic groups as defined below, carboxy groups and hydroxy groups;

$R^2$ represents a substituted alkyl group having from 1 to 6 carbon atoms which is substituted by at least one substituent selected from the group consisting of aryl groups as defined below and aromatic heterocyclic groups as defined below, and which is otherwise unsubstituted or is substituted by at least one additional substituent selected from the group consisting of carboxy groups and hydroxy groups, or a diarylamino group;

$R^3$ represents a hydrogen atom, an unsubstituted alkyl group having from 1 to 6 carbon atoms, a substituted alkyl group having from 1 to 6 carbon atoms which is substituted by at least one substituent selected from the group consisting of aryl groups as defined below, carboxy groups and hydroxy groups, or an alkenyl group having from 3 to 6 carbon atoms;

each of the bonds represented by α-β and γ-δ is a carbon-carbon single bond (—CH₂—CH₂—) or a carbon-carbon double bond (—CH=CH—);

said aryl groups are carbocyclic aryl groups which have from 6 to 10 ring carbon atoms and which are unsubstituted or are substituted by at least one substituent selected from the group consisting of alkyl groups having from 1 to 6 carbon atoms, alkoxy groups having from 1 to 6 carbon atoms, alkoxycarbonyl groups having from 2 to 7 carbon atoms, hydroxy groups, halogen atoms and groups of formula —NHR$^a$, where R$^a$ represents an aliphatic carboxylic acyl group having from 1 to 5 carbon atoms;

said aromatic heterocyclic groups have 5 or 6 ring atoms of which from 1 to 3 are hetero-atoms selected from the group consisting of nitrogen, oxygen and sulfur hetero-atoms and are unsubstituted or are substituted by at least one substituent selected from the group consisting of alkyl groups having from 1 to 6 carbon atoms, alkoxy groups having from 1 to 6 carbon atoms and halogen atoms;

and pharmaceutically acceptable salts and esters thereof.

The invention also provides a composition for the treatment or prophylaxis of prostatic hypertrophy, which comprises an effective amount of at least one active compound in admixture with a carrier or diluent, wherein the active compound is at least one compound of formula (I) or a pharmaceutically acceptable salt or ester thereof.

The invention still further provides a method of treating prostatic hypertrophy, which comprises administering to an animal, preferably a mammal, which may be human, at least one active compound, wherein the active compound is at least one compound of formula (I) or a pharmaceutically acceptable salt or ester thereof.

The invention also provides processes for preparing the compounds of the present invention which are described in greater detail hereafter.

DETAILED DESCRIPTION OF INVENTION

In the compounds of formula (I), where $R^1$ represents an alkyl group having from 1 to 6 carbon atoms, this may be a straight or branched chain group having from 1 to 6 carbon atoms, and examples include the methyl, ethyl, propyl, isopropyl, butyl, isobutyl, sec-butyl, t-butyl, pentyl, isopentyl, neopentyl, hexyl and isohexyl groups. Of these, we prefer those alkyl groups having from 1 to 4 carbon atoms, preferably the methyl, ethyl, propyl, isopropyl, butyl and isobutyl groups, more preferably the methyl and ethyl groups, and most preferably the methyl group. The alkyl group may be unsubstituted or it may be substituted by at least one substituent, preferably one or two substituents, selected from the group consisting of aryl groups as defined above and exemplified below, aromatic heterocyclic groups as defined above and exemplified below, carboxy groups and hydroxy groups.

Examples of such aryl groups include the phenyl and naphthyl (1- or 2-naphthyl) groups which may be unsubstituted or substituted by one or more of the following groups, preferably from 1 to 3 groups, and more preferably one or two groups:

alkyl groups having from 1 to 6 carbon atoms, for example the methyl, ethyl, propyl, isopropyl, butyl, isobutyl, sec-butyl, t-butyl, pentyl, isopentyl, neopentyl, hexyl and isohexyl groups, of which the methyl and ethyl groups are preferred and the methyl group is most preferred;

alkoxy groups having from 1 to 6 carbon atoms, for example the methoxy, ethoxy, propoxy, isopropoxy, butoxy, isobutoxy, sec-butoxy, t-butoxy, pentyloxy, isopentyloxy, neopentyloxy, hexyloxy and isohexyloxy groups, of which the methoxy and ethoxy groups are preferred and the methoxy group is most preferred;

halogen atoms, for example the fluorine, chlorine, bromine or iodine atoms, of which the fluorine and chlorine atoms are preferred;

alkoxycarbonyl groups, having from 2 to 7, preferably from 2 to 5, carbon atoms (i.e. the alkoxy part itself contains from 1 to 6, preferably from 1 to 4 carbon atoms), for example the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, hexyloxycarbonyl and isohexyloxycarbonyl groups, of which the methoxycarbonyl and ethoxycarbonyl groups are preferred; groups of formula —$NHR^a$, where $R^a$ represents an aliphatic carboxylic acyl group having from 1 to 5 carbon atoms, for example the formyl, acetyl, propionyl, butyryl, valeryl, isovaleryl and pivaloyl groups, of which the formyl and acetyl groups are preferred; and hydroxy groups.

Examples of the substituted and unsubstituted aryl groups include the phenyl, 1-naphthyl, 2-naphthyl, 2-, 3- and 4-tolyl, 2-, 3- and 4-methoxyphenyl, 2-, 3- and 4-ethylphenyl, 2-, 3- and 4-ethoxyphenyl, 2-, 3- and 4-chlorophenyl, 2-, 3- and 4-fluorophenyl, 2-, 3- and 4-hydroxyphenyl, 2-, 3- and 4-acetamidophenyl and 2-, 3- and 4-formamidophenyl groups.

Where the substituent on $R^1$ is a heterocyclic group, this has 5 or 6 ring atoms, of which from 1 to 3 are hetero-atoms selected from the group consisting of nitrogen, oxygen and sulfur hetero-atoms. The heterocyclic group may be unsubstituted or it may be substituted by at least one substituent selected from the group consisting of alkyl groups having from 1 to 6 carbon atoms, alkoxy groups having from 1 to 6 carbon atoms and halogen atoms, all of which are as exemplified above. Where there are 3 hetero-atoms, we prefer that at least one (more preferably 2) should be a nitrogen atom and one or two should be nitrogen, oxygen or sulfur atoms (and, where there are two, they may be the same or different). Where there are two hetero-atoms, these may be the same or different and they are selected from nitrogen, oxygen and sulfur atoms; however, more preferably one is a nitrogen atom or an oxygen atom and the other is a nitrogen, oxygen or sulfur atom. Such groups may be unsubstituted or they may be substituted by at least one (preferably from 1 to 3) of the substituents defined above. Examples of such unsubstituted groups include the furyl (2- or 3-), thienyl (2- or 3-), pyridyl (2-, 3- or 4-), pyrrolyl (2-or 3-), imidazolyl (2-, 4- or 5-), thiazolyl (2-, 4- or 5-), isothiazolyl (3-, 4- or 5-), oxazolyl (2-, 4- or 5-), isoxazolyl (3-, 4- or 5-), pyrazinyl (2- or 3-), pyrimidinyl (2-, 4-, 5- or 6-) and pyridazinyl (3-, 4-, 5- or 6-) groups, of which we prefer the furyl and thienyl groups and especially the thienyl group.

Where $R^2$ represents a substituted alkyl group, the alkyl part may be any of those alkyl groups exemplified above in relation to $R^1$, and the group is necessarily substituted by at least one, preferably from 1 to 5 (depending upon the availability of substitutable positions), more preferably from 1 to 3 and most preferably 1 or 2, substituents; these must include at least one substituent selected from the group consisting of aryl groups and aromatic heterocyclic groups, both of which may be as exemplified above in relation to the substituents on the groups represented by $R^1$, and may optionally contain in addition a carboxy or hydroxy substituent.

Where $R^2$ represents a diarylamino group, the two aryl moieties may the same or different, and they may be as exemplified above in relation to the aryl substituents on $R^1$. Preferred such groups are the diphenylamino groups.

$R^3$ may represents a hydrogen atom, an unsubstituted alkyl group having from 1 to 6 carbon atoms, a substituted alkyl group having from 1 to 6 carbon atoms which is substituted by at least one aryl group, carboxy group or hydroxy group, in which case, these may all be as exemplified above in relation to the similar groups which may be represented by $R^1$.

Alternatively, it may represent an alkenyl group. Where $R^3$ represents an alkenyl group, this has from 3 to 6 carbon atoms and may be a straight or branched chain group. Examples of such groups include the allyl, methallyl, 2-butenyl, 2-pentenyl or 2-hexenyl; of these we prefer those alkenyl groups having 3 or 4 carbon atoms, and especially the allyl group.

Preferably the bond represented by $\alpha$-$\beta$ is a carbon-carbon single bond and the bond represented by $\gamma$-$\delta$ is a carbon-carbon single bond or a carbon-carbon double bond, or the bond represented by $\alpha$-$\beta$ is a carbon-carbon double bond and the bond represented by γ-δ is a carbon-carbon single bond.

Examples of preferred groups which may be represented by

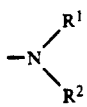

include the following groups:
benzylamino,
(2-, 3- or 4-methylbenzyl)amino,
(2-, 3- or 4-methoxybenzyl)amino,
(2-, 3- or 4-fluorobenzyl)amino,
(2-, 3- or 4-chlorobenzyl)amino,
phenethylamino,
(2-, 3- or 4-methylphenethyl)amino,
(2-, 3- or 4-methoxyphenethyl)amino,
(2-, 3- or 4-fluorophenethyl)amino,
(2-, 3- or 4-chlorophenethyl)amino,
(3-phenylpropyl)amino,
(1-methyl-1-phenylethyl)amino,
[1-methyl-1-(2-, 3- or 4-methylphenyl)ethyl]amino,
[1-methyl-1-(2-, 3- or 4-methoxyphenyl)ethyl]amino,
[1-methyl-1-(2-, 3- or 4-chlorophenyl)ethyl]amino,
[1-methyl-1-(2-, 3- or 4-fluorophenyl)ethyl]amino,
[1-methyl-1-(2-, 3- or 4-hydroxyphenyl)ethyl]amino,
[1-methyl-1-(2-, 3- or 4-acetamidophenyl)ethyl]amino,
[1-methyl-1-(2,3-, 2,4-, 2,5-, 2,6-, 3,4-, 3,5- or 3,6-dimethoxyphenyl)ethyl]amino,
(1,1-dimethyl-2-phenylethyl)amino,
[1,1-dimethyl-2-(2-, 3- or 4-methylphenyl)ethyl]amino,
[1,1-dimethyl-2-(2-, 3- or 4-methoxyphenyl)ethyl]amino,
[1,1-dimethyl-2-(2-, 3- or 4-chlorophenyl)ethyl]amino,
[1,1-dimethyl-2-(2-, 3- or 4-fluorophenyl)ethyl]amino,
benzhydrylamino,
[(2-, 3- or 4-), (2'-, 3'-, or 4'-)-difluorobenzhydryl]amino,
[(2-, 3- or 4-), (2'-, 3'- or 4'-)-dimethoxybenzhydryl]amino,
(2-, 3- or 4-chlorobenzhydryl)amino,
(2-, 3- or 4-methoxybenzhydryl)amino,
(2-, 3- or 4-fluorobenzhydryl)amino,
(2-, 3- or 4-methylbenzhydryl)amino,
(2-, 3- or 4-hydroxybenzhydryl)amino,
[(2-, 3- or 4-),(2'-, 3'- or 4'-)-dihydroxybenzhydryl]amino,
[(2-, 3- or 4-),(2'-, 3'- or 4'-)-dimethylbenzhydryl]amino,
(1,1-diphenylethyl)amino,
(1,2-diphenylethyl)amino,
[2-(2-, 3- or 4-chlorophenyl)-1-phenylethyl]amino,
[1-(2-, 3- or 4-chlorophenyl)-2-(2-, 3- or 4-chlorophenyl)ethyl]amino,
[2-(2-, 3- or 4-fluorophenyl)-1-phenylethyl]amino,
[2-(2-, 3- or 4-methylphenyl)-1-phenylethyl]amino,
[2-(2-, 3- or 4-methoxyphenyl)-1-phenylethyl]amino,
[1-(2-, 3- or 4-fluorophenyl)-2-(2-, 3- or 4-fluorophenyl)ethyl]amino,
[1-(2-, 3- or 4-chlorophenyl)-2-(2-, 3- or 4-methoxyphenyl)ethyl]amino,
[1-(2-, 3- or 4-methylphenyl)-2-(2-, 3- or 4-methylphenyl)ethyl]amino,
[1-(2-, 3- or 4-hydroxyphenyl)-2-(2-, 3- or 4-hydroxyphenyl)ethyl]amino,
[2-(2-, 3- or 4-fluorophenyl)-1-(2-, 3- or 4-methylphenyl)ethyl]amino,
[2-(2-, 3- or 4-fluorophenyl)-1-(2-, 3- or 4-methoxyphenyl)ethyl]amino,
[2-(2-, 3- or 4-hydroxyphenyl)-1-phenylethyl]amino,
[1-(2-, 3- or 4-methoxyphenyl)-2-phenylethyl]amino,
(1-methyl-1,2-diphenylethyl)amino,
(2,2-diphenylethyl)amino,
[2-(2-, 3- or 4-methoxyphenyl)-2-(2-, 3- or 4-methoxyphenyl)ethyl]amino,
[2-(2-, 3- or 4-methylphenyl)-2-(2-, 3- or 4-methylphenyl)ethyl]amino,
(1-benzyl-4-phenylbutyl)amino,
(1,1-diphenylethyl)amino,
[1-(2-, 3- or 4-fluorophenyl)-1-(2-, 3- or 4-fluorophenyl)ethyl]amino,
[1-(2-, 3- or 4-methylphenyl)-1-(2-, 3- or 4-methylphenyl)ethyl]amino,
[1-(2-, 3- or 4-methoxyphenyl)-1-(2-, 3- or 4-methoxyphenyl)ethyl]amino,
[1-(2-, 3- or 4-hydroxyphenyl)-1-phenylethyl]amino,
tritylamino,
(2-, 3- or 4-),(2'-, 3'- or 4'-),(2''-, 3''- or 4''-)-trifluorotritylamino,
(2-, 3- or 4-),(2'-, 3'- or 4'-),(2''-, 3''- or 4''-)-trimethyltritylamino,
(1-benzyl-2-phenylethyl)amino,
[1-(2-, 3- or 4-fluorobenzyl)-2-(2-, 3- or 4-fluorophenyl)ethyl]amino,
(1-benzyl-1-methyl-2-phenylethyl)amino,
[1-(2-, 3- or 4-chlorobenzyl)-2-(2-, 3- or 4-chlorophenyl)ethyl]amino,
[1-(2-, 3- or 4-fluorobenzyl)-2-(2,-3- or 4-fluorophenyl)-1-methylethyl]amino,
[1-methyl-2-(2-, 3- or 4-methylphenyl)-3-(2-, 3- or 4-methylphenyl)propyl]amino,
[2-(2-, 3- or 4-fluorophenyl)-3-(2-, 3- or 4-fluorophenyl)-1-methylpropyl]amino,
(1,3-diphenylpropyl)amino,
[1-(2-, 3- or 4-methylphenyl)-3-(2, 3- or 4-methylphenyl)propyl]amino,
[1-(2-, 3- or 4-methoxyphenyl)-3-(2-, 3- or 4-methoxyphenyl)propyl]amino,
(1,4-diphenylbutyl)amino,
[1-(2-, 3- or 4-chlorophenyl)-4-(2-, 3- or 4-chlorophenyl)butyl]amino,
[1-(2-, 3- or 4-methoxyphenyl)-4-(2-, 3- or 4-methoxyphenyl)butyl]amino,
(1-methyl-3,3-diphenylpropyl)amino,
[3-(2-, 3- or 4-fluorophenyl)-3-(2-, 3- or 4-fluorophenyl)-1-methylpropyl]amino,
[1-methyl-3-(2-, 3- or 4-methylphenyl)-3-(2-, 3- or 4-methylphenyl)propyl]amino,
N-benzyl-N-methylamino,
N-benzyl-N-ethylamino,
N-benzyl-N-isopropylamino,
N-benzyl-N-isobutylamino,
N-benzyl-N-t-butylamino,
N-(2-, 3- or 4-fluorobenzyl)-N-isopropylamino,
N-(2-, 3- or 4-chlorobenzyl)-N-isopropylamino,
N-(2-, 3- or 4-methylbenzyl)-N-isopropylamino,
N-(2-, 3- or 4-methoxybenzyl)-N-isopropylamino,
N-(2-, 3- or 4-hydroxybenzyl)-N-isopropylamino,
N,N-dibenzylamino,
N-benzyl-N-(2-, 3- or 4-methoxybenzyl)amino,
N-(2-, 3- or 4-fluorobenzyl)-N-(2-, 3-or 4-fluorobenzyl)amino,
N-(2-, 3- or 4-methylbenzyl)-N-(2-, 3- or 4-methylbenzyl)amino, N-(2-, 3- or 4-methoxybenzyl)-N-(2-, 3- or 4-methoxybenzyl)amino,
N-(2-, 3- or 4-hydroxybenzyl)-N-(2-, 3- or 4-hydroxybenzyl)amino,
N-benzyl-N-phenethylamino,
N-benzyl-N-(1-phenylethyl)amino,
N-benzyl-N-(1-methyl-1-phenylethyl)amino,
N,N-diphenethylamino,
N,N-bis(1-phenylethyl)amino,
N-benzyl-N-(3-phenylpropyl)amino,
(2- or 3-furylmethyl)amino,
(2- or 3-thienylmethyl)amino,
(2-, 3- or 4-pyridylmethyl)amino,
(2- or 3-methyl-2- or 3-furylmethyl)amino,
(2- or 3-methyl-2- or 3-thienylmethyl)amino,
[2-(2- or 3-furyl)ethyl]amino,
[2-(2- or 3-thienyl)ethyl]amino,
[3-(2- or 3-furyl)propyl]amino,
[3-(2- or 3-thienyl)propyl]amino,
[bis(2- or 3-furyl)methyl]amino,
[bis(2- or 3-thienyl)methyl]amino,
[1,1-bis(2- or 3-furyl)ethyl]amino,
[1,1-bis(2- or 3-thienyl)ethyl]amino,
[(2- or 3-methyl-2- or 3-furyl),(2- or 3-methyl-2- or 3-furyl)methyl]amino,
[(2- or 3-methyl-2- or 3-thienyl),(2- or 3-methyl-2- or 3-thienyl)methyl]amino,
[1-(2- or 3-furyl)-1-methylethyl]amino,
[1-(2- or 3-thienyl)-1-methylethyl]amino,
[1-(2- or 5-methyl-2- or 3-thienyl)-1-methylethyl]amino,
[1-(2- or 5-methyl-2- or 3-furyl)-1-methylethyl]amino,
[1-(2- or 3-furyl)-2-(2- or 3-furyl)ethyl]amino,
[1-(2- or 3-thienyl)-2-(2- or 3-thienyl)ethyl]amino,
[1-(2- or 3-furyl)-2-phenylethyl]amino,
[1-(2- or 3-furyl)-2-(2-, 3- or 4-methylphenyl)ethyl]amino,
[2-phenyl-1-(2- or 3-thienyl)ethyl]amino,
[1-phenyl-2-(2- or 3-thienyl)ethyl]amino,
[2-(2-, 3- or 4-methylphenyl)-1-(2- or 3-thienyl)ethyl]amino,
[2-(2-, 3- or 4-chlorophenyl)-1-(2- or 3-thienyl)ethyl]amino,
[2-(2-, 3- or 4-fluorophenyl)-1-(2- or 3-thienyl)ethyl]amino,
[2-(2-, 3- or 4-methoxyphenyl)-1-(2- or 3-thienyl)ethyl]amino,
N-(2- or 3-furylmethyl)-N-(2- or 3-furylmethyl)amino,
N-(2- or 3-thienylmethyl)-N-(2- or 3-thienylmethyl)amino,
[1-(2-, 3- or 4-fluorophenyl)-2-(2- or 3-thienyl)ethyl]amino,
N-benzyl-N-(2- or 3-furylmethyl)amino,
N-benzyl-N-(2- or 3-thienylmethyl)amino,
(2-hydroxy-1,2-diphenylethyl)amino,
N,N-diphenylhydrazino,
N-(2-, 3- or 4-methylphenyl)-N-phenylhydrazino,
N-(2-, 3- or 4-methoxyphenyl)-N-phenylhydrazino,
N-(2-, 3- or 4-chlorophenyl)-N-phenylhydrazino,
N-(2-, 3- or 4-fluorophenyl)-N-phenylhydrazino,
N-(2-, 3- or 4-hydroxyphenyl)-N-phenylhydrazino,
N-(2-, 3- or 4-acetamidophenyl)-N-phenylhydrazino,
N-(2-, 3- or 4-methylphenyl)-N-(2-, 3- or 4-methylphenyl)hydrazino, and
N-(2-, 3- or 4-methoxyphenyl)-N-(2-, 3- or 4-methoxyphenyl)hydrazino.

More preferred such groups include the following groups:
(1-methyl-1-phenylethyl)amino,
[1-methyl-1-(2-, 3- or 4-methylphenyl)ethyl]amino,
[1-methyl-1-(2-, 3- or 4-methoxyphenyl)ethyl]amino,
[1-methyl-1-(2-, 3- or 4-chlorophenyl)ethyl]amino,
[1-methyl-1-(2-, 3- or 4-fluorophenyl)ethyl]amino,
[1-methyl-1-(2-, 3- or 4-hydroxyphenyl)ethyl]amino,
[1-methyl-1-(2-, 3- or 4-acetamidophenyl)ethyl]amino,
[1-methyl-1-(2,3-, 2,4-, 2,5-, 2,6-, 3,4-, 3,5- or 3,6-dimethoxyphenyl)ethyl]amino,
(1,1-dimethyl-2-phenylethyl)amino,
benzhydrylamino,
[(2-, 3- or 4-),(2'-, 3'- or 4'-)-difluorobenzhydryl]amino,
[(2-, 3- or 4-),(2'-, 3'- or 4'-)-dimethoxybenzhydryl]amino,
(2-, 3- or 4-chlorobenzhydryl)amino,
(2-, 3- 4-methoxybenzhydryl)amino,
(2-, 3- or 4-fluorobenzhydryl)amino,
(2-, 3- or 4-methylbenzhydryl)amino,
(2-, 3- or 4-hydroxybenzhydryl)amino,
[(2-, 3- or 4-),(2'-, 3'- or 4'-)-dihydroxybenzhydryl]amino,
[(2-, 3- or 4-),(2'-, 3'- or 4'-)-dimethylbenzhydryl]amino,
(1,1-diphenylethyl)amino,
(1,2-diphenylethyl)amino,
[2-(2-, 3- or 4-chlorophenyl)-1-phenylethyl]amino,
[1-(2-, 3- or 4-chlorophenyl)-2-(2-, 3- or 4-chlorophenyl)ethyl]amino,
[2-(2-, 3- or 4-fluorophenyl)-1-phenylethyl]amino,
[2-(2-, 3- or 4-methylphenyl)-1-phenylethyl]amino,
[2-(2-, 3- or 4-methoxyphenyl)-1-phenylethyl]amino,
[1-(2-, 3- or 4-fluorophenyl)-2-(2-, 3- or 4-fluorophenyl)ethyl]amino,
[1-(2-, 3- or 4-chlorophenyl)-2-(2-, 3- or 4-methoxyphenyl)ethyl]amino,
[1-(2-, 3- or 4-methylphenyl)-2-(2-, 3- or 4-methylphenyl)ethyl]amino,
[1-(2-, 3- or 4-hydroxyphenyl)-2-, 3- or 4-hydroxyphenyl)ethyl]amino,
[2-(2-, 3- or 4-fluorophenyl)-1-(2-, 3- or 4-methylphenyl)ethyl]amino,
[2-(2-, 3- or 4-fluorophenyl)-1-(2-, 3- or 4-methoxyphenyl)ethyl]amino,
[2-(2-, 3- or 4-hydroxyphenyl)-1-phenylethyl]amino,
[1-(2-, 3- or 4-methoxyphenyl)-2-phenylethyl]amino,
(1-methyl-1,2-diphenylethyl)amino,
(2,2-diphenylethyl)amino,
(1,1-diphenylethyl)amino,
[1-(2-, 3- or 4-fluorophenyl)-1-(2-, 3- or 4-fluorophenyl)ethyl]amino,
[1-(2-, 3- or 4-methylphenyl)-1-(2-, 3- or 4-methylphenyl)ethyl]amino,
[1-(2-, 3- or 4-methoxyphenyl)-1-(2-, 3- or 4-methoxyphenyl)ethyl]amino,
[1-(2-, 3- or 4-hydroxyphenyl)-1-phenylethyl]amino,
tritylamino,
(1-benzyl-2-phenylethyl)amino,
(1-benzyl-1-methyl-2-phenylethyl)amino,
N-benzyl-N-methylamino,
N-benzyl-N-ethylamino,
N-benzyl-N-isopropylamino,
N-benzyl-N-isobutylamino,
N-benzyl-N-t-butylamino,
N-(2-, 3- or 4-fluorobenzyl)-N-isopropylamino,
N-(2-, 3- or 4-chlorobenzyl)-N-isopropylamino,
N-(2-, 3- or 4-methylbenzyl)-N-isopropylamino,
N-(2-, 3- or 4-methoxybenzyl)-N-isopropylamino,
N-(2-, 3- or 4-hydroxybenzyl)-N-isopropylamino,
N-benzyl-N-(2-, 3- or 4-methoxybenzyl)amino,
N,N-dibenzylamino, N-(2-, 3- or 4-fluorobenzyl)-N-(2-, 3- or 4-fluorobenzyl)amino,
N-(2-, 3- or 4-methylbenzyl)-N-(2-, 3- or 4-methylbenzyl)amino,
N-(2-, 3- or 4-methoxybenzyl)-N-(2-, 3- or 4-methoxybenzyl)amino,
N-(2-, 3- or 4-hydroxybenzyl)-N-(2-, 3- or 4-hydroxybenzyl)amino,
[bis(2- or 3-furyl)methyl]amino,
[bis(2- or 3-thienyl)methyl]amino,
[1,1-bis(2- or 3-thienyl)ethyl]amino,
[(2- or 3-methyl-2- or 3-thienyl), (2- or 3-methyl-2- or 3-thienyl)methyl]amino,
[1-(2- or 3-thienyl)-1-methylethyl]amino,
[1-(2- or 3-furyl)-1-methylethyl]amino,
[1-(2- or 5-methyl-2- or 3-thienyl)-1-methylethyl]amino,
[1-(2- or 3-furyl)-2-(2- or 3-furyl)ethyl]amino,
[1-(2- or 3-thienyl)-2-(2- or 3-thienyl)ethyl]amino,
[1-(2- or 3-furyl)-2-phenylethyl]amino,
[2-phenyl-1-(2- or 3-thienyl)ethyl]amino,
[1-phenyl-2-(2- or 3-thienyl)ethyl]amino,
[2-(2-, 3- or 4-methylphenyl)-1-(2- or 3-thienyl)ethyl]amino,
[2-(2-, 3- or 4-chlorophenyl)-1-(2- or 3-thienyl)ethyl]amino,
[2-(2-, 3- or 4-fluorophenyl)-1-(2- or 3-thienyl)ethyl]amino,
[2-(2-, 3- or 4-methoxyphenyl)-1-(2- or 3-thienyl)ethyl]amino,
N-(2- or 3-thienylmethyl)-N-(2- or 3-thienylmethyl)amino,
[1-(2-, 3- or 4-fluorophenyl)-2-(2- or 3-thienyl)ethyl]amino,
(2-hydroxy-1,2-diphenylethyl)amino,
N,N-diphenylhydrazino,
N-(2-, 3- or 4-methylphenyl)-N-phenylhydrazino,
N-(2-, 3- or 4-methoxyphenyl)-N-phenylhydrazino,
N-(2-, 3- or 4-chlorophenyl)-N-phenylhydrazino,
N-(2-, 3- or 4-fluorophenyl)-N-phenylhydrazino,
N-(2-, 3- or 4-hydroxyphenyl)-N-phenylhydrazino,
N-(2-, 3- or 4-acetamidophenyl)-N-phenylhydrazino,
N-(2-, 3- or 4-methylphenyl)-N-(2-, 3- or 4-methylphenyl)hydrazino, and
N-(2-, 3- or 4-methoxyphenyl)-N-(2-, 3- or 4-methoxyphenyl)hydrazino.

The most preferred such groups include the following groups:
(1-methyl-1-phenylethyl)amino,
[1-methyl-1-(2-, 3- or 4-methylphenyl)ethyl]amino,
[1-methyl-1-(2-, 3- or 4-methoxyphenyl)ethyl]amino,
[1-methyl-1-(2-, 3- or 4-chlorophenyl)ethyl]amino,
[1-methyl-1-(2-, 3- or 4-fluorophenyl)ethyl]amino,
[1-methyl-1-(2-, 3- or 4-acetamidophenyl)ethyl]amino,
(1,1-dimethyl-2-phenylethyl)amino,
benzhydrylamino,
[(2-, 3- or 4-), (2'-, 3'- or 4'-)-difluorobenzhydryl]amino,
[(2-, 3- or 4-), (2'-, 3'- or 4'-)-dimethoxybenzhydryl]amino,
(2-, 3- or 4-chlorobenzhydryl)amino,
(2-, 3- or 4-methoxybenzhydryl)amino,
(2-, 3- or 4-fluorobenzhydryl)amino,
(2-, 3- or 4-hydroxybenzhydryl)amino,
(1,1-diphenylethyl)amino,
(1,2-diphenylethyl)amino,
[2-(2-, 3- or 4-chlorophenyl)-1-phenylethyl]amino,
[2-(2-, 3- or 4-fluorophenyl)-1-phenylethyl]amino,
[2-(2-, 3- or 4-methylphenyl)-1-phenylethyl]amino,
[2-(2-, 3- or 4-methoxyphenyl)-1-phenylethyl]amino,
N,N-dibenzylamino,
N-(2-, 3- or 4-fluorobenzyl)-N-(2-, 3- or 4-fluorobenzyl)amino,
N-(2-, 3- or 4-methylbenzyl)-N-(2-, 3- or 4-methylbenzyl)amino,
N-(2-, 3- or 4-methoxybenzyl)-N-(2-, 3- or 4-methoxybenzyl)amino,
[1-(2- or 3-thienyl)-1-(2- or 3-thienyl)methyl]amino,
[2-phenyl-1-(2- or 3-thienyl)ethyl]amino,
[1-methyl-1-(2- or 3-thienyl)ethyl]amino,
[1-methyl-1-(2- or 3-furyl)ethyl]amino,
[1-methyl-1-(2- or 5-methyl-2- or 3-thienyl)ethyl]amino,
(2-hydroxy-1,2-diphenylethyl)amino,
N,N-diphenylhydrazino,
N-(2-, 3- or 4-methoxyphenyl)-N-phenylhydrazino,
N-(2-, 3- or 4-fluorophenyl)-N-phenylhydrazino, and
N-(2-, 3- or 4-methoxyphenyl)-N-(2-, 3- or 4-methoxyphenyl)hydrazino.

Where the compounds of the present invention contain a carboxy group or a phenolic hydroxy group, they can form salts with bases. There is no particular restriction on the nature of these salts, provided that, where they are intended for therapeutic use, they are pharmaceutically acceptable. Where they are intended for non-therapeutic uses, e.g. as intermediates in the preparation of other, and possibly more active, compounds, even this restriction does not apply. Examples of such salts include: salts with an alkali metal, such as sodium, potassium or lithium; salts with an alkaline earth metal, such as barium or calcium; salts with another metal, such as magnesium and aluminum; organic base salts, such as a salt with dicyclohexylamine; and salts with a basic amino acid, such as lysine or arginine, of which we prefer salts with an alkali metal.

Similarly, such acidic compounds can form esters, and there is likewise no restriction on the nature of such esters, provided that, where they are intended for therapeutic use, they are pharmaceutically acceptable. Examples of such esters include esters: with an alkyl group having from 1 to 6 carbon atoms; with an aryl-substituted alkyl group having from 1 to 6 carbon atoms in its alkyl moiety; or with an alkenyl group having from 3 to 6 carbon atoms; of these we prefer esters with an alkyl group having from 1 to 4 carbon atoms, with a benzyl group, with a benzhydryl group or with an allyl group.

The compounds of the present invention may contain several asymmetric carbon atoms in their molecules, and can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Preferred classes of compounds of the present invention are those compounds of formula (I) and salts and esters thereof in which:

(A) $R^1$ represents a hydrogen atom, an alkyl group having 3 carbon atoms, a benzyl group, a substituted benzyl group having at least one substituent selected from the group consisting of substituents (a), defined below, a furylmethyl group or a thienylmethyl group; and said substituents (a) are selected from the group consisting of alkyl groups having from 1 to 4 carbon atoms, alkoxy groups having from 1 to 4 carbon atoms, halogen atoms, hydroxy groups, alkoxycarbonyl groups having from 2 to 5 carbon atoms and aliphatic carboxylic acylamino groups having from 1 to 5 carbon atoms;

(B) $R^2$ represents a substituted alkyl group having from 1 to 4 carbon atoms and substituted by at least one substituent selected from the group consisting of phenyl groups, substituted phenyl groups having at least one substituent selected from the group consisting of substituents (a), defined in (A) above, furyl groups, furyl groups substituted by a $C_1$–$C_4$ alkyl substituent, thienyl groups and thienyl groups substituted by a $C_1$–$C_4$ alkyl substituent, said alkyl groups having no further substituents or being substituted by at least one substituent selected from the group consisting of carboxy groups and hydroxy groups or a diphenylamino group in which each phenyl group is unsubstituted or one or both of them are substituted by at least one substituent selected from the group consisting of substituents (a), defined in (A) above;

(C) $R^3$ represents a hydrogen atom, an alkyl group having from 1 to 4 carbon atoms, a substituted alkyl group having from 1 to 4 carbon atoms and substituted by at least one substituent selected from the group consisting of phenyl groups, substituted phenyl groups having at least one substituent selected from the group consisting of substituents (a), defined in (A) above, carboxy groups and hydroxy groups or an alkenyl group having 3 or 4 carbon atoms;

(D) the bond represented by $\alpha$-$\beta$ is a carbon-carbon single bond and the bond represented by $\gamma$-$\delta$ is a carbon-carbon single bond or a carbon-carbon double bond, or the bond represented by $\alpha$-$\beta$ is a carbon-carbon double bond and the bond represented by $\gamma$-$\delta$ is a carbon-carbon single bond;

and, of these, we particularly prefer those compounds in which $R^1$ is as defined in (A) above, $R^2$ is as defined in (B) above, $R^3$ is as defined in (C) above and the bonds represented by $\alpha$-$\beta$ and $\gamma$-$\delta$ are as defined in (D) above.

More preferred classes of compounds of the present invention are those compounds of formula (I) and salts and esters thereof in which:

(E) $R^1$ represents a hydrogen atom, an isopropyl group, a benzyl group, a substituted benzyl group having at least one substituent selected from the group consisting of substituents (b), defined below or a thienylmethyl group; and said substituents (b) are selected from the group consisting of methyl groups, ethyl groups, methoxy groups, ethoxy groups, fluorine atoms, chlorine atoms, bromine atoms, hydroxy groups, ethoxycarbonyl groups, methoxycarbonyl groups, formamido groups and acetamido groups;

(F) $R^2$ represents a substituted alkyl group having from 1 to 4 carbon atoms and substituted by at least one substituent selected from the group consisting of phenyl groups, substituted phenyl groups having at least one substituent selected from the group consisting of substituents (b), defined in (E) above, furyl groups, substituted furyl groups having a methyl substituent, thienyl groups and substituted thienyl groups having a methyl substituent, said alkyl groups having no further substituents or being substituted by at least one hydroxy substituent or a diphenylamino group in which each phenyl group is unsubstituted or one or both of them are substituted by at least one substituent selected from the group consisting of substituents (b), defined in (E) above;

(G) $R^3$ represents a hydrogen atom, a methyl group, an ethyl group, a benzyl group, a substituted benzyl group which is substituted by at least one substituent selected from the group consisting of substituents (b), defined in (E) above, a substituted alkyl group having from 1 to 3 carbon atoms and substituted by at least one hydroxy substituent or an allyl group;

and, of these, we particularly prefer those compounds in which $R^1$ is as defined in (E) above, $R^2$ is as defined in (F) above and $R^3$ is as defined in (G) above, and especially those in which, in addition, the bonds represented by $\alpha$-$\beta$ and $\gamma$-$\delta$ are as defined in (D) above.

The most preferred classes of compounds of the present invention are those compounds of formula (I) and salts and esters thereof in which:

(H) $R^1$ and $R^2$ are the same or different and each represents a benzyl group or a substituted benzyl group having at least one substituent selected from the group consisting of substituents (c), defined below;

said substituents (c) are selected from the group consisting of methyl groups, methoxy groups, fluorine atoms, chlorine atoms, hydroxy groups, and acetamido groups; or (H') $R^1$ represents a hydrogen atom and $R^2$ represents a substituted alkyl group having from 1 to 3 carbon atoms and substituted by at least one substituent selected from the group consisting of phenyl groups, substituted phenyl groups having at least one substituent selected from the group consisting of substituents (c), defined in (H) above, furyl groups and thienyl groups or a diphenylamino group in which each phenyl group is unsubstituted or one or both of them are substituted by at least one substituent selected from the group consisting of substituents (c), defined in (H) above;

(I) $R^3$ represents a hydrogen atom, a methyl group or an ethyl group;

and, of these, we particularly prefer those compounds in which $R^1$ and $R^2$ are as defined in (H) or (H') above and $R^3$ is as defined in (I) above, and especially those in which, in addition, the bonds represented by $\alpha$-$\beta$ and $\gamma$-$\delta$ are as defined in (D) above.

Alternative preferred classes of compounds of the present invention are those compounds of formula (I) and salts and esters thereof in which:

(J) $R^1$ represents a hydrogen atom, an unsubstituted alkyl group having from 1 to 6 carbon atoms or a substituted alkyl group having from 1 to 6 carbon atoms which is substituted by at least one substituent selected from the group consisting of aryl groups as defined below, aromatic heterocyclic groups as defined below and carboxy groups;

(K) $R^2$ represents a substituted alkyl group having from 1 to 6 carbon atoms which is substituted by at least one substituent selected from the group consisting of aryl groups as defined below and aromatic heterocyclic groups as defined below, (L) $R^3$ represents a hydrogen atom, an unsubstituted alkyl group having from 1 to 6 carbon atoms, a substituted alkyl group having from 1 to 6 carbon atoms which is substituted by at least one substituent selected from the group consisting of aryl groups as defined below, carboxy groups and hydroxy groups, (M) each of the bonds represented by $\alpha$-$\beta$ and $\gamma$-$\delta$ is a carbon-carbon single bond or a carbon-carbon double bond;

said aryl groups in classes (J) to (L) are carbocyclic aryl groups which have from 6 to 10 ring carbon atoms and which are unsubstituted or are substituted by at least one substituent selected from the group consisting of alkyl groups having from 1 to 4 carbon atoms, alkoxy groups having from 1 to 4 carbon atoms, hydroxy groups and halogen atoms;

said aromatic heterocyclic groups in classes (J) and (K) have 5 or 6 ring atoms of which from one is a hetero-atom selected from the group consisting of nitrogen, oxygen and sulfur hetero-atoms and are unsubstituted or are substituted by at least one substituent selected from the group consisting of alkyl groups having from 1 to 4 carbon atoms, alkoxy groups having from 1 to 4 carbon atoms and halogen atoms;

and, of these, we particularly prefer those compounds in which $R^1$ is as defined in (J) above, $R^2$ is as defined in (K) above and $R^3$ is as defined in (L) above, and especially those in which, in addition, the bonds represented by $\alpha$-$\beta$ and $\gamma$-$\delta$ are as defined in (M) above.

More preferred classes of compounds of the present invention are those compounds of formula (I) and salts and esters thereof in which:

(N) $R^1$ represents a hydrogen atom, an unsubstituted alkyl group having from 1 to 4 carbon atoms or a substituted alkyl group having from 1 to 4 carbon atoms which is substituted by one substituent selected from the group consisting of phenyl groups, substituted phenyl groups having at least one substituent selected from the group consisting of $C_1$-$C_4$ alkyl, $C_1$-$C_4$ alkoxy, halogen and hydroxy substituents, a furyl group and a thienyl group;

(O) $R^2$ represents a substituted alkyl group having from 1 to 4 carbon atoms and substituted by from 1 to 3 substituents selected from the group consisting of phenyl groups, substituted phenyl groups having at least one substituent selected from the group consisting of alkyl groups having from 1 to 4 carbon atoms, alkoxy groups having from 1 to 4 carbon atoms, halogen atoms and hydroxy groups, a furyl group or a thienyl group;

(P) $R^3$ represents a hydrogen atom, an alkyl group having from 1 to 4 carbon atoms, a substituted alkyl group having from 1 to 4 carbon atoms and having at least one substituents selected from the group consisting of phenyl groups, carboxy groups and hydroxy groups, or an alkenyl group having 3 or 4 carbon atoms;

(Q) the bond represented by $\alpha$-$\beta$ is a carbon-carbon single bond and the bond represented by $\gamma$-$\delta$ is a carbon-carbon single bond or a carbon-carbon double bond or the bond represented by $\alpha$-$\beta$ is a carbon-carbon double bond and the bond represented by $\gamma$-$\delta$ is a carbon-carbon single bond;

and, of these, we particularly prefer those compounds in which $R^1$ is as defined in (N) above, $R^2$ is as defined in (O) above and $R^3$ is as defined in (P) above, and especially those in which, in addition, the bonds represented by $\alpha$-$\beta$ and $\gamma$-$\delta$ are as defined in (Q) above.

Much more preferred classes of compounds of the present invention are those compounds of formula (I) and salts and esters thereof in which:

(R) $R^1$ represents a hydrogen atom and $R^2$ represents a group of formula:

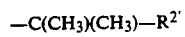

in which $R^{2'}$ represents a phenyl group, a substituted phenyl group having at least one substituent selected from the group consisting of methyl, methoxy, chloro, fluoro and hydroxy substituents, or a substituted alkyl group having from 1 to 3 carbon atoms and having 2 or 3 substituents selected from the group consisting of phenyl groups, substituted phenyl groups having at least one substituent selected from the group consisting of methyl, methoxy, fluoro, chloro and hydroxy substituents, furyl groups and thienyl groups; or (R') $R^1$ and $R^2$ are same or different and each represents a substituted alkyl group having from 1 to 3 carbon atoms and having one substituent selected from the group consisting of phenyl groups, substituted phenyl groups having at least one substituent selected from the group consisting of methyl, methoxy, fluoro, chloro and hydroxy substituents, furyl groups and thienyl groups;

(S) $R^3$ represents a hydrogen atom, a methyl group an ethyl group, an allyl group or a benzyl group;

(T) the bond represented by $\alpha$-$\beta$ is a carbon-carbon single bond or a carbon-carbon double bond and the bond represented by $\gamma$-$\delta$ is a carbon-carbon single bond;

and, of these, we particularly prefer those compounds in which $R^1$ and $R^2$ are as defined in (R) or (R') above and $R^3$ is as defined in (S) above, and especially those in which, in addition, the bonds represented by $\alpha$-$\beta$ and $\gamma$-$\delta$ are as defined in (T) above.

The most preferred classes of compounds of the present invention are those compounds of formula (I) and salts and esters thereof in which:

(U) $R^1$ represents a hydrogen atom and $R^2$ represents a diphenylmethyl group, substituted diphenylmethyl group having at least one substituent selected from the group consisting of methyl, methoxy, fluoro, chloro or hydroxy substituents, a 1,2-diphenylethyl group, a substituted 1,2-diphenylethyl group having at least one substituent selected from the group consisting of methyl, methoxy, fluoro, chloro or hydroxy substituents, a 1,1-diphenylethyl group or a substituted 1,1-diphenylethyl group having at least one substituent selected from the group consisting of methyl, methoxy, fluoro, chloro or hydroxy substituents;

(V) $R^3$ represents a hydrogen atom, a methyl group, or an ethyl group;

and, of these, we particularly prefer those compounds in which $R^1$ and $R^2$ are as defined in (U) above and $R^3$ is as defined in (V) above, and especially those in which, in addition, the bonds represented by $\alpha$-$\beta$ and $\gamma$-$\delta$ are as defined in (T) above.

Examples of certain of the compounds of the present invention are shown by the following formulae (I-1), (I-2) and (I-3), in which the symbols used in the formulae are as defined in the respective one of Tables 1, 2 and 3, that is Table 1 relates to formula (I-1), Table 2 relates to formula (I-2) and Table 3 relates to formula (I-3).

In the Tables, the following abbreviations are used for certain of the substituent groups:

| | |
|---|---|
| Ac | acetyl |
| All | allyl |
| Bu | butyl |
| Bz | benzyl |
| Bzhy | benzhydryl |
| Et | ethyl |
| Fur | furyl |
| Me | methyl |
| Mec | methoxycarbonyl |
| Ph | phenyl |
| Pr | propyl |
| Thi | thienyl |

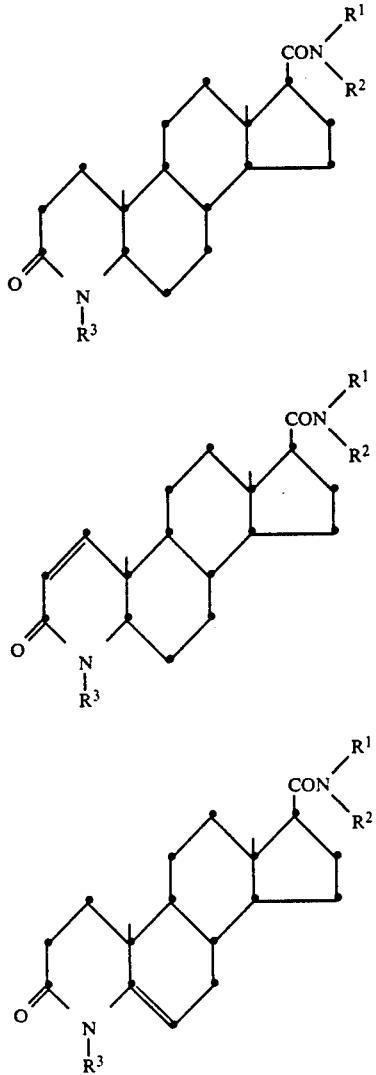

(I-1)

(I-2)

(I-3)

TABLE 1

| Cpd. No. | R¹ | R² | R³ |
|---|---|---|---|
| 1-1 | H | 1,2-diPhEt | H |
| 1-2 | H | Bzhy | H |
| 1-3 | H | 1,1-diPhEt | H |
| 1-4 | Bz | Bz | H |
| 1-5 | H | 1,2-di(2-Thi)Et | H |
| 1-6 | H | 1,2-bis(4-FPh)Et | H |
| 1-7 | H | 1,2-bis(4-MePh)Et | H |
| 1-8 | H | 1,2-bis(4-MeOPh)Et | H |
| 1-9 | H | 1,2-bis(4-ClPh)Et | H |
| 1-10 | H | di(2-Thi)CH— | H |
| 1-11 | H | 1,2-di(2-Thi)Et | Me |
| 1-12 | H | bis(4-FPh)CH— | H |
| 1-13 | H | bis(4-MePh)CH— | H |
| 1-14 | H | bis(4-MeOPh)CH— | H |
| 1-15 | H | 2-(4-MeOPh)-1-(2-Thi)Et | H |
| 1-16 | H | 2-(4-FPh)-1-(2-Thi)Et | H |
| 1-17 | H | 2-(4-MePh)-1-(2-Thi)Et | H |
| 1-18 | H | 2-(4-ClPh)-1-(2-Thi)Et | H |
| 1-19 | H | 1-(2-Fur)-2-PhEt | H |
| 1-20 | H | 2-Ph-1-(2-Thi)Et | H |
| 1-21 | H | di(3-Thi)CH— | H |
| 1-22 | H | 2-(4-MePh)-1-PhEt | H |
| 1-23 | H | 2-(4-FPh)-1-(4-MePh)Et | H |
| 1-24 | H | 2-(4-MeOPh)-1-PhEt | H |
| 1-25 | H | 2-(4-FPh)-1-(4-MeOPh)Et | H |
| 1-26 | H | 1-Bz-4-PhBu | H |
| 1-27 | H | 4-ClBzhy | H |
| 1-28 | H | 4-MeOBzhy | H |
| 1-29 | H | 4-FBzhy | H |
| 1-30 | H | 4-F-4'-MeOBzhy | H |
| 1-31 | H | 4-MeBzhy | H |
| 1-32 | H | 2-Ph-1-(2-Thi)Et | Me |
| 1-33 | H | 1,1-diBzEt | H |
| 1-34 | H | 1,1-di(2-Thi)Et | H |
| 1-35 | H | 1,1-di(2-Thi)Et | Me |
| 1-36 | H | Bzhy | Me |
| 1-37 | H | 1,2-diPhEt | Et |
| 1-38 | H | 1,2-diPhEt | Me |
| 1-39 | H | 1,1-diPhEt | Me |
| 1-40 | H | 1-Bz-1-PhEt | H |
| 1-41 | H | 1,2-diPhPr | H |
| 1-42 | 4-HOBz | 4-HOBz | H |
| 1-43 | 4-FBz | 4-FBz | H |
| 1-44 | H | 1-Me-1-PhEt | H |
| 1-45 | H | 1-Me-1-(2-Thi)Et | H |
| 1-46 | H | 1-Me-1-(2-Thi)Et | Me |
| 1-47 | H | 1-Me-1-PhEt | Me |
| 1-48 | H | 1,1-diMe-2-PhEt | H |
| 1-49 | H | 1-Me-1-(4-HOPh)Et | H |
| 1-50 | H | 1-Me-1-(4-FPh)Et | H |
| 1-51 | H | 1-Mec-1,1-diPhC— | H |
| 1-52 | H | di(2-Fur)CH— | H |
| 1-53 | H | 4,4'-diHOBzhy | H |
| 1-54 | H | 1,2-bis(4-HOPh)Et | H |
| 1-55 | H | 1,2-bis(4-HOPh)-1-MeEt | H |
| 1-56 | H | Bzhy | —CH₂COOH |
| 1-57 | H | Bzhy | —(CH₂)₂COOH |
| 1-58 | iPr | Bz | H |
| 1-59 | Et | Bz | H |
| 1-60 | Me | Bz | H |
| 1-61 | iBu | Bz | H |
| 1-62 | iPr | 4-FBz | H |
| 1-63 | iPr | 4-ClBz | H |
| 1-64 | iPr | 4-MeBz | H |
| 1-65 | iPr | 4-MeOBz | H |
| 1-66 | iPr | 4-HOBz | H |
| 1-67 | 2-ThiMe | 2-ThiMe | H |
| 1-68 | 2-ThiMe | Bz | H |
| 1-69 | H | Bzhy | Et |
| 1-70 | Bz | Bz | Me |
| 1-71 | Bz | Bz | Et |
| 1-72 | H | di(2-Thi)CH— | Me |
| 1-73 | H | di(2-Thi)CH— | Et |
| 1-74 | H | 2-(4-MePh)-1-PhEt | Me |
| 1-75 | H | 2-(4-MePh)-1-PhEt | Et |
| 1-76 | H | 1,1-diPhEt | Me |
| 1-77 | H | 1-Me-1-PhEt | Et |
| 1-78 | H | 1-Me-1-(2-Thi)Et | Et |
| 1-79 | H | 1,1-diMe-2-PhEt | Me |
| 1-80 | H | 4,4'-diMeOBzhy | Me |
| 1-81 | H | 4-HOBzhy | H |
| 1-82 | H | 4-HOBzhy | Me |
| 1-83 | H | 4-HOBzhy | Et |
| 1-84 | H | 4-MeOBzhy | Et |
| 1-85 | H | 4-MeOBzhy | Me |
| 1-86 | H | 4-ClBzhy | H |
| 1-87 | H | 4-ClBzhy | Me |
| 1-88 | H | 1-(4-MeOPh)-1-MeEt | H |
| 1-89 | H | 1-(4-MeOPh)-1-MeEt | Me |
| 1-90 | H | 1-(4-MeOPh)-1-MeEt | Et |
| 1-91 | H | 1-(3,5-diMeOPh)-1-MeEt | H |
| 1-92 | H | 1-(3,5-diMeOPh)-1-MeEt | Me |
| 1-93 | H | 1-(4-FPh)-1-MeEt | Et |
| 1-94 | H | 1-(4-FPh)-1-MeEt | Me |
| 1-95 | H | 1-(4-AcNHPh)-1-MeEt | H |
| 1-96 | H | 1-(4-AcNHPh)-1-MeEt | Me |
| 1-97 | H | 2-HO-1,2-diPhEt | H |
| 1-98 | H | 2-HO-1,2-diPhEt | Me |
| 1-99 | H | 2-HO-1,2-diPhEt | Et |
| 1-100 | H | Ph₂N— | H |
| 1-101 | H | Ph₂N— | Me |
| 1-102 | H | Ph₂N— | Et |
| 1-103 | H | 1-Me-1-(3-MeOPh)Et | H |
| 1-104 | H | 1-Me-1-(3-MeOPh)Et | Me |
| 1-105 | H | 1-Me-1-(2-MeOPh)Et | H |
| 1-106 | H | 1-Me-1-(2-MeOPh)Et | Me |

TABLE 1-continued

| Cpd. No. | R¹ | R² | R³ |
|---|---|---|---|
| 1-107 | H | 2,2-diPhEt | H |
| 1-108 | H | 3,3-diPhPr | H |
| 1-109 | H | Bzhy | Et |
| 1-110 | H | Bzhy | All |
| 1-111 | H | Bzhy | Bz |
| 1-112 | H | Bzhy | Me |
| 1-113 | H | Bzhy | $CH_2CH_2CH_2OH$ |
| 1-114 | H | 1-Me-1-(2-Fur)Et | H |
| 1-115 | H | 1-Me-1-(2-Fur)Et | Me |

TABLE 2

| Cpd. No. | R¹ | R² | R³ |
|---|---|---|---|
| 2-1 | H | 1,2-diPhEt | H |
| 2-2 | H | 1,2-diPhEt | Me |
| 2-3 | H | 1,2-diPhEt | Et |
| 2-4 | H | Bzhy | H |
| 2-5 | H | Bzhy | Me |
| 2-6 | H | Bzhy | Et |
| 2-7 | Bz | Bz | H |
| 2-8 | Bz | Bz | Me |
| 2-9 | Bz | Bz | Et |
| 2-10 | H | di(2-Thi)CH— | H |
| 2-11 | H | di(2-Thi)CH— | Me |
| 2-12 | H | 4,4'-diMeOBzhy | H |
| 2-13 | H | 4,4'-diMeOBzhy | Me |
| 2-14 | H | 2-Ph-1-(2-Thi)Et | H |
| 2-15 | H | 2-Ph-1-(2-Thi)Et | Me |
| 2-16 | H | 2-(4-MePh)-1-PhEt | H |
| 2-17 | H | 2-(4-MePh)-1-PhEt | Me |
| 2-18 | H | 1,1-diPhEt | H |
| 2-19 | H | 1,1-diPhEt | Me |
| 2-20 | H | 1-Me-1-PhEt | H |
| 2-21 | H | 1-Me-1-PhEt | Me |
| 2-22 | H | 1-Me-1-PhEt | Et |
| 2-23 | H | 1-Me-1-(2-Thi)Et | H |
| 2-24 | H | 1-Me-1-(2-Thi)Et | Me |
| 2-25 | H | 1-Me-1-(2-Thi)Et | Et |
| 2-26 | H | 1,1-diMe-2-PhEt | H |
| 2-27 | H | 1,1-diMe-2-PhEt | Me |
| 2-28 | H | 4-HOBzhy | H |
| 2-29 | H | 4-HOBzhy | Me |
| 2-30 | H | 4-HOBzhy | Et |
| 2-31 | H | 4-MeOBzhy | H |
| 2-32 | H | 4-MeOBzhy | Me |
| 2-33 | H | 4-ClBzhy | H |
| 2-34 | H | 4-ClBzhy | Me |
| 2-35 | H | 1-(4-MeOPh)-1-MeEt | H |
| 2-36 | H | 1-(4-MeOPh)-1-MeEt | Me |
| 2-37 | H | 1-(4-MeOPh)-1-MeEt | Et |
| 2-38 | H | 1-3,5-diMeOPh)-1-MeEt | H |
| 2-39 | H | 1-(3,5-diMeOPh)-1-MeEt | Me |
| 2-40 | H | 1-(4-FPh)-1-MeEt | H |
| 2-41 | H | 1-(4-FPh)-1-MeEt | Me |
| 2-42 | H | 1-(4-AcNHPh)-1-MeEt | H |
| 2-43 | H | 1-(4-AcNHPh)-1-MeEt | Me |
| 2-44 | H | 2-HO-1,2-diPhEt | H |
| 2-45 | H | 2-HO-1,2-diPhEt | Me |
| 2-46 | H | 2-HO-1,2-diPhEt | Et |
| 2-47 | H | $Ph_2N$— | H |
| 2-48 | H | $Ph_2N$— | Me |
| 2-49 | H | $Ph_2N$— | Et |
| 2-50 | H | 1-Me-1-(3-MeOPh)Et | H |
| 2-51 | H | 1-Me-1-(3-MeOPh)Et | Me |
| 2-52 | H | 1-Me-1-(2-MeOPh)Et | H |
| 2-53 | H | 1-Me-1-(2-MeOPh)Et | Me |
| 2-54 | H | 2,2-diPhEt | H |
| 2-55 | iPr | Bz | H |
| 2-56 | H | 1,2-di(2-Thi)Et | H |
| 2-57 | H | 2-(4-MePh)-1-(2-Thi)Et | H |
| 2-58 | H | 2-(4-MeOPh)-1-PhEt | H |
| 2-59 | H | 2-(4-MeOPh)-1-(2-Thi)Et | H |
| 2-60 | H | 1-Me-1-(2-Fur)Et | H |
| 2-61 | H | 1-Me-1-(2-Fur)Et | Me |

TABLE 3

| Cpd. No. | R¹ | R² | R³ |
|---|---|---|---|
| 3-1 | H | 1,2-diPhEt | H |
| 3-2 | H | 1,2-diPhEt | Me |
| 3-3 | H | 1,2-diPhEt | Et |
| 3-4 | H | Bzhy | H |
| 3-5 | H | Bzhy | Me |
| 3-6 | H | Bzhy | Et |
| 3-7 | Bz | Bz | H |
| 3-8 | Bz | Bz | Me |
| 3-9 | Bz | Bz | Et |
| 3-10 | H | di(2-Thi)CH— | H |
| 3-11 | H | di(2-Thi)CH— | Me |
| 3-12 | H | 4,4'-diMeOBzhy | H |
| 3-13 | H | 4,4'-diMeOBzhy | Me |
| 3-14 | H | 2-Ph-1-(2-Thi)Et | H |
| 3-15 | H | 2-Ph-1-(2-Thi)Et | Me |
| 3-16 | H | 2-(4-MePh)-1-PhEt | H |
| 3-17 | H | 2-(4-MePh)-1-PhEt | Me |
| 3-18 | H | 1,1-diPhEt | H |
| 3-19 | H | 1,1-diPhEt | Me |
| 3-20 | H | 1-Me-1-PhEt | H |
| 3-21 | H | 1-Me-1-PhEt | Me |
| 3-22 | H | 1-Me-1-PhEt | Et |
| 3-23 | H | 1-Me-1-(2-Thi)Et | H |
| 3-24 | H | 1-Me-1-(2-Thi)Et | Me |
| 3-25 | H | 1-Me-1-(2-Thi)Et | Et |
| 3-26 | H | 1,1-diMe-2-PhEt | H |
| 3-27 | H | 1,1-diMe-2-PhEt | Me |
| 3-28 | H | 4-HOBzhy | H |
| 3-29 | H | 4-HOBzhy | Me |
| 3-30 | H | 4-HOBzhy | Et |
| 3-31 | H | 4-MeOBzhy | H |
| 3-32 | H | 4-MeOBzhy | Me |
| 3-33 | H | 4-ClBzhy | H |
| 3-34 | H | 4-ClBzhy | Me |
| 3-35 | H | 1-(4-MeOPh)-1-MeEt | H |
| 3-36 | H | 1-(4-MeOPh)-1-MeEt | Me |
| 3-37 | H | 1-(4-MeOPh)-1-MeEt | Et |
| 3-38 | H | 1-(3,5-diMeOPh)-1-MeEt | H |
| 3-39 | H | 1-(3,5-diMeOPh)-1-MeEt | Me |
| 3-40 | H | 1-(4-FPh)-1-MeEt | H |
| 3-41 | H | 1-(4-FPh)-1-MeEt | Me |
| 3-42 | H | 1-(4-AcNHPh)-1-MeEt | H |
| 3-43 | H | 1-(4-AcNHPh)-1-MeEt | Me |
| 3-44 | H | 2-HO-1,2-diPhEt | H |
| 3-45 | H | 2-HO-1,2-diPhEt | Me |
| 3-46 | H | 2-HO-1,2-diPhEt | Et |
| 3-47 | H | $Ph_2N$— | H |
| 3-48 | H | $Ph_2N$— | Me |
| 3-49 | H | $Ph_2N$— | Et |
| 3-50 | H | 1-Me-1-(3-MeOPh)Et | H |
| 3-51 | H | 1-Me-1-(3-MeOPh)Et | Me |
| 3-52 | H | 1-Me-1-(2-MeOPh)Et | H |
| 3-53 | H | 1-Me-1-(2-MeOPh)Et | Me |
| 3-54 | H | 1-Me-1,1-diPh.C— | H |
| 3-55 | H | 1,2-di(2-Thi)Et | H |
| 3-56 | H | 1,2-di(2-Thi)Et | Me |
| 3-57 | H | 1-Me-1-(2-Fur)Et | H |
| 3-58 | H | 1-Me-1-(2-Fur)Et | Me |

On the compounds listed above, the following are preferred, that is to say Compounds No. 1-1, 1-2, 1-3, 1-4, 1-5, 1-11, 1-14, 1-16, 1-20, 1-22, 1-28, 1-32, 1-36, 1-38, 1-39, 1-44, 1-45, 1-46, 1-47, 1-48, 1-57, 1-58, 1-70, 1-74, 1-75, 1-76, 1-81, 1-82, 1-85, 1-86, 1-87, 1-88, 1-89, 1-95, 1-96, 1-97, 1-100, 1-101, 1-104, 1-107, 1-108, 1-109, 1-110, 1-111, 1-112, 1-113, 1-114, 1-115, 2-1, 2-2, 2-4, 2-5, 2-7, 2-8, 2-12, 2-14, 2-16, 2-17, 2-18, 2-19, 2-20, 2-21, 2-23, 2-24, 2-26, 2-28, 2-29, 2-31, 2-33, 2-34, 2-35, 2-36, 2-42, 2-43, 2-44, 2-47, 2-48, 2-52, 2-54, 2-55, 2-56, 2-57, 2-58, 2-59, 2-60, 2-61, 3-1, 3-2, 3-4, 3-5, 3-7, 3-8, 3-12, 3-14, 3-15, 3-16, 3-17, 3-18, 3-19, 3-20, 3-21, 3-23, 3-24, 3-28, 3-29, 3-31, 3-32, 3-33, 3-34, 3-35, 3-36, 3-42, 3-43, 3-45, 3-47, 3-48, 3-50, 3-53, 3-54, 3-55, 3-56, 3-57 and 3-58.

The most preferred compounds are Compounds No.:

1-1. N-(1,2-Diphenylethyl)-3-oxo-4-aza-5α-androstane-17β-carboxamide;
1-2. N-(Diphenylmethyl)-3-oxo-4-aza-5α-androstane-17β-carboxamide;
1-3. N-(1,1-Diphenylethyl)-3-oxo-4-aza-5α-androstane-17β-carboxamide;
1-22. N-[2-(4-Methylphenyl)-1-phenylethyl]-3-oxo-4-aza-5α-androstane-17β-carboxamide;
1-36. N-(Diphenylmethyl)-4-methyl-3-oxo-4-aza-5α-androstane-17β-carboxamide;
1-38. N-(1,2-Diphenylethyl)-4-methyl-3-oxo-4-aza-5α-androstane-17β-carboxamide; 1-44. N-(1-Methyl-1-phenylethyl)-3-oxo-4-aza-5α-androstane-17β-carboxamide;
1-45. N-[1-methyl-1-(2-thienyl)ethyl]-3-oxo-4-aza-5α-androstane-17β-carboxamide;
1-46. N-[1-methyl-1-(2-thienyl)ethyl]-4-methyl-3-oxo-4-aza-5α-androstane-17β-carboxamide;
1-47. N-(1-Methyl-1-phenylethyl)-4-methyl-3-oxo-4-aza-5α-androstane-17β-carboxamide;
1-74. N-[2-(4-Methylphenyl)-1-phenylethyl]-4-methyl-3-oxo-4-aza-5α-androstane-17β-carboxamide;
1-76. N-(1,1-Diphenylethyl)-4-methyl-3-oxo-4-aza-5α-androstane-17β-carboxamide;
1-81. N-[α-(4-Hydroxyphenyl)benzyl]-3-oxo-4-aza-5α-androstane-17β-carboxamide;
1-82. N-[α-(4-Hydroxyphenyl)benzyl]-4-methyl-3-oxo-4-aza-5α-androstane-17β-carboxamide;
1-88. N-[1-(4-Methoxyphenyl)-1-methylethyl]-3-oxo-4-aza-5α-androstane-17β-carboxamide;
1-89. N-[1-(4-Methoxyphenyl)-1-methylethyl]-4-methyl-3-oxo-4-aza-5α-androstane-17β-carboxamide;
1-100. N,N-Diphenyl-3-oxo-4-aza-5α-androstane-17β-carbohydrazide;
1-101. N,N-Diphenyl-4-methyl-3-oxo-4-aza-5α-androstane-17β-carbohydrazide;
1-104. N-[1-(3-Methoxyphenyl)-1-methylethyl]-4-methyl-3-oxo-4-aza-5α-androstane-17β-carboxamide;
1-114. N-[1-Methyl-1-(2-furyl)ethyl]-3-oxo-4-aza-5α-androstane-17β-carboxamide;
2-1. N-(1,2-Diphenylethyl)-3-oxo-4-aza-5α-androst-1-ene-17β-carboxamide;
2-2. N-(1,2-Diphenylethyl)-4-methyl-3-oxo-4-aza-5α-androst-1-ene-17β-carboxamide;
2-4. N-(Diphenylmethyl)-3-oxo-4-aza-5α-androst-1-ene-17β-carboxamide;
2-5. N-(Diphenylmethyl)-4-methyl-3-oxo-4-aza-5α-androst-1-ene-17β-carboxamide;
2-16. N-[1-Phenyl-2-(4-methylphenyl)ethyl]-3-oxo-4-aza-5α-androst-1-ene-17β-carboxamide;
2-17. N-[1-Phenyl-2-(4-methylphenyl)ethyl]-4-methyl-3-oxo-4-aza-5α-androst-1-ene-17β-carboxamide;
2-18. N-(1,1-Diphenylethyl)-3-oxo-4-aza-5α-androst-1-ene-17β-carboxamide;
2-19. N-(1,1-Diphenylethyl)-4-methyl-3-oxo-4-aza-5α-androst-1-ene-17β-carboxamide;
2-20. N-(1-Methyl-1-phenylethyl)-3-oxo-4-aza-5α-androst-1-ene-17β-carboxamide;
2-21. N-(1-Methyl-1-phenylethyl)-4-methyl-3-oxo-4-aza-5α-androst-1-ene-17β-carboxamide;
2-23. N-[1-methyl-1-(2-thienyl)ethyl]-3-oxo-4-aza-5α-androst-1-ene-17β-carboxamide;
2-24. N-[1-methyl-1-(2-thienyl)ethyl]-4-methyl-3-oxo-4-aza-5α-androst-1-ene-17β-carboxamide;
2-28. N-[α-(4-Hydroxyphenyl)benzyl]-3-oxo-4-aza-5α-androst-1-ene-17β-carboxamide;
2-29. N-[α-(4-Hydroxyphenyl)benzyl]-4-methyl-3-oxo-4-aza-5α-androst-1-ene-17β-carboxamide;
2-35. N-[1-(4-Methoxyphenyl)-1-methylethyl]-3-oxo-4-aza-5α-androst-1-ene-17β-carboxamide;
2-36. N-[1-(4-Methoxyphenyl)-1-methylethyl]-4-methyl-3-oxo-4-aza-5α-androst-1-ene-17β-carboxamide;
2-44. N-(2-Hydroxy-1,2-diphenylethyl)-3-oxo-4-aza-5α-androst-1-ene-17β-carboxamide;
2-47. N,N-Diphenyl-3-oxo-4-aza-5α-androst-1-ene-17β-carbohydrazide;
2-48. N,N-Diphenyl-4-methyl-3-oxo-4-aza-5α-androst-1-ene-17β-carbohydrazide;
2-52. N-[1-(2-Methoxyphenyl)-1-methylethyl]-3-oxo-4-aza-5α-androst-1-ene-17β-carboxamide;
2-60. N-[1-Methyl-1-(2-furyl)ethyl]-3-oxo-4-aza-5α-androst-1-ene-17β-carboxamide;
3-1. N-(1,2-Diphenylethyl)-3-oxo-4-azaandrost-5-ene-17β-carboxamide;
3-2. N-(1,2-Diphenylethyl)-4-methyl-3-oxo-4-azaandrost-5-ene-17β-carboxamide;
3-4. N-(Diphenylmethyl)-3-oxo-4-azaandrost-5-ene-17β-carboxamide;
3-5. N-(Diphenylmethyl)-4-methyl-3-oxo-4-azaandrost-5-ene-17β-carboxamide;
3-16. N-[2-(4-Methylphenyl)-1-phenylethyl]-3-oxo-4-azaandrost-5-ene-17β-carboxamide;
3-17. N-[2-(4-Methylphenyl)-1-phenylethyl]-4-methyl-3-oxo-4-azaandrost-5-ene-17β-carboxamide;
3-18. N-(1,1-Diphenylethyl)-3-oxo-4-azaandrost-5-ene-17β-carboxamide;
3-19. N-(1,1-Diphenylethyl)-4-methyl-3-oxo-4-azaandrost-5-ene-17β-carboxamide;
3-20. N-(1-Methyl-1-phenylethyl)-3-oxo-4-azaandrost-5-ene-17β-carboxamide;
3-21. N-(1-Methyl-1-phenylethyl)-4-methyl-3-oxo-4-azaandrost-5-ene-17β-carboxamide;
3-23. N-[1-methyl-1-(2-thienyl)ethyl]-3-oxo-4-azaandrost-5-ene-17β-carboxamide;
3-24. N-[1-methyl-1-(2-thienyl)ethyl]-4-methyl-3-oxo-4-azaandrost-5-ene-17β-carboxamide;
3-28. N-[α-(4-Hydroxyphenyl)benzyl]-3-oxo-4-azaandrost-5-ene-17β-carboxamide;
3-29. N-[α-(4-Hydroxyphenyl)benzyl]-4-methyl-3-oxo-4-azaandrost-5-ene-17β-carboxamide;
3-35. N-[1-(4-Methoxyphenyl)-1-methylethyl]-3-oxo-4-azaandrost-5-ene-17β-carboxamide;
3-36. N-[1-(4-Methoxyphenyl)-1-methylethyl]-4-methyl-3-oxo-4-azaandrost-5-ene-17β-carboxamide;
3-45. N-(2-Hydroxy-1,2-diphenylethyl)-4-methyl-3-oxo-4-azaandrost-5-ene-17β-carboxamide;
3-47. N,N-Diphenyl-3-oxo-4-azaandrost-5-ene-17β-carbohydrazide;
3-48. N,N-Diphenyl-4-methyl-3-oxo-4-azaandrost-5-ene-17β-carbohydrazide;
3-50. N-[1-(3-Methoxyphenyl)-1-methylethyl]-3-oxo-4-azaandrost-5-ene-17β-carboxamide;
3-53. N-[1-(2-Methoxyphenyl)-1-methylethyl]-4-methyl-3-oxo-4-azaandrost-5-ene-17β-carboxamide;
3-58. N-[1-Methyl-1-(2-furyl)ethyl]-4-methyl-3-oxo-4-azaandrost-5-ene-17β-carboxamide.

The compounds of the present invention may be prepared by a variety of methods well known for the preparation of compounds of this type. For example, in general terms, they may be prepared by:

(a) reacting an amino compound of formula (II):

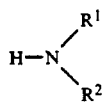
(II)

(in which R¹ and R² are as defined above) with an azasteroid derivative of formula (III):

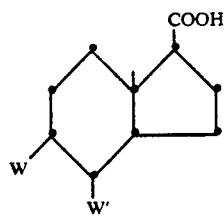
(III)

in which W and W' together represent a group of formula (IV):

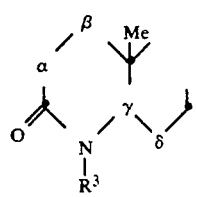
(IV)

or a group of formula (IVa):

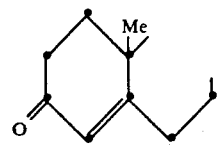
(IVa)

(in which α-β, γ-δ and R³ are as defined above and Me is methyl);

(b) where W and W' together represent a group of formula (IVa), oxidizing the compound produced in step (a) to convert said group to a group of formula (IVb):

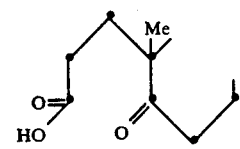
(IVb)

and reacting the resulting compound with a compound of formula (V):

NH₂R³     (V)

(in which R³ is as defined above) to convert the group to a group of formula (IV);

(c) if desired, converting a group represented by R³ to any other such group;

(d) if desired, converting a carbon-carbon single bond represented by α-β to a carbon-carbon double bond;

(e) if desired, at any stage, salifying or esterifying the compound.

In more detail, these reactions may be carried out as follows:

Reaction (A)

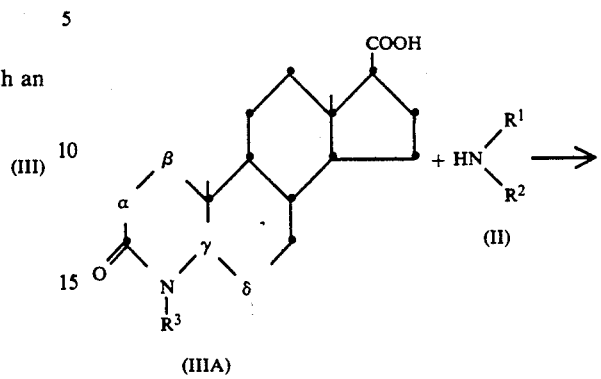

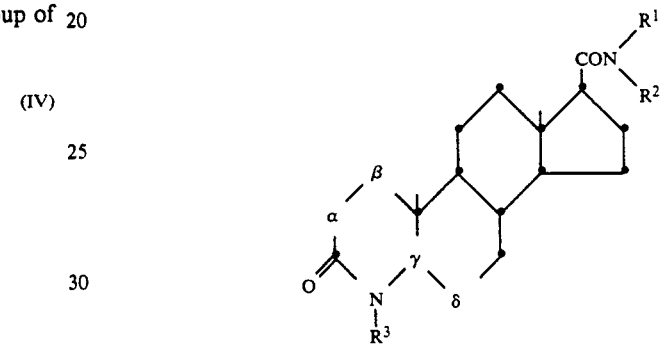

In this reaction, a compound of formula (I) is prepared by reacting an azasteroid derivative of formula (IIIA) or a reactive derivative thereof with a compound of formula (II). When the compound of formula (II) contains one or more carboxy groups, these carboxy groups are preferably protected prior to this reaction, using protecting groups and reagents well known in the art. Examples of carboxy-protecting groups include the t-butyl, benzhydryl, 4-methylbenzhydryl and 4-methoxybenzhydryl groups. The reaction may be carried out using any conventional method which may be employed for the synthesis of peptides, such as the azide method, the active ester method, the mixed acid anhydride method or the condensation method.

Following this reaction, the carboxy-protecting groups can be removed by conventional means, depending upon the nature of the protecting group, e.g. by treatment of the resulting compound with an acid in an inert solvent. Examples of acids which may be employed include: hydrohalic acids, such as hydrochloric acid, hydrobromic acid and hydriodic acid; and strong organic carboxylic and sulfonic acids, such as trifluoroacetic acid, trichloroacetic acid and trifluoromethanesulfonic acid; of these, we prefer the organic acids. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride or chloroform; and aryl ethers, such as anisole or diphenyl ether; or a mixture of any two or more thereof, of which we prefer the mixture.

The reaction can take place over a wide range of temperatures, and the precise reaction temperature is not critical to the invention. In general, we find it convenient to carry out the reaction at a temperature of from −20° C. to 50° C., more preferably from −10° C. to about room temperature. The time required for the reaction may also vary widely, depending on many factors, notably the reaction temperature and the nature of the reagents. However, provided that the reaction is effected under the preferred conditions outlined above, a period of from 30 minutes to 20 hours, more preferably from 1 hour to 10 hours, will usually suffice.

The Azide Method

The azide method may be carried out by reacting the compound of formula (IIIA) or an ester thereof with hydrazine in an inert solvent (e.g. dimethylformamide) at or about room temperature to prepare an amino acid hydrazide which may then be converted into the corresponding azide compound by reaction with a nitrous acid compound; the azide is then allowed to react with the amino compound of formula (II).

Examples of nitrous acid compounds which may be employed include: alkali metal nitrites, such as sodium nitrite; and alkyl nitrites, such as isoamyl nitrite.

The reaction is preferably carried out in the presence of an inert solvent. There is no particular restriction on the nature of the solvent to be employed, provided that it has no adverse effect on the reaction or on the reagents involved and that it can dissolve the reagents, at least to some extent. Examples of suitable solvents include: amides, especially fatty acid amides, such as dimethylformamide or dimethylacetamide; sulfoxides, such as dimethyl sulfoxide; and pyrrolidones, such as N-methylpyrrolidone. The two steps of this method are usually performed in a single reaction solution, without isolation of the intermediate compound. The reactions can take place over a wide range of temperatures, and the precise reaction temperature is not critical to the invention. In general, we find it convenient to carry out the reaction of the first step at a temperature of from −50° C. to 0° C. and the reaction of the second step at a temperature of from −10° C. to +10° C. The time required for the reactions may also vary widely, depending on many factors, notably the reaction temperature and the nature of the reagents. However, provided that the reaction is effected under the preferred conditions outlined above, periods of from 5 minutes to 1 hour and 10 hours to 5 days will usually suffice for the first step and the second step, respectively.

The Active Ester Method

The active ester method may be carried out by reacting the compound of formula (IIIA) with an esterification agent to prepare an active ester, and then reacting the active ester thus obtained with an amino compound of formula (II).

Both reactions are preferably carried out in an inert solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, especially halogenated aliphatic hydrocarbons, such as methylene chloride or chloroform; ethers, such as diethyl ether or tetrahydrofuran; amides, especially fatty acid amides, such as dimethylformamide or dimethylacetamide; and nitriles, such as acetonitrile.

Suitable esterification agents which may be employed in this reaction include: N-hydroxy compounds, such as N-hydroxysuccinimide, 1-hydroxybenzotriazole and N-hydroxy-5-norbornene-2,3-dicarboximide; and disulfide compounds, such as dipyridyl disulfide. The reaction to prepare the active ester is preferably performed in the presence of a condensing agent, such as dicyclohexylcarbodiimide, carbonyldiimidazole or triphenylphosphine.

These reactions can take place over a wide range of temperatures, and the precise reaction temperature is not critical to the invention. In general, we find it convenient to carry out the reaction forming the active ester at a temperature of from −10° C. to 80° C. and that of the active ester with the amino compound at about room temperature. The time required for the reactions may also vary widely, depending on many factors, notably the reaction temperature and the nature of the reagents. However, provided that the reaction is effected under the preferred conditions outlined above, a period of from 30 minutes to 10 hours will usually suffice for each reaction.

The Mixed Acid Anhydride Method

A mixed acid anhydride of a compound of formula (IIIA) is prepared, and this is then reacted with the amino compound of formula (II).

The reaction for preparing the mixed acid anhydride may be carried out by reacting the acid compound of formula (IIIA) with a compound capable of forming a mixed acid anhydride, for example: a lower ($C_1$–$C_4$) alkyl halocarbonate, such as ethyl chlorocarbonate or isobutyl chlorocarbonate; a lower alkanoyl halide, such as pivaloyl chloride; a lower alkyl or diaryl cyanophosphate, such as diethyl cyanophosphate or diphenyl cyanophosphate. The reaction normally and preferably takes place in an inert solvent (e.g. the aforementioned halohydrocarbon, amide or ether).

The reaction is preferably carried out in the presence of an organic amine, such as triethylamine or N-methylmorpholine.

The reaction can take place over a wide range of temperatures, and the precise reaction temperature is not critical to the invention. In general, we find it convenient to carry out the reaction at a temperature of from −10° C. to 50° C. The time required for the reaction may also vary widely, depending on many factors, notably the reaction temperature and the nature of the reagents. However, provided that the reaction is effected under the preferred conditions outlined above, a period of from 30 minutes to 20 hours will usually suffice.

The reaction of the mixed acid anhydride thus prepared with the amine of formula (II) is preferably carried out in an inert solvent (e.g. the aforementioned amide or ether) in the presence of the aforementioned organic amine, at 0° C. to 80° C., at which it will usually require from 1 to 24 hours.

This reaction can also be effected by reacting simultaneously a compound of formula (IIIA), a compound of formula (II) and reagent capable of forming a mixed acid anhydride.

The Condensation Method

The condensation method may be carried out by directly reacting the compound of formula (IIIA) with an amino compound of formula (II) in the presence of a condensing agent, such as dicyclohexylcarbodiimide, carbonyldiimidazole or 1-methyl-2-chloropyridinium iodide-triethylamine. The reaction is carried out in a similar way to that used to prepare the active ester mentioned already.

Reaction B

Compounds of formula (I) wherein $R^3$ is $R^{3a}$ (in which $R^{3a}$ represents a substituted or unsubstituted alkyl group or an alkenyl group, as defined for $R^3$), i.e. a compound of formula (IB) can be also prepared by reacting a compound of formula (I) wherein $R^3$ represents a hydrogen atom, i.e. a compound of formula (IA), with a compound of formula (IIB):

$$R^{3a}-X \quad\quad (IIB)$$

(in which $R^{3a}$ is as defined above and X represents a halogen atom, preferably a chlorine, bromine or iodine atom):

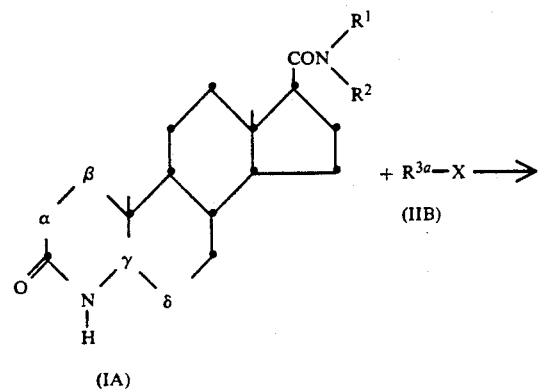

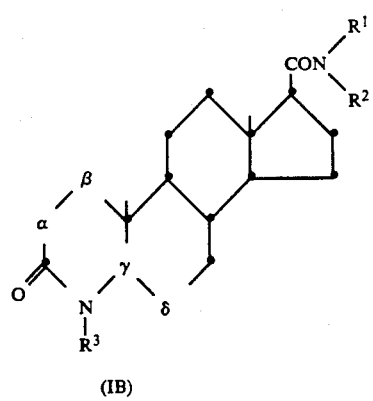

(in which $R^1$, $R^2$, $R^3$, $R^{3a}$, X, $\alpha$-$\beta$ and $\gamma$-$\delta$ are as defined above).

The reaction is normally and preferably carried out in an inert solvent and in the presence of a base.

Suitable bases which may be employed include: alkali metal hydrides, such as sodium hydride or potassium hydride; alkali metal alkoxides, such as sodium methoxide, sodium ethoxide or potassium t-butoxide; alkali metal hydroxides, such as sodium hydroxide or potassium hydroxide; and alkali metal carbonates, such as lithium carbonate, sodium carbonate or potassium carbonate; of these, we prefer the alkali metal hydrides.

There is no particular restriction on the nature of the solvent to be employed, provided that it has no adverse effect on the reaction or on the reagents involved and that it can dissolve the reagents, at least to some extent. Examples of suitable solvents include: water; alcohols, such as methanol or ethanol; ethers, such as diethyl ether or tetrahydrofuran; aromatic hydrocarbons, such as benzene, toluene or xylene; halogenated hydrocarbons, especially halogenated aliphatic hydrocarbons, such as methylene chloride or chloroform; ketones, such as acetone or methyl ethyl ketone; amides, especially fatty acid amides, such as dimethylformamide, dimethylacetamide or hexamethylphosphoric triamide; sulfoxides, such as dimethyl sulfoxide; and mixtures of any two or more of these solvents; of these, we prefer the amides. If necessary, by using a mixed solvent comprising an organic solvent and water, a two-phase reaction can be conducted in the presence of an ammonium salt, such as tetrabutylammonium hydrosulfite.

The reaction can take place over a wide range of temperatures, and the precise reaction temperature is not critical to the invention. In general, we find it convenient to carry out the reaction at a temperature of from $-50°$ C. to $150°$ C. (more preferably from $-10°$ C. to $100°$ C.). The time required for the reaction may also vary widely, depending on many factors, notably the reaction temperature and the nature of the reagents. However, provided that the reaction is effected under the preferred conditions outlined above, a period of from 30 minutes to 24 hours (more preferably from 1 hour to 10 hours) will usually suffice.

The starting material of formula (IIIA) is a known compound or can be prepared according to a known method [for example, *J. Med. Chem.* 27, 1690 (1984); *J. Med. Chem.* 29, 2298 (1986)].

The starting material of formula (II) is a known compound or can be prepared according to a known method [for example, *Synthesis*, 593 (1976); *J. Org. Chem.*, 36, 305 (1971); *Angew. Chem.*, 82, 138 (1970); *Synthesis,* 24 (1978); *Synthetic Commun.*, 18, 777 (1988); *Synthetic Commun.*, 18, 783 (1988); *Organic Reaction*, 3, 337 (1946); *Org. Synthesis,* 51, 48; *Tetrahedron*, 30, 2151 (1974); and *J. Org. Chem.*, 37, 188 (1972)].

Reaction C

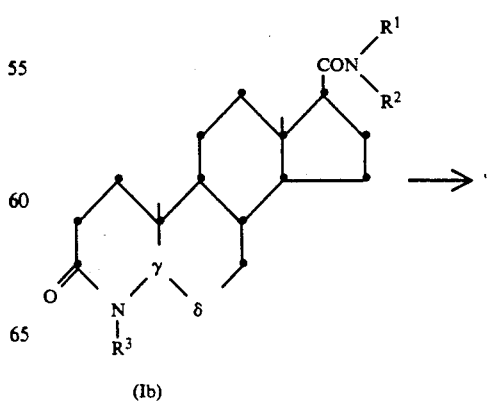

-continued

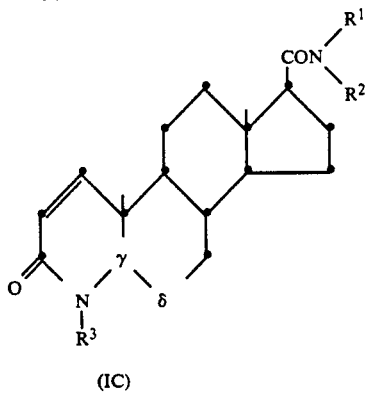

(IC)

(in which $R^1$, $R^2$, $R^3$ and γ-δ are as defined above).

In this reaction, a compound of formula (IC) [which is a compound of formula (I) in which the 1,2 bond is a double bond] is prepared by dehydrogenation of a compound of formula (Ib) in which the 1,2 bond is a single bond, using any of the following four methods.

(1) Dehydrogenation with 2,3-dichloro-5,6-dicyano-p-benzoquinone

The reaction of the compound of formula (Ib) with 2,3-dichloro-5,6-dicyano-p-benzoquinone can be carried out in an inert solvent and in the present of a silylating agent.

Examples of silylating agents include:
bis[(tri-$C_1$-$C_4$ alkyl)silyl]carboxylic amides, such as
N,O-bis(trimethylsilyl)acetamide,
N,O-bis(triethylsilyl)acetamide,
N,O-bis(tripropylsilyl)acetamide,
N,O-bis(tributylsilyl)acetamide,
N,O-bis(trimethylsilyl)trifluoroacetamide,
N,O-bis(triethylsilyl)trifluoroacetamide,
N,O-bis(tripropylsilyl)trifluoroacetamide,
N,O-bis(tributylsilyl)trifluoroacetamide,
N,O-bis(trimethylsilyl)pentafluoropropionylamide,
N,O-bis(triethylsilyl)pentafluoropropionylamide,
N,O-bis(tripropylsilyl)pentafluoropropionylamide,
N,O-bis(tributylsilyl)pentafluoropropionylamide,
N,O-bis(trimethylsilyl)trichloroacetamide,
N,O-bis(triethylsilyl)trichroroacetamide,
N,O-bis(tripropylsilyl)trichloroacetamide and
N,O-bis(tributylsilyl)trichloroacetamide,
preferably
N,O-bis(trimethylsilyl)trifluoroacetamide,
N,O-bis(triethylsilyl)trifluoroacetamide,
N,O-bis(trimethylsilyl)pentafluoropropionylamide and
N,O-bis(triethylsilyl)pentafluoropropionylamide,
and more preferably
N,O-bis(trimethylsilyl)trifluoroacetamide and
N,O-bis(triethylsilyl)trifluoroacetamide.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; hydrocarbons, which may be aliphatic or aromatic, such as hexane, benzene, toluene, xylene and cyclohexane; and halogenated hydrocarbons, especially halogenated aliphatic hydrocarbons, such as methylene chloride, chloroform and carbon tetrachloride. Of these, we prefer the ethers.

The reaction can take place over a wide range of temperature, and the precise reaction temperature is not critical to the invention. In general, we find it convenient to carry out the reaction at a temperature of from 0° C. to 150° C., more preferably from room temperature to 120° C. The time required for the reaction may also vary widely, depending on many factors, notably the reaction temperature and the nature of the reagents. However, provided that the reaction is effected under the preferred conditions outlined above, a period of from 1 hour to 24 hours, more preferably from 3 hours to 20 hours, will usually suffice.

(2) Dehydrogenation with benzeneseleninic anhydride

The oxidation of the compound of formula (Ib) can be carried out in an inert solvent in the presence of benzeneseleninic anhydride.

There is no particular restriction on the nature of the solvent, provided that it has no adverse effect on the reaction or on the reagents involved and that it can dissolve the reagents, at least to some extent. Examples of suitable solvents include: aromatic hydrocarbons and halogenated aromatic hydrocarbons, such as benzene, toluene, xylene, chlorobenzene and dichlorobenzene; dialkylamides, such as dimethylformamide and dimethylacetamide; and dialkyl sulfoxides such as dimethyl sulfoxide. Of these, we prefer the aromatic hydrocarbons.

The reaction can take place over a wide range of temperatures, and the precise reaction temperature is not critical to the invention. In general, we find it convenient to carry out the reaction at a temperature of from 50° C. to 250° C., more preferably from 100° C. to 200° C. The time required for the reaction may also vary widely, depending on many factors, notably the reaction temperature and the nature of the reagents. However, provided that the reaction is effected under the preferred conditions outlined above, a period of from 1 hour to 24 hours, preferably from 2 hours to 10 hours will usually suffice.

(3) Desulfinylation

This takes place in three steps:

(i) Reaction of Compound (Ib) with diaryl disulfide

This reaction can be carried out in an inert solvent in the present of a base.

Examples of suitable diaryl disulfides include diphenyl disulfide, ditolyl disulfide, di-p-chlorophenyl disulfide, di-p-methoxyphenyl disulfide and dinaphthyl disulfide, preferably diphenyl disulfide.

Examples of suitable bases include dialkyl lithium amides, such as diisopropyl lithium amide, dicyclohexyl lithium amide and isopropyl cyclohexyl lithium amide, preferably diisopropyl lithium amide.

There is no particular restriction on the nature of the solvent, provided that it has no adverse effect on the reaction or on the reagents involved and that it can dissolve the reagents, at least to some extent. Examples of suitable solvents include: ethers, such as diethyl ether, tetrahydrofuran and dioxane; and hydrocarbons, which may be aliphatic or aromatic, such as hexane, benzene, toluene, xylene and cyclohexane. Of these, we prefer the ethers.

The reaction can take place over a wide range of temperatures, and the precise reaction temperature is not critical to the invention. In general, we find it convenient to carry out the reaction at a temperature of from −78° C. to 50° C., more preferably from −30° C. to room temperature. The time required for the reaction may also vary widely, depending on many factors, notably the reaction temperature and the nature of the reagents. However, provided that the reaction is effected under the preferred conditions outlined above, a period of from 1 hour to 24 hours, more preferably from 3 hours to 20 hours, will usually suffice.

(ii) Oxidation of the Sulfide

The oxidation reaction of the sulfide prepared in step (i) can be carried out in an inert solvent in the presence of an oxidizing agent.

Examples of suitable oxidizing agents include: peracids, such as peracetic acid, perbenzoic acid, pertoluic acid and m-chloroperbenzoic acid; and alkali metal perhalogenates, such as sodium perchlorate, potassium perchlorate, sodium perbromate, lithium periodate, sodium periodate and potassium periodate. Of these, we prefer perbenzoic acid, m-chloroperbenzoic acid, sodium periodate and potassium periodate.

There is no particular restriction on the nature of the solvent, provided that it has no adverse effect on the reaction or on the reagents involved and that it can dissolve the reagents, at least to some extent. Examples of suitable solvents include: alcohols, such as methanol, ethanol, propanol and butanol; hydrocarbons, which may be aliphatic or aromatic, such as hexane, benzene, toluene, xylene and cyclohexane; and halogenated hydrocarbons, especially halogenated aliphatic hydrocarbons, such as methylene chloride, chloroform and carbon tetrachloride. Of these, we prefer the alcohols.

The reaction can take place over a wide range of temperatures, and the precise reaction temperature is not critical to the invention. In general, we find it convenient to carry out the reaction at a temperature of from −20° C. to 50° C., more preferably from 0° C. to room temperature. The time required for the reaction may also vary widely, depending on many factors, notably the reaction temperature and the nature of the reagents. However, provided that the reaction is effected under the preferred conditions outlined above, a period of from 1 hour to 24 hours, more preferably from 3 hours to 20 hours, will usually suffice.

(iii) Desulfinylation

This reaction can be carried out by heating the S-oxide prepared in step (ii) in an inert solvent and in the presence of an organic base.

There is no particular restriction on the nature of the solvent, provided that it has no adverse effect on the reaction or on the reagents involved and that it can dissolve the reagents, at least to some extent. Examples of suitable solvents include: aromatic hydrocarbons and halogenated aromatic hydrocarbons, such as benzene, toluene, xylene and chlorobenzene; dialkylamides, such as dimethylformamide and dimethylacetamide; and dialkyl sulfoxides, such as dimethyl sulfoxide. Of these, we prefer the aromatic and halogenated aromatic hydrocarbons.

Examples of bases are the same as are given in step (4)(i), hereafter.

The reaction can take place over a wide range of temperatures, and the precise reaction temperature is not critical to the invention. In general, we find it convenient to carry out the reaction at a temperature of from 50° C. to 250° C., more preferably from 100° C. to 200° C. The time required for the reaction may also vary widely, depending on many factors, notably the reaction temperature and the nature of the reagents. However, provided that the reaction is effected under the preferred conditions outlined above, a period of from 1 hour to 24 hours, more preferably from 3 hours to 20 hours, will usually suffice.

(4) De-hydrobromic acid method

This takes place in four steps:

(i) Reaction of Compound (Ib) with oxalyl halide

The reaction can be carried out in an inert solvent and in the present of an organic base.

Examples of suitable oxalyl halides include oxalyl chloride and oxalyl bromide, preferably oxalyl chloride.

Examples of suitable organic bases include triethylamine, diethylaniline, pyridine, 4-dimethylaminopyridine, 1,5-diazabicyclo[4.3.0]non-5-ene (DBN) and 1,8-diazabicyclo[5.4.0]undec-7-ene (DBU), preferably triethylamine, diethylaniline or pyridine.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; hydrocarbons, which may be aliphatic or aromatic, such as hexane, benzene, toluene, xylene and cyclohexane; and halogenated hydrocarbons, especially halogenated aliphatic hydrocarbons, such as methylene chloride, chloroform and carbon tetrachloride. Of these, we prefer the ethers.

The reaction can take place over a wide range of temperatures, and the precise reaction temperature is not critical to the invention. In general, we find it convenient to carry out the reaction at a temperature of from −20° C. to 100° C., more preferably from 0° C. to room temperature. The time required for the reaction may also vary widely, depending on many factors, notably the reaction temperature and the nature of the reagents. However, provided that the reaction is effected under the preferred conditions outlined above, a period of from 30 minutes to 10 hours, more preferably from 1 hour to 5 hours, will usually suffice.

(ii) Bromination of the Oxalate

The bromination of the oxalate prepared in step (i) can be carried out by reacting it with bromine in an inert solvent.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; hydrocarbons, which may be aliphatic or aromatic, such as hexane, benzene, toluene, xylene and cyclohexane; and halogenated hydrocarbons, especially halogenated aliphatic hydrocarbons, such as methylene chloride, chloroform and carbon tetrachloride. Of these, we prefer the halogenated hydrocarbons.

The reaction can take place over a wide range of temperatures, and the precise reaction temperature is not critical to the invention. In general, we find it convenient to carry out the reaction at a temperature of from −20° C. to 50° C., more preferably from 0° C. to room temperature. The time required for the reaction may also vary widely, depending on many factors, notably the reaction temperature and the nature of the reagents. However, provided that the reaction is effected under the preferred conditions outlined above, a period of from 30 minutes to 24 hours, more preferably from 1 hour to 10 hours, will usually suffice.

(iii) De-oxalylation

The reaction can be carried out in an inert solvent in the presence of ethylene diamine.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; hydrocarbons, which may be aliphatic or aromatic, such as hexane, benzene, toluene, xylene and cyclohexane; and halogenated hydrocarbons, such as methylene chloride, chloroform and carbon tetrachloride. Of these, we prefer the ethers.

The reaction can take place over a wide range of temperatures, and the precise reaction temperature is not critical to the invention. In general, we find it convenient to carry out the reaction at a temperature of from 0° C. to 200° C., more preferably from room temperature to 100° C. The time required for the reaction may also vary widely, depending on many factors, notably the reaction temperature and the nature of the reagents. However, provided that the reaction is effected under the preferred conditions outlined above, a period of from 30 minutes to 24 hours, more preferably from 1 hours to 10 hours, will usually suffice.

(iv) De-hydrobromination

The dehydrobromination of the bromide prepared in step (iii) can be carried out in an inert solvent in the present of an organic base.

Examples of suitable organic bases include triethylamine, diethylaniline, pyridine, 4-dimethylaminopyridine, 1,5-diazabicyclo[4.3.0]non-5-ene (DBN) and 1,8-diazabicyclo[5.4.0]undec-7-ene (DBU), preferably DBN or DBU.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran and dioxane; hydrocarbons, which may be aliphatic or aromatic, such as hexane, benzene, toluene, xylene and cyclohexane; and halogenated hydrocarbons, especially halogenated aliphatic hydrocarbons, such as methylene chloride, chloroform and carbon tetrachloride. Of these, we prefer the ethers or the hydrocarbons.

The reaction can take place over a wide range of temperatures, and the precise reaction temperature is not critical to the invention. In general, we find it convenient to carry out the reaction at a temperature of from −20° C. to 100° C., more preferably from 0° C. to 50° C. The time required for the reaction may also vary widely, depending on many factors, notably the reaction temperature and the nature of the reagents. However, provided that the reaction is effected under the preferred conditions outlined above, a period of from 30 minutes to 10 hours, more preferably from 1 hours to 5 hours, will usually suffice.

Reaction D

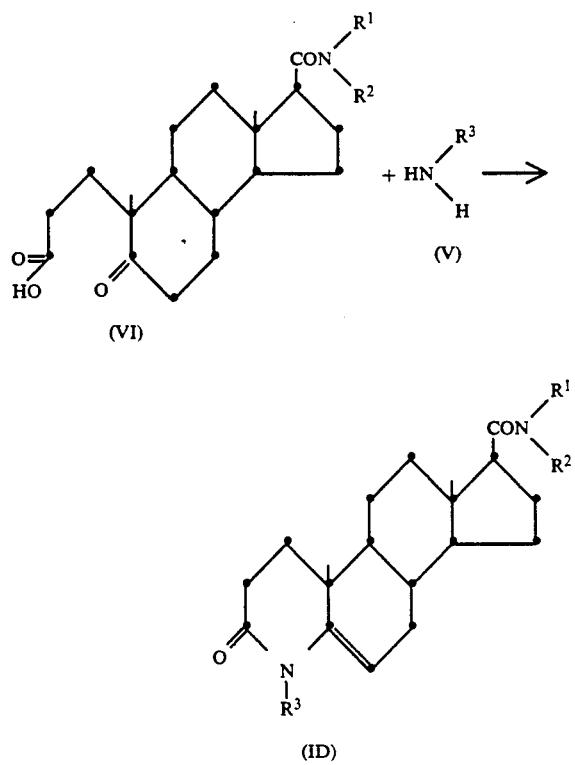

A compound of formula (ID), which is a compound of formula (I) wherein the 5,6 bond is a double bond, can be prepared by reaction of a compound of formula (VI) with an amino compound of formula (V) in an inert solvent.

There is no particular restriction on the nature of the solvent to be employed, provided that it has no adverse effect on the reaction or on the reagents involved and that it can dissolve the reagents, at least to some extent. Examples of suitable solvents include: glycols, such as ethylene glycol and propylene glycol; dialkylamides, such as dimethylformamide and dimethylacetamide; dialkyl sulfoxides, such as dimethyl sulfoxide; and ethers, such as ethylene glycol dimethyl ether, ethylene glycol diethyl ether, propylene glycol dimethyl ether and propylene glycol diethyl ether. Of these, we prefer the glycols.

The reaction can take place over a wide range of temperatures, and the precise reaction temperature is not critical to the invention. In general, we find it convenient to carry out the reaction at a temperature of from −10° C. to 220° C., preferably raising the temperature within the range from −10° C. to 150° C. for a period of from 2 hours to 5 hours and then keeping the mixture at a temperature from 150° C. to 220° C. for a period of from 10 minutes to 2 hours (preferably from 15 minutes to 1 hour).

The starting compound of formula (VI) can be prepared by reacting a compound of formula (VII):

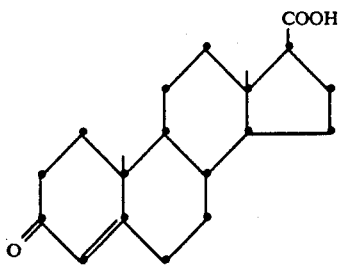

[which is described in *J. Med. Chem.*, 27, 1690–1701 (1984) and 29, 2298–2315 (1986)] with an amino compound of formula (II):

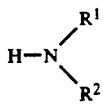

in a similar manner to that described in Reaction A, followed by oxidizing it in a similar manner to that described in *J. Med. Chem.*, 27, 1690–1701 (1984) and 29, 2298–2315 (1986).

After completion of each reaction step, the desired compound from that step can be obtained from the reaction mixture by conventional means. For example, in one suitable recovery procedure: the reaction mixture is suitably neutralized; insoluble matter, if any, is removed by filtration; the solvent is distilled off; and then the crystals which separate are removed by filtration, to give the desired compound; or the reaction mixture is diluted with water; extracted with a water-immiscible organic solvent; and the solvent is distilled off, to give the desired compound. If required, this can be further purified by conventional means, such as recrystallization, reprecipitation or the various chromatography techniques, notably column chromatography.

The azasteroid compounds of the present invention have a pronounced ability to inhibit testosterone 5α-reductase activity and have a low toxicity. They are therefore expected to be of value in the treatment and prophylaxis of prostatic hypertrophy.

For this purpose, they may, if required, be used in admixture with other active compounds and/or with common carriers, diluents, adjuvants and/or excipients, to form a pharmaceutical preparation. Alternatively, they may, if required, be administered alone. The form of the pharmaceutical preparation will, of course, depend upon the chosen route of administration, but, for oral administration, the compounds may, for example, be formulated as powders, granules, syrups, tablets or capsules; for parenteral administration, they may be formulated as injections, suppositories or inhalations. These preparations can be prepared according to the known means by addition of such additives as vehicles, binders, disintegrators, lubricants, stabilizers and corrigents. Although the dosage may vary depending upon the symptoms and age of the patient, the nature and severity of the disease or disorder and the route and manner of administration, in the case of oral administration to an adult human patient, they may normally be administered at a daily dose of from 1 to 1000 mg. The compounds may be administered in a single dose, or in divided doses, for example two or three times a day.

The preparation of the compounds of the present invention is further illustrated by the following non-limiting Examples, whilst the preparation of certain of the starting materials used in these Examples is illustrated by the subsequent Preparations.

EXAMPLE 1

N-(Diphenylmethyl)-3-oxo-4-aza-5α-androstane-17β-carboxamide 100 mg of 3-oxo-4-aza-5α-androstane-17β-carboxylic acid, 100 μl of diphenylmethylamine, 75 μl of diethyl cyanophosphate and 100 μl of triethylamine were added, in that order, to 5 ml of dry methylene chloride, and the reaction solution was allowed to stand overnight, whilst stirring, at room temperature. It was then diluted with 100 ml of methylene chloride, and washed with 1N aqueous hydrochloric acid, with water, with an aqueous solution of sodium hydrogencarbonate and with a saturated aqueous solution of sodium chloride, in that order, dried over anhydrous magnesium sulfate and condensed by distillation under reduced pressure. The resulting residue was purified by column chromatography through 15 g of silica gel. Gradient elution with mixtures of acetone and methylene chloride ranging from 1:9 to 1:1 by volume afforded 137 mg of the title compound.

Nuclear Magnetic Resonance Spectrum (CDCl$_3$), δ ppm:
0.67 (3H, singlet);
0.90 (3H, singlet);
0.70–2.00 (15H, multiplet);
2.15–2.30 (3H, multiplet);
2.37–2.47 (2H, multiplet);
3.03 (1H, doublet of doublets, J=10 & 5 Hz);
5.46 (1H, broad);
5.88 (1H, doublet, J=9 Hz);
6.28 (1H, doublet, J=9 Hz);
7.20–7.38 (10H, multiplet).

Infrared Absorption Spectrum (KBr), $v_{max}$ cm$^{-1}$: 3288, 2935, 2868, 1664, 1521, 1493, 1448, 1226, 733, 698.

EXAMPLE 2

N-(1,1-Diphenylethyl)-3-oxo-4-aza-5α-androstane-17β-carboxamide 150 mg of 3-oxo-4-aza-5α-androstane-17β-carboxylic acid, 250 μl of 1,1-diphenylethylamine, 150 mg of 2-chloro-1-methylpyridinium iodide and 150 μl of triethylamine were dissolved in 5 ml of dry acetonitrile, and the solution was heated for 3 hours under reflux. At the end of this time, the reaction solution was diluted with 100 ml of methylene chloride, washed with 1N aqueous hydrochloric acid, with water, with an aqueous solution of sodium bisulfate and with a saturated aqueous solution of sodium chloride solution, in that order, and dried over anhydrous magnesium sulfate; the solvent was then removed by distillation under reduced pressure. The resulting residue was purified by column chromatography through 15 g of silica gel. Gradient elution with mixtures of acetone and methylene chloride ranging from 1:9 to 1:1 by volume afforded 165 mg of the title compound.

Nuclear Magnetic Resonance Spectrum (CDCl$_3$), δ ppm:
0.70 (3H, singlet);
0.90 (3H, singlet);
2.20 (3H, singlet);
0.70–2.25 (17H, multiplet);
2.35–2.50 (3H, multiplet);

3.05 (1H, doublet of doublets, J=10 & 5 Hz);
5.44 (1H, broad);
5.98 (1H, broad);
7.20–7.40 (10H, multiplet).
Infrared Absorption Spectrum (KBr), $\nu_{max}$ cm$^{-1}$: 3300, 2937, 2869, 1665, 1491, 1446, 1360, 1226, 762, 699.

EXAMPLE 3

N-(1,2-Diphenylethyl)-3-oxo-4-aza-5α-androstane-17β-carboxamide

The title compound was prepared in a yield of 91% in a similar manner to that described in Example 1 by reacting 3-oxo-4-aza-5α-androstane-17β-carboxylic acid and 1,2-diphenylethylamine.

Nuclear Magnetic Resonance Spectrum (CDCl$_3$), δ ppm:
0.48 & 0.50 (total 3H, each singlet);
0.88 & 0.89 (total 3H, each singlet);
0.7–2.2 (18H, multiplet);
2.35–2.47 (2H, multiplet);
2.97–3.30 (3H, multiplet);
5.20–5.60 (3H, multiplet);
7.02–7.37 (10H, multiplet).

Infrared Absorption Spectrum (KBr), $\nu_{max}$ cm$^{-1}$: 3300, 2935, 1664, 1525, 1495, 1358, 1307, 1227, 755, 698.

EXAMPLE 4

N,N-Dibenzyl-3-oxo-4-aza-5α-androstane-17β-carboxamide

The title compound was prepared in a yield of 79% in a similar manner to that described in Example 1 by reacting 3-oxo-4-aza-5α-androstane-17β-carboxylic acid and N,N-dibenzylamine.

Nuclear Magnetic Resonance Spectrum (CDCl$_3$), δ ppm:
0.89 (3H, singlet);
0.91 (3H, singlet);
0.7–1.9 (17H, multiplet);
2.3–2.5 (2H, multiplet);
2.73 (1H, triplet, J=8 Hz);
3.03 (1H, doublet of doublets, J=10 & 5 Hz);
3.73 (1H, doublet, J=15 Hz);
4.16 (1H, doublet, J=16 Hz);
4.91 (1H, doublet, J=16 Hz);
5.40 (1H, broad);
5.45 (1H, doublet, J=15 Hz);
7.20–7.32 (10H, multiplet).

Infrared Absorption Spectrum (KBr), $\nu_{max}$ cm$^{-1}$: 3196, 2933, 1669, 1633, 1444, 1359, 1306, 1218, 755, 703.

EXAMPLE 5

N-(2,2-Diphenylethyl)-3-oxo-4-aza-5α-androstane-17β-carboxamide

The title compound was prepared in a yield of 81% in a similar manner to that described in Example 1 by reacting 3-oxo-4-aza-5α-androstane-17β-carboxylic acid and 2,2-diphenylethylamine.

Nuclear Magnetic Resonance Spectrum (CDCl$_3$), δ ppm:
0.54 (3H, singlet);
0.88 (3H, singlet);
0.63–2.20 (17H, multiplet);
2.36–2.54 (2H, multiplet);
3.00 (1H, doublet of doublets, J=11 & 5 Hz);
3.48 (1H, doublet, J=5 Hz);
3.74 (1H, doubled doublet of doublets, J=15, 10 & 5 Hz);
4.07 (1H, doubled doublet of doublets, J=15, 10 & 5 Hz);
4.21 (1H, triplet, J=10 Hz);
5.20 (1H, broad triplet, J=5 Hz);
5.42 (1H, broad);
7.18–7.37 (10H, multiplet).

Infrared Absorption Spectrum (KBr), $\nu_{max}$ cm$^{-1}$: 3282, 3189, 2934, 1662, 1494, 1449, 1357, 1229, 735, 701.

EXAMPLE 6

N-(3,3-Diphenylpropyl)-3-oxo-4-aza-5α-androstane-17β-carboxamide

The title compound was prepared in a yield of 95% in a similar manner to that described in Example 1 by reacting 3-oxo-4-aza-5α-androstane-17β-carboxylic acid and 3,3-diphenylpropylamine.

Nuclear Magnetic Resonance Spectrum (CDCl$_3$), δ ppm:
0.66 (3H, singlet);
0.90 (3H, singlet);
0.70–2.20 (18H, multiplet);
2.22–2.34 (2H, multiplet);
2.36–2.47 (2H, multiplet);
3.05 (1H, doublet of doublets, J=10 & 5 Hz);
3.25 (2H, multiplet);
3.96 (1H, triplet, J=8 Hz);
5.20 (1H, broad triplet, J=6 Hz);
5.47 (1H, broad);
7.13–7.35 (10H, multiplet).

Infrared Absorption Spectrum (KBr), $\nu_{max}$ cm$^{-1}$: 3305, 2935, 2869, 1662, 1532, 1449, 1359, 1307, 1227, 750, 701.

EXAMPLE 7

N-(Diphenylmethyl)-3-oxo-4-aza-5α-androst-1-ene-17β-carboxamide

The title compound was prepared in a yield of 54% in a similar manner to that described in Example 1 by reacting 3-oxo-4-aza-5α-androst-1-ene-17β-carboxylic acid and diphenylmethylamine.

Nuclear Magnetic Resonance Spectrum (CDCl$_3$), δ ppm:
0.69 (3H, singlet);
0.97 (3H, singlet);
0.80–2.30 (16H, multiplet);
3.31 (1H, triplet, J=10 Hz);
5.30 (1H, broad);
5.80 (1H, doublet, J=9 Hz);
5.89 (1H, doublet, J=8 Hz);
6.28 (1H, doublet, J=8 Hz);
6.77 (1H, doublet, J=9 Hz);
7.10–7.40 (10H, multiplet).

Infrared Absorption Spectrum (KBr), $\nu_{max}$ cm$^{-1}$: 2935, 1676, 1600, 1518, 1493, 1448, 698.

EXAMPLE 8

N-(1,2-Diphenylethyl)-3-oxo-4-aza-5α-androst-1-ene-17β-carboxamide

The title compound was prepared in a yield of 87% in a similar manner to that described in Example 1 by reacting 3-oxo-4-aza-5α-androst-1-ene-17β-carboxylic acid and 1,2-diphenylethylamine.

Nuclear Magnetic Resonance Spectrum (CDCl$_3$), δ ppm:

0.47 & 0.51 (total 3H, each singlet);
0.93 & 0.95 (total 3H, each singlet);
0.90–2.20 (16H, multiplet);
2.95–3.20 (2H, multiplet);
3.30 (1H, triplet, J=9 Hz);
5.10–5.40 (2H, multiplet);
5.49 & 5.58 (total 1H, each doublet, J=8 Hz);
5.80 (1H, multiplet);
6.78 (1H, multiplet);
7.00–7.40 (10H, multiplet).

Infrared Absorption Spectrum (KBr), $\nu_{max}$ cm$^{-1}$: 2968, 2937, 1675, 1601, 1525, 1495, 1452, 816, 698.

EXAMPLE 9

N,N-Dibenzyl-3-oxo-4-aza-5α-androst-1-ene-17β-carboxamide

The title compound was prepared in a yield of 58% in a similar manner to that described in Example 1 by reacting 3-oxo-4-aza-5α-androst-1-ene-17β-carboxylic acid and N,N-dibenzylamine.

Nuclear Magnetic Resonance Spectrum (CDCl$_3$), δ ppm:
0.90 (3H, singlet);
0.99 (3H, singlet);
0.90–1.95 (14H, multiplet);
2.40 (1H, quartet, J=10 Hz);
2.76 (1H, triplet, J=9 Hz);
3.30 (1H, triplet, J=9 Hz);
3.77 (1H, doublet, J=14 Hz);
4.18 (1H, doublet, J=16 Hz);
4.90 (1H, doublet, J=16 Hz);
5.29 (1H, broad);
5.45 (1H, doublet, J=14 Hz);
5.80 (1H, doublet, J=10 Hz);
6.74 (1H, doublet, J=10 Hz);
7.00–7.40 (10H, multiplet).

Infrared Absorption Spectrum (KBr), $\nu_{max}$ cm$^{-1}$: 2938, 1682, 1636, 1444, 1423, 699.

EXAMPLE 10

N-(2,2-Diphenylethyl)-3-oxo-4-aza-5α-androst-1-ene-17β-carboxamide

The title compound was prepared in a yield of 90% in a similar manner to that described in Example 1 by reacting 3-oxo-4-aza-5α-androst-1-ene-17β-carboxylic acid and 2,2-diphenylethylamine.

Nuclear Magnetic Resonance Spectrum (CDCl$_3$), δ ppm:
0.56 (3H, singlet);
0.95 (3H, singlet);
0.80–2.20 (16H, multiplet);
3.29 (1H, triplet, J=9 Hz);
3.74 (1H, multiplet);
4.08 (1H, multiplet);
4.21 (1H, triplet, J=8 Hz);
5.21 (1H, broad triplet);
5.31 (1H, broad);
5.80 (1H, doublet, J=10 Hz);
6.76 (1H, doublet, J=10 Hz);
7.10–7.40 (10H, multiplet).

Infrared Absorption Spectrum (KBr), $\nu_{max}$ cm$^{-1}$: 3296, 2933, 1675, 1600, 1517, 1494, 1450, 1226, 816, 700.

EXAMPLE 11

N-(Diphenylmethyl)-3-oxo-4-azaandrost-5-ene-17β-carboxamide

The title compound was prepared in a yield of 59% in a similar manner to that described in Example 1 by reacting 3-oxo-4-azaandrost-5-ene-17β-carboxylic acid and diphenylmethylamine.

Nuclear Magnetic Resonance Spectrum (CDCl$_3$), δ ppm:
0.71 (3H, singlet);
1.10 (3H, singlet);
1.00–2.00 (16H, multiplet);
2.40–2.55 (2H, multiplet);
4.79 (1H, multiplet);
5.89 (1H, doublet, J=9 Hz);
6.28 (1H, doublet, J=9 Hz);
7.16 (1H, broad);
7.18–7.40 (10H, multiplet).

Infrared Absorption Spectrum (KBr), $\nu_{max}$ cm$^{-1}$: 1661, 1485, 1400, 700.

EXAMPLE 12

N-(1,2-Diphenylethyl)-3-oxo-4-azaandrost-5-ene-17β-carboxamide

The title compound was prepared in a yield of 68% in a similar manner to that described in Example 1 by reacting 3-oxo-4-azaandrost-5-ene-17β-carboxylic acid and 1,2-diphenylethylamine.

Nuclear Magnetic Resonance Spectrum (CDCl$_3$), δ ppm:
0.50 & 0.53 (total 3H, each singlet);
1.07 & 1.09 (total 3H, each singlet);
1.00–2.30 (16H, multiplet);
2.40–2.60 (2H, multiplet);
2.98–3.22 (2H, multiplet);
4.78 (1H, multiplet);
5.23–5.40 (1H, multiplet);
5.50 & 5.60 (total 1H, each doublet, J=9 Hz);
7.00–7.40 (11H, multiplet).

Infrared Absorption Spectrum (KBr), $\nu_{max}$ cm$^{-1}$: 3186, 2942, 1662, 1604, 1492, 1386, 1221, 758, 699.

EXAMPLE 13

N,N-Dibenzyl-3-oxo-4-azaandrost-5-ene-17β-carboxamide

The title compound was prepared in a yield of 71% in a similar manner to that described in Example 1 by reacting 3-oxo-4-azaandrost-5-ene-17β-carboxylic acid and N,N-dibenzylamine.

Nuclear Magnetic Resonance Spectrum (CDCl$_3$), δ ppm:
0.93 (3H, singlet);
1.12 (3H, singlet);
1.00–2.50 (17H, multiplet);
2.76 (1H, triplet, J=9 Hz);
3.75 (1H, doublet, J=14 Hz);
4.17 (1H, doublet, J=16 Hz);
4.79 (1H, multiplet);
4.92 (1H, doublet, J=16 Hz);
5.46 (1H, doublet, J=14 Hz);
7.00–7.45 (11H, multiplet).

Infrared Absorption Spectrum (KBr), $\nu_{max}$ cm$^{-1}$: 3200, 2936, 1729, 1664, 1360, 1193, 1182, 1155.

EXAMPLE 14

N-(1,1-Dimethyl-2-phenylethyl)-3-oxo-4-aza-5α-androstane-17β-carboxamide

The title compound was prepared in a yield of 12% in a similar manner to that described in Example 2 by reacting 3-oxo-4-aza-5α-androstane-17β-carboxylic acid and 1,1-dimethyl-2-phenylethylamine.

Nuclear Magnetic Resonance Spectrum (CDCl$_3$), δ ppm:
0.70 (3H, singlet);
0.90 (3H, singlet);
1.27 (3H, singlet);
1.43 (3H, singlet);
0.75–2.30 (16H, multiplet);
2.37–2.50 (2H, multiplet);
2.83 (1H, doublet, J=13 Hz);
3.05 (1H, doublet of doublets, J=10 & 5 Hz);
3.20 (1H, doublet, J=13 Hz);
4.95 (1H, broad);
5.53 (1H, broad);
7.10–7.35 (5H, multiplet).

Infrared Absorption Spectrum (KBr), ν$_{max}$ cm$^{-1}$: 2937, 2869, 1666, 1502, 1452, 1385, 1360, 1307, 1229, 727, 702.

EXAMPLE 15

N-(1,1-Dimethyl-2-phenylethyl)-3-oxo-4-aza-5α-androst-1-ene-17β-carboxamide

The title compound was prepared in a yield of 48% in a similar manner to that described in Example 2 by reacting 3-oxo-4-aza-5α-androst-1-ene-17β-carboxylic acid and 1,1-dimethyl-2-phenylethylamine.

Nuclear Magnetic Resonance Spectrum (CDCl$_3$), δ ppm:
0.70 (3H, singlet);
0.96 (3H, singlet);
1.27 (3H, singlet);
1.44 (3H, singlet);
0.90–2.25 (16H, multiplet);
2.82 (1H, doublet, J=13 Hz);
3.20 (1H, doublet, J=13 Hz);
3.32 (1H, triplet, J=9 Hz);
4.97 (1H, broad);
5.40 (1H, broad);
5.80 (1H, doublet of doublets, J=10 & 1 Hz);
6.77 (1H, doublet, J=10 Hz);
7.10–7.35 (5H, multiplet).

Infrared Absorption Spectrum (KBr), ν$_{max}$ cm$^{-1}$: 2968, 2933, 1678, 1600, 1503, 1452, 1362, 702.

EXAMPLE 16

N-Benzyl-N-isopropyl-3-oxo-4-aza-5α-androstane-17β-carboxamide

The title compound was prepared in a yield of 70% in a similar manner to that described in Example 2 by reacting 3-oxo-4-aza-5α-androstane-17β-carboxylic acid and N-benzyl-N-isopropylamine.

Nuclear Magnetic Resonance Spectrum (CDCl$_3$), δ ppm:
0.70–2.90 (32H, multiplet);
3.02 (1H, multiplet);
4.20 & 4.29 (total 1H, each doublet, J=15 & 17 Hz);
4.40 & 4.96 (total 1H, each septet, J=7 Hz);
4.82 & 4.84 (total 1H, each doublet, J=17 & 15 Hz);
5.40 (1H, broad);
7.10–7.40 (5H, multiplet).

Infrared Absorption Spectrum (KBr), ν$_{max}$ cm$^{-1}$: 2970, 2937, 1668, 1640, 1451, 1418, 1388, 1360, 1307, 732.

EXAMPLE 17

N-Benzyl-N-isopropyl-3-oxo-4-aza-5α-androst-1-ene-17β-carboxamide

The title compound was prepared in a yield of 40% in a similar manner to that described in Example 2 by reacting 3-oxo-4-aza-5α-androst-1-ene-17β-carboxylic acid and N-benzyl-N-isopropylamine.

Nuclear Magnetic Resonance Spectrum (CDCl$_3$), δ ppm:
0.70–2.40 (27H, multiplet);
2.48 & 2.84 (total 1H, each triplet, J=9 Hz);
3.23–3.40 (1H, multiplet);
4.22 & 4.30 (total 1H, each doublet, J=15 & 17 Hz);
4.40 & 4.95 (total 1H, each septet, J=7 Hz);
4.80 & 4.83 (total 1H, each doublet, J=17 & 15 Hz);
5.30 (1H, broad);
5.80 (1H, multiplet);
6.75 & 6.78 (total 1H, each doublet, J=9 Hz);
7.10–7.40 (5H, multiplet).

Infrared Absorption Spectrum (KBr), ν$_{max}$ cm$^{-1}$: 3197, 2971, 2934, 1681, 1636, 1602, 1450, 1417, 1366, 1180, 817, 697.

EXAMPLE 18

N-(1,1-Diphenylethyl)-3-oxo-4-aza-5α-androst-1-ene-17β-carboxamide

The title compound was prepared in a yield of 32% in a similar manner to that described in Example 2 by reacting 3-oxo-4-aza-5α-androst-1-ene-17β-carboxylic acid and 1,1-diphenylethylamine.

Nuclear Magnetic Resonance Spectrum (CDCl$_3$), δ ppm:
0.70 (3H, singlet);
0.98 (3H, singlet);
0.90–2.30 (16H, multiplet);
2.20 (3H, singlet);
3.33 (1H, triplet, J=9 Hz);
5.32 (1H, broad);
5.80 (1H, doublet, J=10 Hz);
5.98 (1H, singlet);
6.78 (1H, doublet, J=10 Hz);
7.10–7.40 (10H, multiplet).

Infrared Absorption Spectrum (KBr), ν$_{max}$ cm$^{-1}$: 2968, 2935, 1678, 1600, 1491, 1446, 1365, 761, 699.

EXAMPLE 19

N-(1,1-Diphenylethyl)-3-oxo-4-azaandrost-5-ene-17β-carboxamide

The title compound was prepared in a yield of 55% in a similar manner to that described in Example 2 by reacting 3-oxo-4-azaandrost-5-ene-17β-carboxylic acid and 1,1-diphenylethylamine.

Nuclear Magnetic Resonance Spectrum (CDCl$_3$), δ ppm:
0.73 (3H, singlet);
1.11 (3H, singlet);
1.00–2.30 (16H, multiplet);
2.20 (3H, singlet);
2.40–2.55 (2H, multiplet);
4.80 (1H, multiplet);
5.98 (1H, broad);

7.10–7.40 (11H, multiplet).

Infrared Absorption Spectrum (KBr), $\nu_{max}$ cm$^{-1}$: 2943, 1681, 1667, 1487, 1447, 1386, 699.

EXAMPLE 20

N-(Diphenylmethyl)-4-methyl-3-oxo-4-aza-5α-androstane-17β-carboxamide 300 mg of N-(diphenylmethyl)-3-oxo-4-aza-5α-androstane-17β-carboxamide (prepared as described in Example 1) were dissolved in 4 ml of dry dimethylformamide, and 40 mg of sodium hydride (as a 55% w/w suspension in mineral oil) were added to the resulting solution. The mixture was then stirred for 30 minutes at room temperature, and then 0.5 ml of methyl iodide was added dropwise to it at room temperature; the mixture was then stirred again for 2 hours at 70° C. At the end of this time, the reaction solution was diluted with 200 ml of diethyl ether, washed three times with water and then with a saturated aqueous solution of sodium chloride, and dried over anhydrous magnesium sulfate. The solvent was then removed by distillation under reduced pressure. The resulting residue was purified by column chromatography through 15 g of silica gel. Gradient elution with mixtures of acetone and methylene chloride ranging from 1:20 to 1:4 by volume afforded 106 mg of the title compound.

Nuclear Magnetic Resonance Spectrum (CDCl$_3$), δ ppm:
  0.67 (3H, singlet);
  0.88 (3H, singlet);
  0.70–2.50 (20H, multiplet);
  2.93 (3H, singlet);
  3.02 (1H, doublet of doublets, J=12 & 2 Hz);
  5.88 (1H, doublet, J=8 Hz);
  6.29 (1H, doublet, J=8 Hz);
  7.10–7.45 (10H, multiplet).

Infrared Absorption Spectrum (KBr), $\nu_{max}$ cm$^{-1}$: 3296, 2937, 1665, 1619, 1528, 1493, 1446, 1397, 1304, 1218, 699.

EXAMPLE 21

N-(Diphenylmethyl)-4-ethyl-3-oxo-4-aza-5α-androstane-17β-carboxamide

The title compound was prepared in a yield of 87% in a similar manner to that described in Example 20 by reacting N-(diphenylmethyl)-3-oxo-4-aza-5α-androstane-17β-carboxamide (prepared as described in Example 1) and ethyl iodide.

Nuclear Magnetic Resonance Spectrum (CDCl$_3$), δ ppm:
  0.68 (3H, singlet);
  0.88 (3H, singlet);
  1.05 (3H, triplet, J=8 Hz);
  0.60–2.50 (20H, multiplet);
  3.08 (1H, doublet of doublets, J=11 & 2 Hz);
  3.25 (1H, multiplet);
  3.74 (1H, multiplet);
  5.88 (1H, doublet, J=8 Hz);
  6.28 (1H, doublet, J=8 Hz);
  7.10–7.40 (10H, multiplet).

Infrared Absorption Spectrum (KBr), $\nu_{max}$ cm$^{-1}$: 3292, 2936, 1671, 1619, 1530, 1447, 1224, 698.

EXAMPLE 22

N-(Diphenylmethyl)-4-allyl-3-oxo-4-aza-5α-androstane-17β-carboxamide

The title compound was prepared in a yield of 47% in a similar manner to that described in Example 20 by reacting N-(diphenylmethyl)-3-oxo-4-aza-5α-androstane-17β-carboxamide (prepared as described in Example 1) and allyl bromide.

Nuclear Magnetic Resonance Spectrum (CDCl$_3$), δ ppm:
  0.67 (3H, singlet);
  0.90 (3H, singlet);
  0.70–2.40 (18H, multiplet);
  3.11 (1H, doublet of doublets, J=10 & 3 Hz);
  3.80 (1H, doublet of doublets, J=16 & 5 Hz);
  4.43 (1H, multiplet);
  5.08 (1H, multiplet);
  5.12 (1H, multiplet);
  5.76 (1H, multiplet);
  5.87 (1H, doublet, J=9 Hz);
  6.28 (1H, doublet, J=9 Hz);
  7.15–7.40 (10H, multiplet).

Infrared Absorption Spectrum (KBr), $\nu_{max}$ cm$^{-1}$: 3304, 2936, 1667, 1647, 1624, 1531, 1444, 1223, 698.

EXAMPLE 23

N-(Diphenylmethyl)-4-benzyl-3-oxo-4-aza-5α-androstane-17β-carboxamide

The title compound was prepared in a yield of 55% in a similar manner to that described in Example 20 by reacting N-(diphenylmethyl)-3-oxo-4-aza-5α-androstane-17β-carboxamide (prepared as described in Example 1) and benzyl bromide.

Nuclear Magnetic Resonance Spectrum (CDCl$_3$), δ ppm:
  0.65 (3H, singlet);
  0.93 (3H, singlet);
  0.70–2.30 (18H, multiplet);
  2.55–2.65 (2H, multiplet);
  3.10 (1H, doublet of doublets, J=11 & 3 Hz);
  4.45 (1H, doublet, J=16 Hz);
  5.03 (1H, doublet, J=16 Hz);
  5.85 (1H, doublet, J=9 Hz);
  6.27 (1H, doublet, J=9 Hz);
  7.10–7.40 (15H, multiplet).

Infrared Absorption Spectrum (KBr), $\nu_{max}$ cm$^{-1}$: 3310, 3027, 2941, 1643, 1519, 1494, 1451, 1409, 1304, 1226, 699.

EXAMPLE 24

N-(Diphenylmethyl)-4-methyl-3-oxo-4-aza-5α-androst-1-ene-17β-carboxamide

The title compound was prepared in a yield of 83% in a similar manner to that described in Example 1 by reacting 4-methyl-3-oxo-4-aza-5α-androst-1-ene-17β-carboxylic acid (prepared as described in Preparation 4) and diphenylmethylamine.

Nuclear Magnetic Resonance Spectrum (CDCl$_3$), δ ppm:
  0.69 (3H, singlet);
  0.92 (3H, singlet);
  0.80–2.30 (16H, multiplet);
  2.95 (3H, singlet);
  3.35 (1H, doublet of doublets, J=13 & 4 Hz);
  5.86 (1H, doublet, J=8 Hz);

5.88 (1H, doublet, J=8 Hz);
6.28 (1H, doublet, J=8 Hz);
6.67 (1H, doublet, J=10 Hz);
7.20–7.40 (10H, multiplet).

Infrared Absorption Spectrum (KBr), $\nu_{max}$ cm$^{-1}$: 2966, 2940, 1663, 1602, 1519, 1494, 1448, 1394, 1221, 698.

EXAMPLE 25

N-(Diphenylmethyl)-4-methyl-3-oxo-4-azaandrost-5-ene-17β-carboxamide

The title compound was prepared in a yield of 82% in a similar manner to that described in Example 1 by reacting 4-methyl-3-oxo-4-azaandrost-5-ene-17β-carboxylic acid (prepared as described in Preparation 5) and diphenylmethylamine.

Nuclear Magnetic Resonance Spectrum (CDCl₃), δ ppm:
0.70 (3H, singlet);
1.05 (3H, singlet);
0.80–2.35 (16H, multiplet);
2.45–2.57 (2H, multiplet);
3.12 (3H, singlet);
5.04 (1H, multiplet);
5.89 (1H, doublet, J=9 Hz);
6.29 (1H, doublet, J=9 Hz);
7.10–7.40 (10H, multiplet).

Infrared Absorption Spectrum (KBr), $\nu_{max}$ cm$^{-1}$: 3314, 2944, 1669, 1642, 1627, 1524, 1494, 1385, 1124, 1054, 699.

EXAMPLE 26

N-(1,1-Diphenylethyl)-4-methyl-3-oxo-4-aza-5α-androstane-17β-carboxamide

The title compound was prepared in a yield of 65% in a similar manner to that described in Example 2 by reacting 4-methyl-3-oxo-4-aza-5α-androstane-17β-carboxylic acid (prepared as described in Preparation 2) and 1,1-diphenylethylamine.

Nuclear Magnetic Resonance Spectrum (CDCl₃), δ ppm:
0.70 (3H, singlet);
0.90 (3H, singlet);
0.70–2.30 (18H, multiplet);
2.20 (3H, multiplet);
2.48 (2H, multiplet);
2.94 (3H, singlet);
3.04 (1H, doublet of doublets, J=13 & 4 Hz);
5.97 (1H, broad);
7.20–7.40 (10H, multiplet).

Infrared Absorption Spectrum (KBr), $\nu_{max}$ cm$^{-1}$: 2940, 2872, 1681, 1643, 1492, 1446, 1392, 1228, 762, 699.

EXAMPLE 27

N-(1,1-Diphenylethyl)-4-methyl-3-oxo-4-aza-5α-androst-1-ene-17β-carboxamide

The title compound was prepared in a yield of 44% in a similar manner to that described in Example 2 by reacting 4-methyl-3-oxo-4-aza-5α-androst-1-ene-17β-carboxylic acid (prepared as described in Preparation 4) and 1,1-diphenylethylamine.

Nuclear Magnetic Resonance Spectrum (CDCl₃), δ ppm:
0.70 (3H, singlet);
0.93 (3H, singlet);
0.90–2.30 (16H, multiplet);
2.20 (3H, singlet);
2.96 (3H, singlet);
3.35 (1H, doublet of doublets, J=13 & 4 Hz);
5.90 (1H, doublet, J=10 Hz);
5.98 (1H, broad);
6.69 (1H, doublet, J=10 Hz);
7.20–7.40 (10H, multiplet).

Infrared Absorption Spectrum (KBr), $\nu_{max}$ cm$^{-1}$: 2940, 1663, 1604, 1492, 1446, 699.

EXAMPLE 28

N-(1,1-Diphenylethyl)-4-methyl-3-oxo-4-azaandrost-5-ene-17β-carboxamide

The title compound was prepared in a yield of 61% in a similar manner to that described in Example 2 by reacting 4-methyl-3-oxo-4-azaandrost-5-ene-17β-carboxylic acid (prepared as described in Preparation 5) and 1,1-diphenylethylamine.

Nuclear Magnetic Resonance Spectrum (CDCl₃), δ ppm:
0.73 (3H, singlet);
1.06 (3H, singlet);
1.00–2.35 (16H, multiplet);
2.20 (3H, singlet);
3.13 (3H, singlet);
5.04 (1H, multiplet);
5.98 (1H, broad);
7.20–7.40 (10H, multiplet).

Infrared Absorption Spectrum (KBr), $\nu_{max}$ cm$^{-1}$: 2966, 2943, 1670, 1641, 1492, 1447, 1388, 1324, 1241, 699.

EXAMPLE 29

N-(1,2-Diphenylethyl)-4-methyl-3-oxo-4-aza-5α-androstane-17β-carboxamide

The title compound was prepared in a yield of 75% in a similar manner to that described in Example 1 by reacting 4-methyl-3-oxo-4-aza-5α-androstane-17β-carboxylic acid (prepared as described in Preparation 2) and 1,2-diphenylethylamine.

Nuclear Magnetic Resonance Spectrum (CDCl₃), δ ppm:
0.46 & 0.50 (total 3H, each singlet);
0.85 & 0.86 (total 3H, each singlet);
0.60–2.50 (20H, multiplet);
2.91 (3H, singlet);
2.85–3.20 (3H, multiplet);
5.26 & 5.33 (total 1H, each doublet of doublets, J=8 & 7 Hz);
5.47 & 5.57 (total 1H, each doublet, J=8 Hz);
7.00–7.40 (10H, multiplet).

Infrared Absorption Spectrum (KBr), $\nu_{max}$ cm$^{-1}$: 3314, 2937, 2870, 1644, 1529, 1453, 1393, 1305, 1228, 699.

EXAMPLE 30

N-(1,2-Diphenylethyl)-4-methyl-3-oxo-4-aza-5α-androst-1-ene-17β-carboxamide

The title compound was prepared in a yield of 78% in a similar manner to that described in Example 1 by reacting 4-methyl-3-oxo-4-aza-5α-androst-1-ene-17β-carboxylic acid (prepared as described in Preparation 4) and 1,2-diphenylethylamine.

Nuclear Magnetic Resonance Spectrum (CDCl₃), δ ppm:
0.48 & 0.52 (total 3H, each singlet);

0.90 & 0.91 (total 3H, each singlet);
0.80–2.20 (16H, multiplet);
2.95 (3H, singlet);
2.90–3.24 (2H, multiplet);
3.33 (1H, doublet, J=13 Hz);
5.27 & 5.34 (total 1H, each doublet of doublets, J=8 & 7 Hz);
5.48 & 5.58 (total 1H, each doublet, J=8 Hz);
5.87 & 5.89 (total 1H, each doublet, J=10 Hz);
6.67 & 6.69 (total 1H, each doublet, J=10 Hz);
7.00–7.40 (10H, multiplet).

Infrared Absorption Spectrum (KBr), $\nu_{max}$ cm$^{-1}$: 3320, 2939, 1659, 1602, 1526, 1226, 699.

EXAMPLE 31

N-(1,2-Diphenylethyl)-4-methyl-3-oxo-4-azaandrost-5-ene-17β-carboxamide

The title compound was prepared in a yield of 78% in a similar manner to that described in Example 1 by reacting 4-methyl-3-oxo-4-azaandrost-5-ene-17β-carboxylic acid (prepared as described in Preparation 5) and 1,2-diphenylethylamine.

Nuclear Magnetic Resonance Spectrum (CDCl$_3$), δ ppm:
0.49 & 0.53 (total 3H, each singlet);
1.02 & 1.03 (total 3H, each singlet);
0.85–2.63 (18H, multiplet);
3.12 (3H, singlet);
2.95–3.25 (2H, multiplet);
5.02 (1H, multiplet);
5.27 & 5.34 (total 1H, each doublet of doublets, J=8 & 7 Hz);
5.50 & 5.59 (total 1H, each doublet, J=8 Hz);
7.00–7.38 (10H, multiplet).

Infrared Absorption Spectrum (KBr), $\nu_{max}$ cm$^{-1}$: 2944, 2871, 1669, 1642, 1524, 1495, 1453, 1387, 1243, 699.

EXAMPLE 32

N-[(S)-1,2-Diphenylethyl]-3-oxo-4-aza-5α-androstane-17β-carboxamide

The title compound was prepared in a yield of 96% in a similar manner to that described in Example 1 by reacting 3-oxo-4-aza-5α-androstane-17β-carboxylic acid and (S)-1,2-diphenylethylamine.

Nuclear Magnetic Resonance Spectrum (CDCl$_3$), δ ppm:
0.50 (3H, singlet);
0.87 (3H, singlet);
0.70–3.20 (23H, multiplet);
5.26 (1H, quartet, J=5 Hz);
5.47 (1H, broad);
5.58 (1H, doublet, J=5 Hz);
7.00–7.40 (10H, multiplet).

Infrared Absorption Spectrum (KBr), $\nu_{max}$ cm$^{-1}$: 2938, 2872, 1663, 1497, 1453, 1360, 1308, 1230, 699.

EXAMPLE 33

N-[(R)-1,2-Diphenylethyl]-3-oxo-4-aza-5α-androstane-17β-carboxamide

The title compound was prepared in a yield of 83% in a similar manner to that described in Example 1 by reacting 3-oxo-4-aza-5α-androstane-17β-carboxylic acid and (R)-1,2-diphenylethylamine.

Nuclear Magnetic Resonance Spectrum (CDCl$_3$), δ ppm:
0.46 (3H, singlet);
0.88 (3H, singlet);
0.65–3.30 (23H, multiplet);
5.33 (1H, quartet, J=5 Hz);
5.48 (1H, doublet, J=5 Hz);
6.80 (1H, broad);
7.10–7.40 (10H, multiplet).

Infrared Absorption Spectrum (KBr), $\nu_{max}$ cm$^{-1}$: 3218, 2935, 1663, 1494, 1453, 1361, 1305, 1229, 1121, 704.

EXAMPLE 34

N,N-Dibenzyl-4-methyl-3-oxo-4-aza-5α-androstane-17β-carboxamide

The title compound was prepared in a yield of 80% in a similar manner to that described in Example 1 by reacting 4-methyl-3-oxo-4-aza-5α-androstane-17β-carboxylic acid (prepared as described in Preparation 2) and N,N-dibenzylamine.

Nuclear Magnetic Resonance Spectrum (CDCl$_3$), δ ppm:
0.89 (6H, singlet);
0.65–2.50 (19H, multiplet);
2.75 (1H, triplet, J=10 Hz);
2.72 (3H, singlet);
3.00 (1H, doublet of doublets, J=13 & 4 Hz);
3.75 (1H, doublet, J=15 Hz);
4.15 (1H, doublet, J=16 Hz);
4.91 (1H, doublet, J=16 Hz);
5.46 (1H, doublet, J=15 Hz);
7.07–7.40 (10H, multiplet).

Infrared Absorption Spectrum (KBr), $\nu_{max}$ cm$^{-1}$: 2941, 2872, 1642, 1494, 1451, 1417, 1389, 1305, 1215, 735, 700.

EXAMPLE 35

N,N-Dibenzyl-4-methyl-3-oxo-4-aza-5α-androst-1-ene-17β-carboxamide

The title compound was prepared in a yield of 68% in a similar manner to that described in Example 1 by reacting 4-methyl-3-oxo-4-aza-5α-androst-1-ene-17β-carboxylic acid (prepared as described in Preparation 4) and N,N-dibenzylamine.

Nuclear Magnetic Resonance Spectrum (CDCl$_3$), δ ppm:
0.90 (3H, singlet);
0.94 (3H, singlet);
0.80–2.20 (15H, multiplet);
2.75 (1H, doublet, J=9 Hz);
2.95 (3H, singlet);
3.31 (1H, doublet of doublets, J=12 & 4 Hz);
3.75 (1H, doublet, J=13 Hz);
4.18 (1H, doublet, J=15 Hz);
4.19 (1H, doublet, J=15 Hz);
5.45 (1H, doublet, J=13 Hz);
5.82 (1H, doublet, J=10 Hz);
6.64 (1H, doublet, J=10 Hz);
7.06–7.43 (10H, multiplet).

Infrared Absorption Spectrum (KBr), $\nu_{max}$ cm$^{-1}$: 2940, 1664, 1641, 1606, 1494, 1424, 1217, 820, 735, 698.

EXAMPLE 36

N,N-Dibenzyl-4-methyl-3-oxo-4-azaandrost-5-ene-17β-carboxamide

The title compound was prepared in a yield of 74% in a similar manner to that described in Example 1 by reacting 4-methyl-3-oxo-4-azaandrost-5-ene-17β-carboxylic acid (prepared as described in Preparation 5) and N,N-dibenzylamine.

Nuclear Magnetic Resonance Spectrum (CDCl$_3$), δ ppm:
0.92 (3H, singlet);
1.06 (3H, singlet);
1.00-2.60 (17H, multiplet);
2.77 (1H, triplet, J=9 Hz);
3.11 (3H, singlet);
3.75 (1H, doublet, J=13 Hz);
4.18 (1H, doublet, J=15 Hz);
4.94 (1H, doublet, J=15 Hz);
5.03 (1H, multiplet);
5.47 (1H, doublet, J=13 Hz);
7.07-7.43 (10H, multiplet).

Infrared Absorption Spectrum (KBr), $v_{max}$ cm$^{-1}$: 2967, 2902, 1666, 1641, 1411, 1201, 1054, 732, 697.

EXAMPLE 37

N-(1-Methyl-1-phenylethyl)-3-oxo-4-aza-5α-androstane-17β-carboxamide 5.00 g of 3-oxo-4-aza-5α-androstane-17β-carboxylic acid, 8.00 g of triphenylphosphine and 7.00 g of 2,2'-dipyridyl disulfide were added, in that order, to 30 ml of dry toluene. The reaction solution was then allowed to stand at room temperature overnight, whilst stirring, after which it was purified by column chromatography through 100 g of silica gel. Gradient elution with mixtures of acetone and methylene chloride ranging from 1:9 to 1:1 by volume afforded 5.96 g of the 2-pyridylthio ester of 3-oxo-4-aza-5α-androstane-17β-carboxylic acid.

150 mg of the 2-pyridylthio ester prepared as described above and 500 mg of 1-methyl-1-phenylethylamine were added, in that order, to 5 ml of dry tetrahydrofuran. The reaction solution was then allowed to stand at room temperature for 3 days, whilst stirring. At the end of this time, the solution was diluted with 100 ml of methylene chloride, washed with 1N aqueous hydrochloric acid, with water, with an aqueous solution of sodium hydrogencarbonate and with a saturated aqueous solution of sodium chloride, in that order, and dried over anhydrous magnesium sulfate. The solvent was then removed by distillation under reduced pressure. The resulting residue was purified by column chromatography through 15 g of silica gel. Gradient elution with mixtures of acetone and methylene chloride ranging from 1:9 to 1:1 by volume afforded 112 mg of the title compound.

Nuclear Magnetic Resonance Spectrum (CDCl$_3$), δ ppm:
0.68 (3H, singlet);
0.90 (3H, singlet);
0.70-2.20 (18H, multiplet);
1.70 (3H, singlet);
1.72 (3H, singlet);
2.35-2.50 (2H, multiplet);
3.06 (1H, doublet of doublets, J=12 & 5 Hz);
5.52 (1H, broad);
5.60 (1H, broad);
7.20-7.45 (5H, multiplet).

Infrared Absorption Spectrum (KBr), $v_{max}$ cm$^{-1}$: 2938, 2919, 1699, 1672, 1495, 1447, 1361, 1308, 1257, 1233, 697.

EXAMPLE 38

N-(1-Methyl-1-phenylethyl)-3-oxo-4-aza-5α-androst-1-ene-17β-carboxamide

The title compound was prepared in a yield of 70% in a similar manner to that described in Example 37 by reacting 3-oxo-4-aza-5α-androst-1-ene-17β-carboxylic acid and 1-methyl-1-phenylethylamine.

Nuclear Magnetic Resonance Spectrum (CDCl$_3$), δ ppm:
0.69 (3H, singlet);
0.98 (3H, singlet);
0.90-2.25 (16H, multiplet);
1.71 (3H, singlet);
1.73 (3H, singlet);
3.33 (1H, triplet, J=8 Hz);
5.53 (1H, broad);
5.69 (1H, broad);
5.84 (1H, doublet, J=10 Hz);
6.81 (1H, doublet, J=10 Hz);
7.20-7.45 (5H, multiplet).

Infrared Absorption Spectrum (KBr), $v_{max}$ cm$^{-1}$: 2969, 2937, 1672, 1598, 1494, 1446, 1254, 821, 761, 696.

EXAMPLE 39

N-(1-Methyl-1-phenylethyl)-3-oxo-4-azaandrost-5-ene-17β-carboxamide

The title compound was prepared in a yield of 68% in a similar manner to that described in Example 37 by reacting 3-oxo-4-azaandrost-5-ene-17β-carboxylic acid and 1-methyl-1-phenylethylamine.

Nuclear Magnetic Resonance Spectrum (CDCl$_3$), δ ppm:
0.71 (3H, singlet);
1.11 (3H, singlet);
1.00-2.60 (18H, multiplet);
1.71 (3H, singlet);
1.73 (3H, singlet);
4.83 (1H, multiplet);
5.52 (1H, broad);
7.20-7.50 (6H, multiplet).

Infrared Absorption Spectrum (KBr), $v_{max}$ cm$^{-1}$: 2969, 2940, 2907, 1707, 1673, 1495, 1448, 1386, 1225, 761, 697.

EXAMPLE 40

N-(1-Methyl-1-phenylethyl)-4-methyl-3-oxo-4-aza-5α-androstane-17β-carboxamide

The title compound was prepared in a yield of 82% in a similar manner to that described in Example 37 by reacting 4-methyl-3-oxo-4-aza-5α-androstane-17β-carboxylic acid (prepared as described in Preparation 2) and 1-methyl-1-phenylethylamine.

Nuclear Magnetic Resonance Spectrum (CDCl$_3$), δ ppm:
0.69 (3H, singlet);
0.89 (3H, singlet);
0.70-2.20 (18H, multiplet);
1.70 (3H, singlet);
1.73 (3H, singlet);
2.47 (2H, multiplet);
2.94 (3H, singlet);
3.04 (1H, doublet of doublets, J=12 & 3 Hz);
5.53 (1H, broad);
b 7.20-7.50 (5H, multiplet).

Infrared Absorption Spectrum (KBr), $\nu_{max}$ cm$^{-1}$: 3315, 2967, 2942, 1670, 1628, 1547, 1527, 1442, 1368, 1228, 762, 698.

EXAMPLE 41

N-(1-Methyl-1-phenylethyl)-4-methyl-3-oxo-4-aza-5α-androst-1-ene-17β-carboxamide The title compound was prepared in a yield of 66% in a similar manner to that described in Example 37 by reacting 4-methyl-3-oxo-4-aza-5α-androst-1-ene-17β-carboxylic acid (prepared as described in Preparation 4) and 1-methyl-1-phenylethylamine.

Nuclear Magnetic Resonance Spectrum (CDCl$_3$), δ ppm:
 0.69 (3H, singlet);
 0.93 (3H, singlet);
 0.90–2.35 (16H, multiplet);
 1.71 (3H, singlet);
 1.73 (3H, singlet);
 2.96 (3H, singlet);
 3.35 (1H, doublet of doublets, J=13 & 4 Hz);
 5.53 (1H, broad);
 5.85 (1H, doublet, J=10 Hz);
 6.68 (1H, doublet, J=10 Hz);
 7.20–7.45 (5H, multiplet).

Infrared Absorption Spectrum (KBr), $\nu_{max}$ cm$^{-1}$: 3332, 2964, 2943, 1674, 1658, 1604, 1537, 1448, 1244, 821, 705.

EXAMPLE 42

N-(1-Methyl-1-phenylethyl)-4-methyl-3-oxo-4-aza-androst-5-ene-17β-carboxamide

The title compound was prepared in a yield of 70% in a similar manner to that described in Example 37 by reacting 4-methyl-3-oxo-4-azaandrost-5-ene-17β-carboxylic acid (prepared as described in Preparation 5) and 1-methyl-1-phenylethylamine.

Nuclear Magnetic Resonance Spectrum (CDCl$_3$), δ ppm:
 0.71 (3H, singlet);
 1.06 (3H, singlet);
 1.00–2.30 (16H, multiplet);
 1.71 (3H, singlet);
 1.74 (3H, singlet);
 2.50–2.60 (2H, multiplet);
 3.13 (3H, singlet);
 5.04 (1H, multiplet);
 5.53 (1H, broad);
 7.20–7.45 (5H, multiplet).

Infrared Absorption Spectrum (KBr), $\nu_{max}$ cm$^{-1}$: 3333, 2970, 2950, 1677, 1636, 1519, 1448, 1382, 1245, 761, 696.

EXAMPLE 43

N-[1-(4-Methoxyphenyl)-1-methylethyl]-3-oxo-4-aza-5α-androstane-17β-carboxamide

The title compound was prepared in a yield of 82% in a similar manner to that described in Example 37 by reacting 3-oxo-4-aza-5α-androstane-17β-carboxylic acid and 1-(4-methoxyphenyl)-1-methylethylamine.

Nuclear Magnetic Resonance Spectrum (CDCl$_3$), δ ppm:
 0.68 (3H, singlet);
 0.90 (3H, singlet);
 0.70–2.80 (20H, multiplet);
 1.69 (3H, singlet);
 1.71 (3H, singlet);
 3.08 (1H, doublet of doublets, J=13 & 4 Hz);
 3.80 (3H, singlet);
 5.49 (1H, broad);
 6.25 (1H, broad);
 6.88 (2H, doublet, J=9 Hz);
 7.30 (2H, doublet, J=9 Hz).

Infrared Absorption Spectrum (KBr), $\nu_{max}$ cm$^{-1}$: 2939, 1701, 1674, 1615, 1514, 1497, 1455, 1360, 1251, 1180, 1034, 827.

EXAMPLE 44

N-[1-(4-Methoxyphenyl)-1-methylethyl]-3-oxo-4-aza-5α-androst-1-ene-17β-carboxamide The title compound was prepared in a yield of 78% in a similar manner to that described in Example 37 by reacting 3-oxo-4-aza-5α-androst-1-ene-17β-carboxylic acid and 1-(4-methoxyphenyl)-1-methylethylamine.

Nuclear Magnetic Resonance Spectrum (CDCl$_3$), δ ppm:
 0.68 (3H, singlet);
 0.98 (3H, singlet);
 0.90–2.20 (16H, multiplet);
 1.70 (3H, singlet);
 1.72 (3H, singlet);
 3.35 (1H, doublet, J=9 Hz);
 3.80 (3H, singlet);
 5.48 (1H, broad);
 5.76 (1H, broad);
 5.83 (1H, doublet, J=10 Hz);
 6.82 (1H, doublet, J=10 Hz);
 6.88 (1H, doublet, J=9 Hz);
 7.32 (2H, doublet, J=9 Hz).

Infrared Absorption Spectrum (KBr), $\nu_{max}$ cm$^{-1}$: 2969, 2938, 1672, 1599, 1514, 1455, 1248, 1181, 1035, 825.

EXAMPLE 45

N-[1-(4-Methoxyphenyl)-1-methylethyl]-3-oxo-4-aza-androst-5-ene-17β-carboxamide

The title compound was prepared in a yield of 65% in a similar manner to that described in Example 37 by reacting 3-oxo-4-azaandrost-5-ene-17β-carboxylic acid and 1-(4-methoxyphenyl)-1-methylethylamine.

Nuclear Magnetic Resonance Spectrum (CDCl$_3$), δ ppm:
 0.70 (3H, singlet);
 1.10 (3H, singlet);
 1.00–2.70 (18H, multiplet);
 1.70 (3H, singlet);
 1.72 (3H, singlet);
 3.80 (3H, singlet);
 4.91 (1H, multiplet);
 5.50 (1H, broad);
 6.88 (2H, doublet, J=9 Hz);
 7.34 (2H, doublet, J=9 Hz);
 7.96 (1H, broad).

Infrared Absorption Spectrum (KBr), $\nu_{max}$ cm$^{-1}$: 2940, 1708, 1672, 1615, 1514, 1497, 1385, 1251, 1180, 1033, 826.

EXAMPLE 46

N-[1-(4-Methoxyphenyl)-1-methylethyl]-4-methyl-3-oxo-4-aza-5α-androstane-17β-carboxamide The title compound was prepared in a yield of 82% in a similar manner to that described in Example 37 by reacting 4-methyl-3-oxo-4-aza-5α-androstane-17β-carboxylic acid (prepared as described in Preparation 2) and 1-(4-methoxyphenyl)-1-methylethylamine.

Nuclear Magnetic Resonance Spectrum (CDCl$_3$), δ ppm:
- 0.68 (3H, singlet);
- 0.90 (3H, singlet);
- 0.70–2.60 (20H, multiplet);
- 1.69 (3H, multiplet);
- 1.71 (3H, singlet);
- 2.94 (3H, singlet);
- 3.05 (1H, doublet of doublets, J=13 & 4 Hz);
- 3.79 (3H, singlet);
- 5.49 (1H, broad);
- 6.86 (1H, doublet, J=9 Hz);
- 7.31 (1H, doublet, J=9 Hz).

Infrared Absorption Spectrum (KBr), $\nu_{max}$ cm$^{-1}$: 3333, 2940, 1675, 1643, 1513, 1455, 1384, 1304, 1247, 1180, 1035, 828.

EXAMPLE 47

N-[1-(4-Methoxyphenyl)-1-methylethyl]-4-methyl-3-oxo-4-aza-5α-androst-1-ene-17β-carboxamide The title compound was prepared in a yield of 71% in a similar manner to that described in Example 37 by reacting 4-methyl-3-oxo-4-aza-5α-androst-1-ene-17β-carboxylic acid (prepared as described in Preparation 4) and 1-(4-methoxyphenyl)-1-methylethylamine.

Nuclear Magnetic Resonance Spectrum (CDCl$_3$), δ ppm:
- 0.69 (3H, singlet);
- 0.92 (3H, singlet);
- 0.80–2.30 (16H, multiplet);
- 1.70 (3H, singlet);
- 1.72 (3H, singlet);
- 2.96 (3H, singlet);
- 3.36 (1H, doublet of doublets, J=13 & 4 Hz);
- 3.79 (3H, singlet);
- 5.50 (1H, broad);
- 5.86 (1H, doublet, J=10 Hz);
- 6.69 (1H, doublet, J=10 Hz);
- 6.88 (1H, doublet, J=9 Hz);
- 7.35 (1H, doublet, J=9 Hz).

Infrared Absorption Spectrum (KBr), $\nu_{max}$ cm$^{-1}$: 2968, 2940, 1662, 1605, 1513, 1453, 1247, 1180, 1034, 827.

EXAMPLE 48

N-[1-(4-Methoxyphenyl)-1-methylethyl]-4-methyl-3-oxo-4-azaandrost-5-ene-17-carboxamide The title compound was prepared in a yield of 72% in a similar manner to that described in Example 37 by reacting 4-methyl-3-oxo-4-azaandrost-5-ene-17β-carboxylic acid (prepared as described in Preparation 5) and 1-(4-methoxyphenyl)-1-methylethylamine.

Nuclear Magnetic Resonance Spectrum (CDCl$_3$), δ ppm:
- 0.70 (3H, singlet);
- 1.06 (3H, singlet);
- 1.00–2.30 (16H, multiplet);
- 2.50–2.60 (2H, multiplet);
- 1.70 (3H, singlet);
- 1.72 (3H, singlet);
- 3.12 (3H, singlet);
- 3.80 (3H, singlet);
- 5.04 (1H, multiplet);
- 5.50 (1H, broad);
- 6.88 (2H, doublet, J=9 Hz);
- 7.32 (1H, doublet, J=9 Hz).

Infrared Absorption Spectrum (KBr), $\nu_{max}$ cm$^{-1}$: 3344, 2967, 2945, 1670, 1642, 1513, 1455, 1386, 1305, 1247, 1180, 1034, 829.

EXAMPLE 49

N-[1-(2-Thienyl)-1-methylethyl]-3-oxo-4-aza-5α-androstane-17β-carboxamide

The title compound was prepared in a yield of 96% in a similar manner to that described in Example 37 by reacting 3-oxo-4-aza-5α-androstane-17β-carboxylic acid and 1-(2-thienyl)-1-methylethylamine.

Nuclear Magnetic Resonance Spectrum (CDCl$_3$), δ ppm:
- 0.67 (3H, singlet);
- 0.90 (3H, singlet);
- 1.81 (3H, singlet);
- 1.82 (3H, singlet);
- 0.70–2.35 (18H, multiplet);
- 2.39–2.45 (2H, multiplet);
- 3.06 (1H, doublet of doublets, J=11 & 4 Hz);
- 5.51 (1H, broad);
- 5.78 (1H, broad);
- 6.91–6.99 (2H, multiplet);
- 7.17 (1H, doublet of doublets, J=5 & 2 Hz).

Infrared Absorption Spectrum (KBr), $\nu_{max}$ cm$^{-1}$: 3296, 2937, 1663, 1449, 1360, 695.

EXAMPLE 50

N-[1-(2-Thienyl)-1-methylethyl]-3-oxo-4-azaandrost-5-ene-17β-carboxamide

The title compound was prepared in a yield of 27% in a similar manner to that described in Example 2 by reacting 3-oxo-4-azaandrost-5-ene-17β-carboxylic acid and 1-(2-thienyl)-1-methylethylamine.

Nuclear Magnetic Resonance Spectrum (CDCl$_3$), δ ppm:
- 0.71 (3H, singlet);
- 1.10 (3H, singlet);
- 1.05–2.30 (16H, multiplet);
- 1.82 (3H, singlet);
- 1.89 (3H, singlet);
- 2.47–2.53 (2H, multiplet);
- 4.85 (1H, doublet, J=3 Hz);
- 5.54 (1H, singlet);
- 6.91–6.99 (2H, multiplet);
- 7.17 (1H, doublet of doublets, J=5 & 2 Hz);
- 7.53 (1H, broad).

Infrared Absorption Spectrum (KBr), $\nu_{max}$ cm$^{-1}$: 3200, 2940, 1706, 1678, 1495, 1386, 1246, 1225, 695.

EXAMPLE 51

N-[α-(4-Chlorophenyl)benzyl]-3-oxo-4-aza-5α-androstane-17β-carboxamide

The title compound was prepared in a yield of 84% in a similar manner to that described in Example 2 by reacting 3-oxo-4-aza-5α-androstane-17β-carboxylic acid and α-(4-chlorophenyl)benzylamine.

Nuclear Magnetic Resonance Spectrum (CDCl$_3$), δ ppm:
- 0.66 & 0.67 (total 3H, each singlet);
- 0.89 & 0.90 (total 3H, each singlet);
- 0.73–2.45 (20H, multiplet);
- 3.05 (1H, doublet of doublets, J=11 & 4 Hz);
- 5.84 (1H, doublet, J=8 Hz);

5.88 (1H, broad);
6.22 & 6.25 (total 1H, each doublet, J=8 Hz);
7.13-7.37 (9H, multiplet).
Infrared Absorption Spectrum (KBr), $\nu_{max}$ cm$^{-1}$:
3360, 2978, 1736, 1652, 1514, 1371, 1199.

EXAMPLE 52

N-[α-(4-Chlorophenyl)benzyl]-3-oxo-4-aza-5α-androst-1-ene-17β-carboxamide

The title compound was prepared in a yield of 63% in a similar manner to that described in Example 2 by reacting 3-oxo-4-aza-5α-androst-1-ene-17β-carboxylic acid and α-(4-chlorophenyl)benzylamine.

Nuclear Magnetic Resonance Spectrum (CDCl$_3$), δ ppm:
0.68 & 0.69 (total 3H, each singlet);
0.96 & 0.97 (total 3H, each singlet);
0.80-2.30 (16H, multiplet);
3.33 (1H, triplet, J=8 Hz);
5.68 (1H, broad);
5.80-5.85 (2H, multiplet);
6.23 & 6.26 (total 1H, each doublet, J=10 Hz);
6.79 & 6.82 (total 1H, each doublet, J=10 Hz);
7.14-7.37 (9H, multiplet).
Infrared Absorption Spectrum (KBr), $\nu_{max}$ cm$^{-1}$:
3293, 2936, 1676, 1601, 1490, 815, 700.

EXAMPLE 53

N-[α-(4-Chlorophenyl)benzyl]-3-oxo-4-azaandrost-5-ene-17β-carboxamide

The title compound was prepared in a yield of 78% in a similar manner to that described in Example 2 by reacting 3-oxo-4-azaandrost-5-ene-17β-carboxylic acid and α-(4-chlorophenyl)benzylamine.

Nuclear Magnetic Resonance Spectrum (CDCl$_3$), δ ppm:
0.70 & 0.71 (total 3H, each singlet);
1.08 & 1.10 (total 3H, each singlet);
1.10-2.60 (18H, multiplet);
4.89-4.91 (1H, multiplet);
5.86 (1H, doublet, J=7 Hz);
6.23 & 6.26 (total 1H, each doublet, J=7 Hz);
7.15-7.38 (9H, multiplet);
7.87 (1H, broad).
Infrared Absorption Spectrum (KBr), $\nu_{max}$ cm$^{-1}$:
2943, 1661, 1490, 1386, 694.

EXAMPLE 54

N-[α-(4-Chlorophenyl)benzyl]-4-methyl-3-oxo-4-aza-5α-androstane-17β-carboxamide

The title compound was prepared in a yield of 78% in a similar manner to that described in Example 2 by reacting 4-methyl-3-oxo-4-aza-5α-androstane-17β-carboxylic acid (prepared as described in Preparation 2) and α-(4-chlorophenyl)benzylamine.

Nuclear Magnetic Resonance Spectrum (CDCl$_3$), δ ppm:
0.66 & 0.67 (total 3H, each singlet);
0.87 & 0.88 (total 3H, each singlet);
0.70-2.60 (20H, multiplet);
2.94 (3H, singlet);
3.01-3.07 (1H, multiplet);
5.83 (1H, doublet, J=6 Hz);
6.22-6.26 (1H, multiplet);
7.14-7.37 (9H, multiplet).
Infrared Absorption Spectrum (KBr), $\nu_{max}$ cm$^{-1}$:
3305, 2940, 1646, 1622, 1521, 1490, 1226, 700.

EXAMPLE 55

N-[α-(4-Chlorophenyl)benzyl]-4-methyl-3-oxo-4-aza-5α-androst-1-ene-17β-carboxamide The title compound was prepared in a yield of 58% in a similar manner to that described in Example 2 by reacting 4-methyl-3-oxo-4-aza-5α-androst-1-ene-17β-carboxylic acid (prepared as described in Preparation 4) and α-(4-chlorophenyl)benzylamine.

Nuclear Magnetic Resonance Spectrum (CDCl$_3$), δ ppm:
0.67 & 0.68 (total 3H, each singlet);
0.91 & 0.92 (total 3H, each singlet);
0.84-2.30 (16H, multiplet);
2.94 (3H, singlet);
3.34 (1H, doublet of doublets, J=13 & 3 Hz);
5.82-5.87 (2H, multiplet);
6.23 & 6.26 (total 1H, each doublet, J=8 Hz);
6.74 & 6.77 (total 1H, each doublet, J=10 Hz);
7.14-7.64 (9H, multiplet).
Infrared Absorption Spectrum (KBr), $\nu_{max}$ cm$^{-1}$:
3430, 2940, 2910, 2447, 1621, 1522, 1463, 1441, 1277, 1250, 1139, 1019, 761.

EXAMPLE 56

N-[α-(4-Chlorophenyl)benzyl]-4-methyl-3-oxo-4-azaandrost-5-ene-17β-carboxamide

The title compound was prepared in a yield of 80% in a similar manner to that described in Example 2 by reacting 4-methyl-3-oxo-4-azaandrost-5-ene-17β-carboxylic acid (prepared as described in Preparation 5) and α-(4-chlorophenyl)benzylamine.

Nuclear Magnetic Resonance Spectrum (CDCl$_3$), δ ppm:
0.69 & 0.70 (total 3H, each singlet);
1.04 & 1.05 (total 3H, each singlet);
1.10-2.60 (18H, multiplet);
3.12 (3H, singlet);
5.02-5.05 (1H, multiplet);
5.85 (1H, doublet, J=7 Hz);
6.23 & 6.26 (total 1H, each doublet, J=7 Hz);
7.15-7.38 (9H, multiplet).
Infrared Absorption Spectrum (KBr), $\nu_{max}$ cm$^{-1}$:
3316, 2945, 1670, 1644, 1518, 1490, 1388, 700.

EXAMPLE 57

N-[α-(4-Hydroxyphenyl)benzyl]-3-oxo-4-aza-5α-androstane-17β-carboxamide

The title compound was prepared in a yield of 63% in a similar manner to that described in Example 37 by reacting 3-oxo-4-aza-5α-androstane-17β-carboxylic acid and α-(4-chlorophenyl)benzylamine.

Nuclear Magnetic Resonance Spectrum (CDCl$_3$), δ ppm:
0.66 (3H, singlet);
0.88 (3H, singlet);
0.70-3.02 (21H, multiplet);
3.05 (1H, doublet of doublets, J=12 & 4 Hz);
5.85-5.89 (2H, multiplet);
6.19 (1H, doublet, J=8 Hz);
6.72-6.78 (2H, multiplet);
7.01-7.06 (2H, multiplet);
7.19-7.34 (5H, multiplet).

Infrared Absorption Spectrum (KBr), $v_{max}$ cm$^{-1}$:
3292, 2937, 1652, 1514, 1495, 1228, 699.

EXAMPLE 58

N-[α-(4-Hydroxyphenyl)benzyl]-3-oxo-4-aza-5α-androst-1-ene-17β-carboxamide

The title compound was prepared in a yield of 95% in a similar manner to that described in Example 37 by reacting 3-oxo-4-aza-5α-androst-1-ene-17β-carboxylic acid and α-(4-hydrophenyl)benzylamine.

Nuclear Magnetic Resonance Spectrum (CDCl$_3$), δ ppm:
  0.67 & 0.68 (total 3H, each singlet);
  0.95 & 0.96 (total 3H, each singlet);
  0.80-3.20 (17H, multiplet);
  3.32 (1H, triplet, J=8 Hz);
  5.52 (1H, broad);
  5.82 (1H, doublet, J=10 Hz);
  5.90 (1H, doublet, J=7 Hz);
  6.19 (1H, doublet, J=7 Hz);
  6.72-6.81 (3H, multiplet);
  7.02-7.07 (2H, multiplet);
  7.20-7.35 (5H, multiplet).

Infrared Absorption Spectrum (KBr), $v_{max}$ cm$^{-1}$:
3292, 2937, 1668, 1613, 1596, 1514, 1495, 1450, 1223, 816, 699.

EXAMPLE 59

N-[α-(4-Hydroxyphenyl)benzyl]-3-oxo-4-azaandrost-5-ene-17β-carboxamide

The title compound was prepared in a yield of 77% in a similar manner to that described in Example 37 by reacting 3-oxo-4-azaandrost-5-ene-17β-carboxylic acid and α-(4-hydroxyphenyl)benzylamine.

Nuclear Magnetic Resonance Spectrum (CDCl$_3$+CD$_3$OD), δ ppm:
  0.65 & 0.69 (total 3H, each singlet);
  0.99 & 1.08 (total 3H, each singlet);
  0.85-2.65 (22H, multiplet);
  6.17 (1H, singlet);
  6.75-6.79 (2H, multiplet);
  7.02-7.07 (2H, multiplet);
  7.20-7.35 (5H, multiplet).

Infrared Absorption Spectrum (KBr), $v_{max}$ cm$^{-1}$:
3189, 2943, 1673, 1661, 1612, 1514, 1493, 1386, 1222, 832, 700.

EXAMPLE 60

N-[α-(4-Hydroxyphenyl)benzyl]-4-methyl-3-oxo-4-aza-5α-androstane-17β-carboxamide The title compound was prepared in a yield of 46% in a similar manner to that described in Example 2 by reacting 4-methyl-3-oxo-4-aza-5α-androstane-17β-carboxylic acid (prepared as described in Preparation 2) and α-(4-hydroxyphenyl)benzylamine.

Nuclear Magnetic Resonance Spectrum (CDCl$_3$), δ ppm:
  0.67 (3H, singlet);
  0.87 & 0.88 (total 3H, each singlet);
  0.70-2.50 (21H, multiplet);
  2.92 (3H, singlet);
  3.03 (1H, doublet of doublets, J=13 & 3 Hz);
  5.84-5.87 (1H, multiplet);
  6.17-6.21 (1H, multiplet);
  6.74-6.79 (2H, multiplet);
  7.02-7.06 (2H, multiplet);
  7.20-7.35 (5H, multiplet).

Infrared Absorption Spectrum (KBr), $v_{max}$ cm$^{-1}$:
3292, 2940, 1644, 1617, 1590, 1514, 1494, 1452, 1228, 699.

EXAMPLE 61

N-[(R)-2-(4-Methylphenyl)-1-phenylethyl]-3-oxo-4-aza-5α-androstane-17β-carboxamide The title compound was prepared in a yield of 80% in a similar manner to that described in Example 1 by reacting 3-oxo-4-aza-5α-androstane-17β-carboxylic acid and (R)-2-(4-methylphenyl)-1-phenylethylamine.

Nuclear Magnetic Resonance Spectrum (CDCl$_3$), δ ppm:
  0.47 (3H, singlet);
  0.88 (3H, singlet);
  2.25 (3H, singlet);
  0.65-3.30 (23H, multiplet);
  5.34 (1H, quartet, J=5 Hz);
  5.48 (1H, doublet, J=5 Hz);
  6.80 (1H, broad);
  7.1-7.4 (9H, multiplet).

Infrared Absorption Spectrum (KBr), $v_{max}$ cm$^{-1}$:
3218, 2935, 1664, 1495, 1305, 1121.

EXAMPLE 62

N-[(S)-2-(4-Methylphenyl)-1-phenylethyl]-3-oxo-4-aza-5α-androstane-17β-carboxamide The title compound was prepared in a yield of 81% in a similar manner to that described in Example 1 by reacting 3-oxo-4-aza-5α-androstane-17β-carboxylic acid and (S)-2-(4-methylphenyl)-1-phenylethylamine.

Nuclear Magnetic Resonance Spectrum (CDCl$_3$), δ ppm:
  0.51 (3H, singlet);
  0.88 (3H, singlet);
  0.70-3.20 (23H, multiplet);
  2.29 (3H, singlet);
  5.23 (1H, quartet, J=7 Hz);
  5.57 (1H, doublet, J=7 Hz);
  6.50 (1H, broad);
  6.94 (2H, doublet, J=8 Hz);
  7.02 (2H, doublet, J=8 Hz);
  7.15-7.35 (5H, multiplet).

Infrared Absorption Spectrum (KBr), $v_{max}$ cm$^{-1}$:
2939, 1664, 1516, 1496, 1371, 1361, 1313, 1234, 1120, 789, 704.

EXAMPLE 63

N-[(S)-2-(4-Methylphenyl)-1-phenylethyl]-4-methyl-3-oxo-4-aza-5α-androstane-17β-carboxamide The title compound was prepared in a yield of 46% in a similar manner to that described in Example 2 by reacting 4-methyl-3-oxo-4-aza-5α-androstane-17β-carboxylic acid (prepared as described in Preparation 2) and (S)-2-(4-methylphenyl)-1-phenylethylamine.

Nuclear Magnetic Resonance Spectrum (CDCl$_3$), δ ppm:
  0.51 (3H, singlet);
  0.85 (3H, singlet);
  0.70-2.50 (20H, multiplet);
  2.29 (3H, singlet);
  2.91 (3H, singlet);
  2.90-3.15 (3H, multiplet);
  5.25 (1H, quartet, J=7 Hz);
  5.58 (1H, doublet, J=7 Hz);

6.95 (2H, doublet, J=8 Hz);
7.02 (2H, doublet, J=8 Hz);
7.15-7.35 (5H, multiplet).
Infrared Absorption Spectrum (KBr), $\nu_{max}$ cm$^{-1}$: 3323, 2942, 1646, 1516, 1454, 1393, 1305, 1228, 1103, 1037, 700.

EXAMPLE 64

N,N-Diphenyl-3-oxo-4-aza-5α-androstane-17β-carbohydrazide

The title compound was prepared in a yield of 57% in a similar manner to that described in Example 37 by reacting 3-oxo-4-aza-5α-androstane-17β-carboxylic acid and N,N-diphenylhydrazine.

Nuclear Magnetic Resonance Spectrum (CDCl$_3$), δ ppm:
0.70 (3H, singlet);
0.90 (3H, singlet);
0.70-2.50 (20H, multiplet);
3.05 (1H, doublet of doublets, J=13 & 4 Hz);
5.45 (1H, broad);
6.97-7.37 (10H, multiplet);
7.51 (1H, broad).
Infrared Absorption Spectrum (KBr), $\nu_{max}$ cm$^{-1}$: 3198, 2934, 1698, 1652, 1589, 1493, 1324, 1188, 1120, 746, 693.

EXAMPLE 65

N,N-Diphenyl-3-oxo-4-aza-5α-androst-1-ene-17β-carbohydrazide

The title compound was prepared in a yield of 22% in a similar manner to that described in Example 2 by reacting 3-oxo-4-aza-5α-androst-1-ene-17β-carboxylic acid and N,N-diphenylhydrazine.

Nuclear Magnetic Resonance Spectrum (CDCl$_3$), δ ppm:
0.71 (3H, singlet);
0.97 (3H, singlet);
0.86-2.25 (20H, multiplet);
3.33 (1H, doublet of doublets, J=9 & 7 Hz);
5.48 (1H, broad);
5.82 (1H, doublet, J=10 Hz);
6.79 (1H, doublet, J=9 Hz);
6.98-7.35 (10H, multiplet);
7.53 (1H, singlet).
Infrared Absorption Spectrum (KBr), $\nu_{max}$ cm$^{-1}$: 3211, 2931, 1701, 1668, 1589, 1494, 1330, 814, 747, 693.

EXAMPLE 66

N,N-Diphenyl-3-oxo-4-azaandrost-5-ene-17β-carbohydrazide

The title compound was prepared in a yield of 25% in a similar manner to that described in Example 2 by reacting 3-oxo-4-azaandrost-5-ene-17β-carboxylic acid and N,N-diphenylhydrazine.

Nuclear Magnetic Resonance Spectrum (CDCl$_3$), δ ppm:
0.73 (3H, singlet);
1.10 (3H, singlet);
0.88-2.51 (19H, multiplet);
4.78 (1H, multiplet);
6.98-7.31 (10H, multiplet);
7.51 (1H, singlet).
Infrared Absorption Spectrum (KBr), $\nu_{max}$ cm$^{-1}$: 3240, 2944, 1682, 1662, 1590, 1495, 1385, 1222, 748, 691.

EXAMPLE 67

N,N-Diphenyl-4-methyl-3-oxo-4-aza-5α-androstane-17β-carbohydrazide

The title compound was prepared in a yield of 35% in a similar manner to that described in Example 2 by reacting 4-methyl-3-oxo-4-aza-5α-androstane-17β-carboxylic acid and N,N-diphenylhydrazine.

Nuclear Magnetic Resonance Spectrum (CDCl$_3$), δ ppm:
0.70 (3H, singlet);
0.88 (3H, singlet);
0.92-2.59 (20H, multiplet);
2.95 (3H, singlet);
3.06 (1H, doublet of doublets, J=12 & 3 Hz);
6.98-7.34 (10H, multiplet);
7.50 (1H, singlet).
Infrared Absorption Spectrum (KBr), $\nu_{max}$ cm$^{-1}$: 3236, 3208, 2935, 1695, 1619, 1602, 1494, 754, 693.

EXAMPLE 68

N,N-Diphenyl-4-methyl-3-oxo-4-aza-5α-androst-1-ene-17β-carbohydrazide

The title compound was prepared in a yield of 44% in a similar manner to that described in Example 2 by reacting 4-methyl-3-oxo-4-aza-5α-androst-1-ene-17β-carboxylic acid (prepared as described in Preparation 4) and N,N-diphenylhydrazine.

Nuclear Magnetic Resonance Spectrum (CDCl$_3$), δ ppm:
0.71 (3H, singlet);
0.92 (3H, singlet);
0.75-2.29 (16H, multiplet);
2.95 (3H, singlet);
3.34 (1H, doublet of doublets, J=13 & 4 Hz);
5.85 (1H, doublet, J=10 Hz);
6.67 (1H, doublet, J=10 Hz);
6.98-7.35 (10H, multiplet);
7.50 (1H, singlet).
Infrared Absorption Spectrum (KBr), $\nu_{max}$ cm$^{-1}$: 3252, 2941, 1664, 1590, 1495, 747, 691.

EXAMPLE 69

N,N-Diphenyl-4-methyl-3-oxo-4-azaandrost-5-ene-17β-carbohydrazide

The title compound was prepared in a yield of 25% in a similar manner to that described in Example 2 by reacting 4-methyl-3-oxo-4-azaandrost-5-ene-17β-carboxylic acid (prepared as described in Preparation 5) and N,N-diphenylhydrazine.

Nuclear Magnetic Resonance Spectrum (CDCl$_3$), δ ppm:
0.73 (3H, singlet);
1.05 (3H, singlet);
0.85-2.40 (16H, multiplet);
2.51-2.55 (2H, multiplet);
3.12 (3H, singlet);
5.02-5.05 (1H, multiplet);
6.99-7.32 (10H, multiplet);
7.49 (1H, singlet).
Infrared Absorption Spectrum (KBr), $\nu_{max}$ cm$^{-1}$: 3246, 2964, 1698, 1622, 1591, 1495, 1332, 754, 694.

EXAMPLE 70

N-[(1S,2R)-2-Hydroxy-1,2-diphenylethyl]-3-oxo-4-aza-5α-androstane-17β-carboxamide The title compound was prepared in a yield of 60% in a similar manner to that described in Example 37 by reacting 3-oxo-4-aza-5α-androstane-17β-carboxylic acid and (1R,2S)-2-amino-1,2-diphenylethanol.

Nuclear Magnetic Resonance Spectrum (CDCl$_3$+CD$_3$OD), δ ppm:
 0.60 (3H, singlet);
 0.89 (3H, singlet);
 0.70–2.50 (23H, multiplet);
 3.05 (1H, doublet of doublets, J=13 & 4 Hz);
 5.00 (1H, doublet, J=5 Hz);
 5.28 (1H, doublet, J=5 Hz);
 7.00–7.30 (10H, multiplet).

Infrared Absorption Spectrum (KBr), ν$_{max}$ cm$^{-1}$: 3426, 2938, 1659, 1494, 1453, 1387, 1307, 701.

EXAMPLE 71

N-[(1S,2R)-2-Hydroxy-1,2-diphenylethyl]-3-oxo-4-aza-5α-androst-1-ene-17β-carboxamide The title compound was prepared in a yield of 88% in a similar manner to that described in Example 37 by reacting 3-oxo-4-aza-5α-androst-1-ene-17β-carboxylic acid and (1R,2S)-2-amino-1,2-diphenylethanol.

Nuclear Magnetic Resonance Spectrum (CDCl$_3$+CD$_3$OD), δ ppm:
 0.60 (3H, singlet);
 0.97 (3H, singlet);
 0.90–2.20 (16H, multiplet);
 3.00 (3H, broad);
 3.32 (1H, doublet of doublets, J=13 & 4 Hz);
 5.00 (1H, doublet, J=5 Hz);
 5.28 (1H, doublet, J=5 Hz);
 5.83 (1H, doublet, J=9 Hz);
 6.87 (1H, doublet, J=9 Hz);
 7.05–7.30 (10H, multiplet).

Infrared Absorption Spectrum (KBr), ν$_{max}$ cm$^{-1}$: 3273, 2933, 1664, 1598, 1496, 1455, 822, 700.

EXAMPLE 72

N-[(1R,2S)-2-Hydroxy-1,2-diphenylethyl]-3-oxo-4-aza-5α-androstane-17β-carboxamide The title compound was prepared in a yield of 56% in a similar manner to that described in Example 37 by reacting 3-oxo-4-aza-5α-androstane-17β-carboxylic acid and (1S,2R)-2-amino-1,2-diphenylethanol.

Nuclear Magnetic Resonance Spectrum (CDCl$_3$), δ ppm:
 0.66 (3H, singlet);
 0.87 (3H, singlet);
 0.70–2.70 (21H, multiplet);
 3.05 (1H, doublet of doublets, J=13 & 3 Hz);
 5.07 (1H, doublet, J=4 Hz);
 5.30 (1H, doublet of doublets, J=7 & 4 Hz);
 5.76 (1H, broad);
 6.12 (1H, doublet, J=7 Hz);
 6.96–7.08 (4H, multiplet);
 7.16–7.30 (6H, multiplet).

Infrared Absorption Spectrum (KBr), ν$_{max}$ cm$^{-1}$: 3292, 3210, 2932, 1664, 1490, 1453, 1360, 1308, 698, 586.

EXAMPLE 73

N-[(1R,2S)-2-Hydroxy-1,2-diphenylethyl]-3-oxo-4-aza-5α-androst-1-ene-17β-carboxamide The title compound was prepared in a yield of 71% in a similar manner to that described in Example 37 by reacting 3-oxo-4-aza-5α-androst-1-ene-17β-carboxylic acid and (1S,2R)-2-amino-1,2-diphenylethanol.

Nuclear Magnetic Resonance Spectrum (CDCl$_3$), δ ppm:
 0.57 (3H, singlet);
 0.95 (3H, singlet);
 0.80–2.80 (17H, multiplet);
 3.35 (1H, multiplet);
 5.08 (1H, doublet, J=4 Hz);
 5.31 (1H, doublet of doublets, J=7 & 4 Hz);
 5.84 (1H, doublet, J=9 Hz);
 6.05 (1H, broad);
 6.16 (1H, doublet, J=7 Hz);
 6.84 (1H, doublet, J=9 Hz);
 6.95–7.40 (10H, multiplet).

Infrared Absorption Spectrum (KBr), ν$_{max}$ cm$^{-1}$: 3438, 3278, 2931, 2846, 1679, 1601, 1494, 1452, 1386, 1220, 1124, 1064, 825, 700, 589.

EXAMPLE 74

N-(α-Methoxycarbonyl-α-phenylbenzyl)-3-oxo-4-azaandrost-5-ene-17β-carboxamide

The title compound was prepared in a yield of 29% in a similar manner to that described in Example 2 by reacting 3-oxo-4-azaandrost-5-ene-17β-carboxylic acid and diphenylglycine methyl ester.

Nuclear Magnetic Resonance Spectrum (CDCl$_3$), δ ppm:
 0.59 (3H, singlet);
 1.08 (3H, singlet);
 1.00–2.55 (18H, multiplet);
 3.75 (3H, singlet);
 4.80 (1H, multiplet);
 6.99 (1H, broad);
 7.20–7.45 (11H, multiplet).

Infrared Absorption Spectrum (KBr), ν$_{max}$ cm$^{-1}$: 2966, 2947, 1745, 1681, 1491, 1449, 1242, 1221, 698.

EXAMPLE 75

N-(Diphenylmethyl)-N-methyl-4-methyl-3-oxo-4-aza-5α-androst-1-ene-17β-carboxamide The title compound was prepared in a yield of 55% in a similar manner to that described in Example 20 by reacting N-(diphenylmethyl)-4-methyl-3-oxo-4-aza-5α-androst-1-ene-17β-carboxamide (prepared as described in Example 24) and methyl iodide.

Nuclear Magnetic Resonance Spectrum (CDCl$_3$), δ ppm:
 0.84 (3H, singlet);
 0.93 (3H, singlet);
 0.80–2.45 (16H, multiplet);
 2.85 (3H, singlet);
 2.97 (3H, singlet);
 3.35 (1H, doublet of doublets, J=13 & 4 Hz);
 5.58 (1H, doublet, J=10 Hz);
 6.65 (1H, doublet, J=10 Hz);
 7.10–7.32 (11H, multiplet).

Infrared Absorption Spectrum (KBr), ν$_{max}$ cm$^{-1}$: 2934, 1662, 1639, 1606, 1446, 1396, 1272, 1103, 700.

EXAMPLE 76

N-(Diphenylmethyl)-4-(2-carboxyethyl)-3-oxo-4-aza-5α-androstane-17β-carboxamide 250 mg of N-(diphenylmethyl)-4-(3-hydroxypropyl)-3-oxo-4-aza-5α-androsrane-17β-carboxamide (prepared as described hereafter in Example 77) were dissolved in 10 ml of acetone, and 1 ml of Jones' reagent was added to the solution at 0° C. The reaction mixture was then stirred at 0° C. for 30 minutes, after which isopropyl alcohol was added to it. Insoluble material was filtered off using a Celite (trade mark) filter aid, and the filtrate was condensed by evaporation under reduced pressure. The crystals which precipitated were collected and washed with diethyl ether, to afford 202 mg of the title compound.

Nuclear Magnetic Resonance Spectrum (CDCl$_3$), δ ppm:
0.68 (3H, singlet);
0.88 (3H, singlet);
0.70–2.65 (22H, multiplet);
3.14 (1H, doublet, J=12 Hz);
3.63 (1H, multiplet);
3.83 (1H, multiplet);
5.88 (1H, doublet, J=8 Hz);
6.28 (1H, doublet, J=8 Hz);
7.20–7.40 (10H, multiplet).

Infrared Absorption Spectrum (KBr), $v_{max}$ cm$^{-1}$: 3301, 2942, 1729, 1643, 1622, 1600, 1494, 1449, 1227, 1193, 1029, 699.

EXAMPLE 77

N-(Diphenylmethyl)-4-(3-hydroxypropyl)-3-oxo-4-aza-5α-androstane-17β-carboxamide The title compound was prepared in a yield of 70% in a similar manner to that described in Example 1 by reacting 4-(3-hydroxypropyl)-3-oxo-4-aza-5α-androstane-17β-carboxylic acid and diphenylmethylamine.

Nuclear Magnetic Resonance Spectrum (CDCl$_3$), δ ppm:
0.68 (3H, singlet);
0.90 (3H, singlet);
0.70–2.30 (20H, multiplet);
2.40–2.56 (2H, multiplet);
2.90 (1H, broad);
3.06 (1H, doublet of doublets, J=13 & 4 Hz);
3.40–3.78 (4H, multiplet);
5.87 (1H, doublet, J=8 Hz);
6.30 (1H, doublet, J=8 Hz);
7.18–7.40 (10H, multiplet).

Infrared Absorption Spectrum (KBr), $v_{max}$ cm$^{-1}$: 3309, 2940, 1644, 1618, 1522, 1494, 1448, 1412, 1227, 699.

EXAMPLE 78

N-[1,2-Di(2-thienyl)ethyl]-3-oxo-4-aza-5α-androst-1-ene-17β-carboxamide

The title compound was prepared in a yield of 59% in a similar manner to that desribed in Example 1 by reacting 3-oxo-4-aza-5α-androst-1-ene-17β-carboxylic acid and 1,2-di(2-thienyl)ethylamine.

Nuclear Magnetic Resonance Spectrum (CDCl$_3$), δ ppm:
0.58 & 0.67 (total 3H, each singlet);
0.99 (3H, singlet);
3.25–3.48 (3H, multiplet);
5.47–5.73 (3H, multiplet);
5.84 (1H, doublet of doublets, J=11 & 3 Hz);
6.72–7.25 (7H, multiplet).

Infrared Absorption Spectrum (KBr), $v_{max}$ cm$^{-1}$: 2993, 1675, 1498, 695.

EXAMPLE 79

N-[2-(4-Fluorophenyl)-1-(2-thienyl)ethyl]-3-oxo-4-aza-5α-androst-1-ene-17β-carboxamide The title compound was prepared in a yield of 64% in a similar manner to that described in Example 1 by reacting 3-oxo-4-aza-5α-androst-1-ene-17β-carboxylic acid and 2-(4-fluorophenyl)-1-(2-thienyl)ethylamine.

Nuclear Magnetic Resonance Spectrum (CDCl$_3$), δ ppm:
0.51 & 0.61 (total 3H, each singlet);
0.95 (3H, singlet);
3.08–3.42 (3H, multiplet);
5.35–5.73 (3H, multiplet);
5.82 (1H, doublet of doublets, J=11 & 3 Hz);
6.73–7.23 (8H, multiplet).

Infrared Absorption Spectrum (KBr), $v_{max}$ cm$^{-1}$: 3288, 2934, 1675, 1599, 1509, 1443, 1221, 817, 696.

EXAMPLE 80

N-[2-(4-Methylphenyl)-1-(2-thienyl)ethyl]-3-oxo-4-aza-5α-androst-1-ene-17β-carboxamide The title compound was prepared in a yield of 46% in a similar manner to that described in Example 1 by reacting 3-oxo-4-aza-5α-androst-1-ene-17β-carboxylic acid and 2-(4-methylphenyl)-1-(2-thienyl)ethylamine.

Nuclear Magnetic Resonance Spectrum (CDCl$_3$), δ ppm:
0.45 & 0.58 (total 3H, each singlet);
0.93 (3H, singlet);
2.31 (3H, singlet);
3.0–3.4 (3H, multiplet);
5.3–5.7 (3H, multiplet);
5.82 (1H, doublet of doublets, J=11 & 3 Hz);
6.6–7.2 (8H, multiplet).

Infrared Absorption Spectrum (KBr), $v_{max}$ cm$^{-1}$: 3288, 2932, 1675, 1599, 1515, 1227, 816, 695.

EXAMPLE 81

N-[2-(4-Methoxyphenyl)-1-phenylethyl]-3-oxo-4-aza-5α-androst-1-ene-17β-carboxamide The title compound was prepared in a yield of 44% in a similar manner to that described in Example 1 by reacting 3-oxo-4-aza-5α-androst-1-ene-17β-carboxylic acid and 2-(4-methoxyphenyl)-1-phenylethylamine.

Nuclear Magnetic Resonance Spectrum (CDCl$_3$), δ ppm:
0.52 & 0.53 (total 3H, each singlet);
0.94 & 0.95 (total 3H, each singlet);
2.91–3.18 (2H, multiplet);
3.31 (1H, broad singlet);
3.76 (3H, singlet);
5.15–5.6 (3H, multiplet);
5.82 (1H, doublet of doublets, J=11, 3 Hz);
6.72–7.37 (10H, multiplet).

Infrared Absorption Spectrum (KBr), $v_{max}$ cm$^{-1}$: 2934, 1675, 1600, 1512, 1248, 1177, 817, 699.

EXAMPLE 82

N-[2-(4-Methoxyphenyl)-1-(2-thienyl)ethyl]-3-oxo-4-aza-5α-androst-1-ene-17β-carboxamide The title compound was prepared in a yield of 65% in a similar manner to that described in Example 1 by reacting 3-oxo-4-aza-5α-androst-1-ene-17β-carboxylic acid and 2-(4-methoxyphenyl)-1-(2-thienyl)ethylamine.

Nuclear Magnetic Resonance Spectrum (CDCl$_3$), δ ppm:
 0.47 & 0.58 (total 3H, each singlet);
 0.94 (3H, singlet);
 3.0–3.38 (3H, multiplet);
 3.77 (3H, singlet);
 5.26 (1H, singlet);
 5.20–5.67 (2H, multiplet);
 5.82 (1H, doublet of doublets, J=14 & 6 Hz);
 6.73–7.2 (8H, multiplet).
Infrared Absorption Spectrum (KBr), ν$_{max}$ cm$^{-1}$: 3196, 2931, 1676, 1600, 1513, 1248, 1031, 819.

EXAMPLE 83

N-[2-Phenyl-1-(2-thienyl)ethyl]-3-oxo-4-aza-5α-androstane-17β-carboxamide

The title compound was prepared in a yield of 54% in a similar manner to that described in Example 1 by reacting 3-oxo-4-aza-5α-androstane-17β-carboxylic acid and 2-phenyl-1-(2-thienyl)ethylamine.

Nuclear Magnetic Resonance Spectrum (CDCl$_3$), δ ppm:
 0.46 & 0.61 (total 3H, each singlet);
 1.06 (3H, singlet);
 3.12 (1H, multiplet);
 4.7–5.7 (2H, multiplet);
 6.7–7.4 (8H, multiplet).
Infrared Absorption Spectrum (KBr), ν$_{max}$ cm$^{-1}$: 1665, 1601.

EXAMPLE 84

N-[2-Phenyl-1-(2-thienyl)ethyl]-4-methyl-3-oxo-4-aza-5α-androstane-17β-carboxamide The title compound was prepared in a yield of 20% in a similar manner to that described in Example 20 by reacting N-[2-phenyl-1-(2-thienyl)ethyl]-3-oxo-4-aza-5α-androstane-17β-carboxamide and methyl iodide.

Nuclear Magnetic Resonance Spectrum (CDCl$_3$), δ ppm:
 0.45 & 0.60 (total 3H, each singlet);
 1.07 (3H, singlet);
 2.93 (3H, singlet);
 3.21 (3H, multiplet);
 4.7–5.7 (2H, multiplet);
 6.7–7.4 (8H, multiplet).
Infrared Absorption Spectrum (KBr), ν$_{max}$ cm$^{-1}$: 1666, 1601.

EXAMPLE 85

N-[2-Phenyl-1-(2-thienyl)ethyl]-4-methyl-3-oxo-4-azaandrost-5-ene-17β-carboxamide The title compound was prepared in a yield of 48% in a similar manner to that described in Example 1 by reacting 4-methyl-3-oxo-4-azaandrost-5-ene-17β-carboxylic acid (prepared as described in Preparation 5) and 2-phenyl-1-(2-thienyl)ethylamine.

Nuclear Magnetic Resonance Spectrum (CDCl$_3$), δ ppm:
 0.46 & 0.61 (total 3H, each singlet);
 1.08 (3H, singlet);
 2.92 (3H, singlet);
 4.7–5.7 (3H, multiplet);
 6.7–7.4 (8H, multiplet).
Infrared Absorption Spectrum (KBr), ν$_{max}$ cm$^{-1}$: 1665, 1601.

EXAMPLE 86

N-[2-Phenyl-1-(2-thienyl)ethyl]-3-oxo-4-aza-5α-androst-1-ene-17β-carboxamide

The title compound was prepared in a yield of 58% in a similar manner to that described in Example 1 by reacting 3-oxo-4-aza-5α-androst-1-ene-17β-carboxylic acid and 2-phenyl-1-(2-thienyl)ethylamine.

Nuclear Magnetic Resonance Spectrum (CDCl$_3$), δ ppm:
 0.42 & 0.58 (total 3H, each singlet);
 0.97 (3H, singlet);
 3.05–3.38 (3H, multiplet);
 5.28 (1H, singlet);
 5.37–5.74 (2H, multiplet);
 5.80 (1H, doublet of doublets, J=14 & 5 Hz);
 6.77 (1H, multiplet);
 6.91 (2H, multiplet);
 7.08–7.33 (6H, multiplet).
Infrared Absorption Spectrum (KBr), ν$_{max}$ cm$^{-1}$: 2967, 2933, 1674, 1600, 1469, 1227, 697.

EXAMPLE 87

N-[Bis(4-methoxyphenyl)methyl]-3-oxo-4-aza-5α-androst-1-ene-17β-carboxamide

The title compound was prepared in a yield of 69% in a similar manner to that described in Example 1 by reacting 3-oxo-4-aza-5α-androst-1-ene-17β-carboxylic acid and bis(4-methoxyphenyl)methylamine.

Nuclear Magnetic Resonance Spectrum (CDCl$_3$), δ ppm:
 0.77 (3H, singlet);
 0.97 (3H, singlet);
 3.32 (1H, triplet, J=10 Hz);
 3.78 (3H, singlet);
 3.79 (3H, singlet);
 5.7–5.9 (3H, multiplet);
 6.18 (1H, doublet, J=9 Hz);
 6.7–7.2 (9H, multiplet).
Infrared Absorption Spectrum (KBr), ν$_{max}$ cm$^{-1}$: 2934, 2837, 1678, 1661, 1601, 1509, 1245, 1175, 1034, 818.

EXAMPLE 88

N-[1,2-Di(2-thienyl)ethyl]-3-oxo-4-aza-5α-androstane-17β-carboxamide

The title compound was prepared in a yield of 47% in a similar manner to that described in Example 1 by reacting 3-oxo-4-aza-5α-androstane-17β-carboxylic acid and 1,2-di(2-thienyl)ethylamine.

Nuclear Magnetic Resonance Spectrum (CDCl$_3$), δ ppm:
 0.57 & 0.66 (total 3H, each singlet);
 0.98 (3H, singlet);
 3.21 (1H, multiplet);
 5.4–5.9 (3H, multiplet);
 6.7–7.3 (6H, multiplet).
Infrared Absorption Spectrum (KBr), ν$_{max}$ cm$^{-1}$: 1670, 1601.

EXAMPLE 89

N-[1,2-Di(2-thienyl)ethyl]-4-methyl-3-oxo-4-aza-5α-androstane-17β-carboxamide

The title compound was prepared in a yield of 37% in a similar manner to that described in Example 1 by reacting 4-methyl-3-oxo-4-aza-5α-androstane-17β-carboxylic acid (prepared as described in Preparation 2) and 1,2-di(2-thienyl)ethylamine.

Nuclear Magnetic Resonance Spectrum (CDCl$_3$), δ ppm:
0.56 & 0.66 (total 3H, each singlet);
0.97 (3H, singlet);
2.91 (3H, singlet);
3.12 (1H, multiplet);
5.4–5.9 (2H, multiplet);
6.7–7.3 (6H, multiplet).
Infrared Absorption Spectrum (KBr), ν$_{max}$ cm$^{-1}$: 1670, 1602.

EXAMPLE 90

N-[1,2-Di(2-thienyl)ethyl]-3-oxo-4-azaandrost-5-ene-17β-carboxamide

The title compound was prepared in a yield of 40% in a similar manner to that described in Example 1 by reacting 3-oxo-4-azaandrost-5-ene-17β-carboxylic acid and 1,2-di(2-thienyl)ethylamine.

Nuclear Magnetic Resonance Spectrum (CDCl$_3$), δ ppm:
0.57 & 0.67 (total 3H, each singlet);
0.98 (3H, singlet);
5.4–5.9 (4H, multiplet);
6.7–7.3 (6H, multiplet).
Infrared Absorption Spectrum (KBr), ν$_{max}$ cm$^{-1}$: 1665, 1601.

EXAMPLE 91

N-[1,2-Di(2-thienyl)ethyl]-4-methyl-3-oxo-4-azaandrost-5-ene-17β-carboxamide

The title compound was prepared in a yield of 49% in a similar manner to that described in Example 1 by reacting 4-methyl-3-oxo-4-azaandrost-5-ene-17β-carboxylic acid (prepared as described in Preparation 5) and 1,2-di(2-thienyl)ethylamine.

Nuclear Magnetic Resonance Spectrum (CDCl$_3$), δ ppm:
0.56 & 0.66 (total 3H, each singlet);
0.97 (3H, singlet);
2.93 (3H, singlet);
5.4–5.9 (3H, multiplet);
6.7–7.3 (6H, multiplet).
Infrared Absorption Spectrum (KBr), ν$_{max}$ cm$^{-1}$: 1665, 1600.

EXAMPLE 92

N-[α-(4-Methoxyphenyl)benzyl]-3-oxo-4-aza-5α-androst-1-ene-17β-carboxamide

The title compound was prepared in a yield of 66% in a similar manner to that described in Example 1 by reacting 3-oxo-4-aza-5α-androst-1-ene-17β-carboxylic acid and α-(4-methoxyphenyl)benzylamine.

Nuclear Magnetic Resonance Spectrum (CDCl$_3$), δ ppm:
0.69 (3H, singlet);
1.00 (3H, singlet);
3.36 (1H, multiplet);
3.60 (3H, singlet);
5.73 (1H, broad singlet);
5.84 (2H, multiplet);
6.23 (1H, doublet, J=8 Hz);
6.78–7.38 (10H, multiplet).
Infrared Absorption Spectrum (KBr), ν$_{max}$ cm$^{-1}$: 2935, 1678, 1511, 1248, 818, 699.

EXAMPLE 93

N-[α-(4-Methoxyphenyl)benzyl]-3-oxo-4-aza-5α-androstane-17β-carboxamide

The title compound was prepared in a yield of 40% in a similar manner to that described in Example 1 by reacting 3-oxo-4-aza-5α-androstane-17β-carboxylic acid and α-(4-methoxyphenyl)benzylamine.

Nuclear Magnetic Resonance Spectrum (CDCl$_3$), δ ppm:
0.67 (3H, singlet);
0.89 (3H, singlet);
0.70–2.70 (20H, multiplet).
3.05 (1H, doublet of doublets, J=11 & 4 Hz);
5.68 (1H, broad);
5.83 (1H, doublet, J=7 Hz);
6.22 (1H, doublet, J=7 Hz);
6.82–6.88 (2H, multiplet);
7.10–7.36 (7H, multiplet).
Infrared Absorption Spectrum (KBr), ν$_{max}$ cm$^{-1}$: 3304, 2935, 1664, 1511, 1248, 1033, 700.

EXAMPLE 94

N-[α-(4-Methoxyphenyl)benzyl]-4-methyl-3-oxo-4-aza-5α-androstane-17β-carboxamide The title compound was prepared in a yield of 46% in a similar manner to that described in Example 1 by reacting 4-methyl-3-oxo-4-aza-5α-androstane-17β-carboxylic acid (prepared as described in Preparation 2) and α-(4-methoxyphenyl)benzylamine.

Nuclear Magnetic Resonance Spectrum (CDCl$_3$), δ ppm:
0.67 (3H, singlet);
0.88 (3H, singlet);
0.70–2.30 (16H, multiplet);
2.41–2.46 (2H, multiplet).
2.92 (3H, singlet);
3.02 (1H, doublet of doublets, J=13 & 3 Hz);
3.79 (3H, singlet);
5.83 (1H, doublet, J=8 Hz);
6.22 (1H, doublet, J=8 Hz);
6.83–6.87 (2H, multiplet);
7.11–7.35 (7H, multiplet).
Infrared Absorption Spectrum (KBr), ν$_{max}$ cm$^{-1}$: 3306, 2936, 1644, 1624, 1511, 1248, 1034, 699.

EXAMPLE 95

N-[α-(4-Methoxyphenyl)benzyl]-3-oxo-4-azaandrost-5-ene-17β-carboxamide

The title compound was prepared in a yield of 57% in a similar manner to that described in Example 1 by reacting 3-oxo-4-azaandrost-5-ene-17β-carboxylic acid and α-(4-methoxyphenyl)benzylamine.

Nuclear Magnetic Resonance Spectrum (CDCl$_3$), δ ppm:
0.70 (3H, singlet);
1.09 (3H, singlet);
1.05–2.70 (19H, multiplet);
3.79 (3H, singlet);

4.80–4.82 (1H, multiplet);
5.85 (1H, doublet, J=8 Hz);
6.23 (1H, doublet, J=8 Hz);
6.83–6.88 (2H, multiplet);
7.11–7.40 (7H, multiplet).

Infrared Absorption Spectrum (KBr), $v_{max}$ cm$^{-1}$: 1661, 1511, 1249, 1033, 700.

EXAMPLE 96

N-[α-(4-Methoxyphenyl)benzyl]-4-methyl-3-oxo-4-azaandrost-5-ene-17β-carboxamide

The title compound was prepared in a yield of 47% in a similar manner to that described in Example 1 by reacting 4-methyl-3-oxo-4-azaandrost-5-ene-17β-carboxylic acid (prepared as described in Preparation 5) and α-(4-methoxyphenyl)benzylamine.

Nuclear Magnetic Resonance Spectrum (CDCl$_3$), δ ppm:
0.70 (3H, singlet);
1.04 (3H, singlet);
1.10–2.30 (16H, multiplet);
2.49–2.54 (2H, multiplet);
3.11 (3H, singlet);
3.79 (3H, singlet);
5.01–5.04 (1H, multiplet);
5.85 (1H, doublet, J=8 Hz);
6.23 (1H, doublet, J=8 Hz);
6.83–6.87 (2H, multiplet);
7.12–7.35 (7H, multiplet).

Infrared Absorption Spectrum (KBr), $v_{max}$ cm$^{-1}$: 3312, 2945, 1669, 1644, 1511, 1248, 1033, 700.

EXAMPLE 97

N-[2-Phenyl-1-(2-thienyl)ethyl]-3-oxo-4-azaandrost-5-ene-17β-carboxamide

The title compound was prepared in a yield of 45% in a similar manner to that described in Example 1 by reacting 3-oxo-4-azaandrost-5-ene-17β-carboxylic acid and 2-phenyl-1-(2-thienyl)ethylamine.

Nuclear Magnetic Resonance Spectrum (CDCl$_3$), δ ppm:
0.45 & 0.61 (total 3H, each singlet);
1.07 (3H, singlet);
4.7–5.7 (4H, multiplet);
6.7–7.4 (8H, multiplet).

Infrared Absorption Spectrum (KBr), $v_{max}$ cm$^{-1}$: 1663, 1602.

EXAMPLE 98

N-[(S)-1,2-Diphenylethyl]-3-oxo-4-aza-5α-androst-1-ene-17β-carboxamide

The title compound was prepared in a yield of 91% in a similar manner to that described in Example 1 by reacting 3-oxo-4-aza-5α-androst-1-ene-17β-carboxylic acid and (S)-1,2-diphenylethylamine.

Nuclear Magnetic Resonance Spectrum (CDCl$_3$), δ ppm:
0.51 (3H, singlet);
0.94 (3H, singlet);
0.90–2.20 (16H, multiplet);
3.00–3.11 (2H, multiplet);
3.31 (1H, triplet, J=8 Hz);
5.22–5.31 (1H, multiplet);
5.47 (1H, broad);
5.59 (1H, doublet, J=7 Hz);
5.80 (1H, doublet, J=10 Hz);
6.77 (1H, doublet, J=10 Hz);
7.00–7.35 (10H, multiplet).

Infrared Absorption Spectrum (KBr), $v_{max}$ cm$^{-1}$: 3225, 2931, 1667, 1602, 1495, 1475, 1453, 1220, 825, 698.

EXAMPLE 99

N-[(S)-1,2-Diphenylethyl]-3-oxo-4-azaandrost-5-ene-17β-carboxamide

The title compound was prepared in a yield of 92% in a similar manner to that described in Example 1 by reacting 3-oxo-4-azaandrost-5-ene-17β-carboxylic acid and (S)-1,2-diphenylethylamine.

Nuclear Magnetic Resonance Spectrum (CDCl$_3$), δ ppm:
0.54 (3H, singlet);
1.07 (3H, singlet);
0.80–2.60 (18H, multiplet);
3.00–3.20 (2H, multiplet);
4.77–4.80 (1H, multiplet);
5.23–5.31 (1H, multiplet);
5.60 (1H, doublet, J=7 Hz);
7.00–7.40 (10H, multiplet).

Infrared Absorption Spectrum (KBr), $v_{max}$ cm$^{-1}$: 2943, 1677, 1660, 1640, 1518, 1496, 1454, 1386, 1223, 699.

EXAMPLE 100

N-[(S)-1,2-Diphenylethyl]-4-methyl-3-oxo-4-aza-5α-androstane-17β-carboxamide

The title compound was prepared in a yield of 77% in a similar manner to that described in Example 1 by reacting 4-methyl-3-oxo-4-aza-5α-androstane-17β-carboxylic acid (prepared as described in Preparation 2) and (S)-1,2-diphenylethylamine.

Nuclear Magnetic Resonance Spectrum (CDCl$_3$), δ ppm:
0.50 (3H, singlet);
0.85 (3H, singlet);
0.70–2.20 (18H, multiplet);
2.40–2.50 (2H, multiplet);
2.92 (3H, singlet);
2.99–3.17 (3H, singlet);
5.26 (1H, quartet, J=7 Hz);
5.58 (1H, doublet, J=7 Hz);
7.03–7.34 (10H, multiplet).

Infrared Absorption Spectrum (KBr), $v_{max}$ cm$^{-1}$: 3318, 2941, 1645, 1528, 1495, 1454, 1393, 1305, 1228, 1031, 757, 700.

EXAMPLE 101

N-[(S)-1,2-Diphenylethyl]-4-methyl-3-oxo-4-aza-5α-androst-1-ene-17β-carboxamide

The title compound was prepared in a yield of 90% in a similar manner to that described in Example 1 by reacting 4-methyl 3-oxo-4-aza-5α-androst-1-ene-17β-carboxylic acid (prepared as described in Preparation 4) and (S)-1,2-diphenylethylamine.

Nuclear Magnetic Resonance Spectrum (CDCl$_3$), δ ppm:
0.51 (3H, singlet);
0.89 (3H, singlet);
0.90–2.20 (16H, multiplet);
2.94 (3H, singlet);
3.33 (1H, doublet of doublets, J=13 & 4 Hz);
5.22–5.31 (1H, multiplet);
5.59 (1H, doublet, J=7 Hz);

EXAMPLE 102

N-[(S)-1,2-Diphenylethyl]-4-methyl-3-oxo-4-azaandrost-5-ene-17β-carboxamide

The title compound was prepared in a yield of 91% in a similar manner to that described in Example 1 by reacting 4-methyl-3-oxo-4-azaandrost-5-ene-17β-carboxylic acid (prepared as described in Preparation 5) and (S)-1,2-diphenylethylamine.

Nuclear Magnetic Resonance Spectrum (CDCl$_3$), δ ppm:
 0.53 (3H, singlet);
 1.01 (3H, singlet);
 0.90–2.30 (16H, multiplet);
 2.49–2.54 (2H, multiplet);
 3.11 (3H, singlet);
 3.05–3.20 (2H, multiplet);
 5.00–5.03 (1H, multiplet);
 5.27 (1H, quartet, J=7 Hz);
 5.60 (1H, doublet, J=7 Hz);
 7.00–7.40 (10H, multiplet).

Infrared Absorption Spectrum (KBr), ν$_{max}$ cm$^{-1}$: 3402, 2949, 1648, 1624, 1520, 1468, 1361, 1267, 760, 700.

EXAMPLE 103

N-[(R)-1,2-Diphenylethyl]-3-oxo-4-aza-5α-androst-1-ene-17β-carboxamide

The title compound was prepared in a yield of 73% in a similar manner to that described in Example 1 by reacting 3-oxo-4-aza-5α-androst-1-ene-17β-carboxylic acid and (R)-1,2-diphenylethylamine.

Nuclear Magnetic Resonance Spectrum (CDCl$_3$), δ ppm:
 0.46 (3H, singlet);
 0.95 (3H, singlet);
 0.90–1.80 (14H, multiplet);
 2.00–2.25 (2H, multiplet);
 2.95–3.23 (2H, multiplet);
 3.31 (1H, triplet, J=7 Hz);
 5.30–5.55 (3H, multiplet);
 5.82 (1H, doublet, J=10 Hz);
 6.79 (1H, doublet, J=10 Hz);
 7.10–7.40 (10H, multiplet).

Infrared Absorption Spectrum (KBr), ν$_{max}$ cm$^{-1}$: 3214, 2936, 1676, 1601, 1528, 1495, 1453, 1229, 818, 698.

EXAMPLE 104

N-[(R)-1,2-Diphenylethyl]-3-oxo-4-azaandrost-5-ene-17β-carboxamide

The title compound was prepared in a yield of 80% in a similar manner to that described in Example 1 by reacting 3-oxo-4-azaandrost-5-ene-17β-carboxylic acid and (R)-1,2-diphenylethylamine.

Nuclear Magnetic Resonance Spectrum (CDCl$_3$), δ ppm:
 0.49 (3H, singlet);
 1.08 (3H, singlet);
 0.90–2.30 (16H, multiplet);
 2.40–2.60 (2H, multiplet);
 2.90–3.25 (2H, multiplet);
 4.67–4.79 (1H, multiplet);
 5.84 (1H, doublet, J=10 Hz);
 6.65 (1H, doublet, J=10 Hz);
 7.00–7.40 (10H, multiplet).

Infrared Absorption Spectrum (KBr), ν$_{max}$ cm$^{-1}$: 3320, 2941, 1659, 1603, 1525, 1495, 1453, 1226, 820, 699.

EXAMPLE 105

N-[(R)-1,2-Diphenylethyl]-4-methyl-3-oxo-4-aza-5α-androstane-17β-carboxamide

The title compound was prepared in a yield of 96% in a similar manner to that described in Example 1 by reacting 4-methyl-3-oxo-4-aza-5α-androstane-17β-carboxylic acid (prepared as described in Preparation 2) and (R)-1,2-diphenylethylamine.

Nuclear Magnetic Resonance Spectrum (CDCl$_3$), δ ppm:
 0.46 (3H, singlet);
 0.87 (3H, singlet);
 0.70–2.20 (18H, multiplet);
 2.30–2.50 (3H, multiplet);
 2.92 (3H, singlet);
 2.95–3.20 (3H, multiplet);
 5.29–5.37 (1H, multiplet);
 5.48 (1H, doublet, J=7 Hz);
 7.05–7.40 (10H, multiplet).

Infrared Absorption Spectrum (KBr), ν$_{max}$ cm$^{-1}$: 3317, 2939, 1645, 1527, 1495, 1453, 1392, 1305, 1228, 1032, 699.

EXAMPLE 106

N-[(R)-1,2-Diphenylethyl]-4-methyl-3-oxo-4-aza-5α-androst-1-ene-17β-carboxamide

The title compound was prepared in a yield of 86% in a similar manner to that described in Example 1 by reacting 4-methyl-3-oxo-4-aza-5α-androst-1-ene-17β-carboxylic acid (prepared as described in Preparation 4) and (R)-1,2-diphenylethylamine.

Nuclear Magnetic Resonance Spectrum (CDCl$_3$), δ ppm:
 0.46 (3H, singlet);
 0.90 (3H, singlet);
 0.80–2.25 (16H, multiplet);
 2.95 (3H, singlet);
 2.90–3.40 (3H, multiplet);
 5.29–5.38 (1H, multiplet);
 5.49 (1H, doublet, J=7 Hz);
 5.88 (1H, doublet, J=9 Hz);
 6.69 (1H, doublet, J=9 Hz);
 7.10–7.40 (10H, multiplet).

Infrared Absorption Spectrum (KBr), ν$_{max}$ cm$^{-1}$: 3323, 2940, 1663, 1603, 1526, 1495, 1453, 1227, 820, 699.

EXAMPLE 107

N-[(R)-1,2-Diphenylethyl]-4-methyl-3-oxo-4-azaandrost-5-ene-17β-carboxamide

The title compound was prepared in a yield of 82% in a similar manner to that described in Example 1 by reacting 4-methyl-3-oxo-4-azaandrost-5-ene-17β-carboxylic acid (prepared as described in Preparation 5) and (R)-1,2-diphenylethylamine.

Nuclear Magnetic Resonance Spectrum (CDCl$_3$), δ ppm:
 0.49 (3H, singlet);
 1.03 (3H, singlet);
 0.90–2.30 (16H, multiplet);
 2.50–2.60 (2H, multiplet);

3.11 (3H, multiplet);
2.99-3.20 (2H, multiplet);
5.00-5.03 (1H, multiplet);
5.30-5.38 (1H, multiplet);
5.50 (1H, doublet, J=7 Hz);
7.10-7.40 (10H, multiplet).

Infrared Absorption Spectrum (KBr), $\nu_{max}$ cm$^{-1}$:
3434, 2940, 1672, 1663, 1649, 1495, 1453, 1389, 758, 701.

EXAMPLE 108

N-[1-Methyl-1-(2-thienyl)ethyl]-3-oxo-4-aza-5α-androst-1-ene-17β-carboxamide

The title compound was prepared in a yield of 27% in a similar manner to that described in Example 2 by reacting 3-oxo-4-aza-5α-androst-1-ene-17β-carboxylic acid and 1-methyl-1-(2-thienyl)ethylamine.

Nuclear Magnetic Resonance Spectrum (CDCl$_3$), δ ppm:
0.68 (3H, singlet);
0.97 (3H, singlet);
0.90-1.85 (16H, multiplet);
1.81 (3H, singlet);
1.82 (3H, singlet);
2.02-2.07 (2H, multiplet);
3.32 (1H, triplet, J=9 Hz);
5.39 (1H, broad);
5.53 (1H, singlet);
5.81 (1H, doublet, J=10 Hz);
6.79 (1H, doublet, J=10 Hz);
6.91-6.99 (2H, multiplet);
7.16-7.19 (1H, multiplet).

Infrared Absorption Spectrum (KBr), $\nu_{max}$ cm$^{-1}$:
3253, 2931, 1675, 1656, 1596, 1489, 1453, 818, 700.

EXAMPLE 109

N-[1-Methyl-1-(2-thienyl)ethyl]-4-methyl-3-oxo-4-aza-5α-androstane-17β-carboxamide The title compound was prepared in a yield of 42% in a similar manner to that described in Example 2 by reacting 4-methyl-3-oxo-4-aza-5α-androstane-17β-carboxylic acid (prepared as described in Preparation 2) and 1-methyl-1-(2-thienyl)ethylamine.

Nuclear Magnetic Resonance Spectrum (CDCl$_3$), δ ppm:
0.67 (3H, singlet);
0.88 (3H, singlet);
0.70-2.25 (18H, multiplet);
1.81 (3H, singlet);
1.82 (3H, singlet);
2.42-2.47 (2H, multiplet);
2.92 (3H, singlet);
3.02 (1H, doublet of doublets, J=12 & 3 Hz);
5.51 (1H, singlet);
6.91-6.99 (2H, multiplet);
7.16-7.18 (1H, multiplet).

Infrared Absorption Spectrum (KBr), $\nu_{max}$ cm$^{-1}$:
3312, 2943, 1671, 1627, 1537, 1526, 1383, 1227, 707.

EXAMPLE 110

N-[1-Methyl-1-(2-thienyl)ethyl]-4-methyl-3-oxo-4-aza-5α-androst-1-ene-17β-carboxamide The title compound was prepared in a yield of 26% in a similar manner to that described in Example 2 by reacting 4-methyl-3-oxo-4-aza-5α-androst-1-ene-17β-carboxylic acid (prepared as described in Preparation 4) and 1-methyl-1-(2-thienyl)ethylamine.

Nuclear Magnetic Resonance Spectrum (CDCl$_3$), δ ppm:
0.68 (3H, singlet);
0.92 (3H, singlet);
0.90-1.86 (12H, multiplet);
1.81 (3H, singlet);
1.82 (3H, singlet);
1.96-2.17 (4H, multiplet);
2.95 (3H, singlet);
3.34 (1H, doublet of doublets, J=13 & 3 Hz);
5.52 (1H, singlet);
5.86 (1H, doublet, J=10 Hz);
6.68 (1H, doublet, J=10 Hz);
6.91-6.99 (2H, multiplet);
7.16-7.19 (1H, multiplet).

Infrared Absorption Spectrum (KBr), $\nu_{max}$ cm$^{-1}$:
3323, 2967, 2941, 1658, 1604, 1540, 1245, 821.

EXAMPLE 111

N-[1-Methyl-1-(2-thienyl)ethyl]-4-methyl-3-oxo-4-azaandrost-5-ene-17β-carboxamide The title compound was prepared in a yield of 50% in a similar manner to that described in Example 2 by reacting 4-methyl-3-oxo-4-azaandrost-5-ene-17β-carboxylic acid (prepared as described in Preparation 5) and 1-methyl-1-(2-thienyl)ethylamine.

Nuclear Magnetic Resonance Spectrum (CDCl$_3$), δ ppm:
0.71 (3H, singlet);
1.05 (3H, singlet);
1.05-2.29 (16H, multiplet);
1.82 (3H, singlet);
1.83 (3H, singlet);
2.50-2.55 (2H, multiplet);
3.11 (3H, singlet);
5.01-5.04 (1H, multiplet);
5.54 (1H, singlet);
6.91-7.00 (2H, multiplet);
7.16-7.19 (1H, multiplet).

Infrared Absorption Spectrum (KBr), $\nu_{max}$ cm$^{-1}$:
3321, 2966, 1677, 1636, 1522, 1383, 1247, 688.

EXAMPLE 112

N-[α-(4-Hydroxyphenyl)benzyl]-4-methyl-3-oxo-4-aza-5α-androst-1-ene-17β-carboxamide The title compound was prepared in a yield of 90% in a similar manner to that described in Example 37 by reacting 4-methyl-3-oxo-4-aza-5α-androst-1-ene-17β-carboxylic acid (prepared as described in Preparation 4) and α-(4-hydroxyphenyl)benzylamine.

Nuclear Magnetic Resonance Spectrum (CDCl$_3$+CD$_3$OD), δ ppm:
0.67 (3H, singlet);
0.91 (3H, singlet);
0.93-2.03 (16H, multiplet);
2.18-2.22 (2H, multiplet);
2.94 (3H, singlet);
3.35 (1H, doublet of doublets, J=13 & 3 Hz);
5.83 (1H, doublet, J=10 Hz);
6.16 (1H, singlet);
6.70 (1H, doublet, J=10 Hz);
6.75-6.80 (2H, multiplet);
7.01-7.06 (2H, multiplet);
7.20-7.35 (5H, multiplet).

Infrared Absorption Spectrum (KBr), $\nu_{max}$ cm$^{-1}$:
3274, 2943, 1641, 1615, 1599, 1514, 820, 703.

EXAMPLE 113

N-[α-(4-Hydroxyphenyl)benzyl]-4-methyl-3-oxo-4-azaandrost-5-ene-17β-carboxamide

The title compound was prepared in a yield of 25% in a similar manner to that described in Example 37 by reacting 4-methyl-3-oxo-4-azaandrost-5-ene-17β-carboxylic acid (prepared as described in Preparation 5) and α-(4-hydroxyphenyl)benzylamine.

Nuclear Magnetic Resonance Spectrum (CDCl$_3$), δ ppm:

0.70 (3H, singlet);
1.04 (3H, singlet);
1.07–2.30 (17H, multiplet);
2.49–2.55 (2H, multiplet);
3.12 (3H, singlet);
5.04 (1H, doublet of doublets, J=5 & 2 Hz);
5.87 (1H, doublet, J=8 Hz);
6.20 (1H, doublet, J=8 Hz);
6.73–6.78 (2H, multiplet);
7.02–7.07 (2H, multiplet);
7.22–7.36 (5H, multiplet).

Infrared Absorption Spectrum (KBr), ν$_{max}$ cm$^{-1}$: 3282, 2946, 1628, 1595, 1517, 1452, 1274, 1239, 701.

EXAMPLE 114

N-[(S)-1-Phenyl-2-(4-methylphenyl)ethyl]-3-oxo-4-aza-5α-androst-1-ene-17β-carboxamide The title compound was prepared in a yield of 71% in a similar manner to that described in Example 1 by reacting 3-oxo-4-aza-5α-androst-1-ene-17β-carboxylic acid and (S)-1-phenyl-2-(4-methylphenyl)ethylamine.

Nuclear Magnetic Resonance Spectrum (CDCl$_3$), δ ppm:

0.51 (3H, singlet);
0.94 (3H, singlet);
0.90–2.20 (16H, multiplet);
2.28 (3H, singlet);
3.00–3.07 (2H, multiplet);
3.31 (1H, triplet, J=7 Hz);
5.23 (1H, doublet of doublets, J=14 & 7 Hz);
5.40 (1H, broad);
5.58 (1H, doublet, J=7 Hz);
5.80 (1H, doublet, J=10 Hz);
6.77 (1H, doublet, J=10 Hz);
6.93 (2H, doublet, J=8 Hz);
7.03 (2H, doublet, J=8 Hz);
7.19–7.33 (5H, multiplet).

Infrared Absorption Spectrum (KBr), ν$_{max}$ cm$^{-1}$: 3438, 3226, 2931, 1683, 1676, 1607, 1475, 698.

EXAMPLE 115

N-[(S)-1-Phenyl-2-(4-methylphenyl)ethyl]-3-oxo-4-azaandrost-5-ene-17β-carboxamide The title compound was prepared in a yield of 81% in a similar manner to that described in Example 1 by reacting 3-oxo-4-azaandrost-5-ene-17β-carboxylic acid and (S)-1-phenyl-2-(4-methylphenyl)ethylamine.

Nuclear Magnetic Resonance Spectrum (CDCl$_3$), δ ppm:

0.54 (3H, singlet);
1.07 (3H, singlet);
1.00–2.60 (19H, multiplet);
2.28 (3H, singlet);
3.00–3.09 (2H, multiplet);
4.76–4.79 (1H, multiplet);
5.24 (1H, doublet of doublets, J=14 & 7 Hz);
5.58 (1H, doublet, J=7 Hz);
6.93 (2H, doublet, J=8 Hz);
7.03 (2H, doublet, J=8 Hz);
7.17–7.33 (5H, multiplet).

Infrared Absorption Spectrum (KBr), ν$_{max}$ cm$^{-1}$: 3420, 3140, 2944, 1678, 1660, 1637, 1518, 707.

EXAMPLE 116

N-[(S)-1-Phenyl-2-(4-methylphenyl)ethyl]-4-methyl-3-oxo-4-aza-5α-androst-1-ene-17β-carboxamide The title compound was prepared in a yield of 50% in a similar manner to that described in Example 1 by reacting 4-methyl-3-oxo-4-aza-5α-androst-1-ene-17β-carboxylic acid (prepared as described in Preparation 4) and (S)-1-phenyl-2-(4-methylphenyl)ethylamine.

Nuclear Magnetic Resonance Spectrum (CDCl$_3$), δ ppm:

0.51 (3H, singlet);
0.89 (3H, singlet);
0.80–2.20 (16H, multiplet);
2.28 (3H, singlet);
2.94 (3H, singlet);
3.02–3.07 (2H, multiplet);
3.33 (1H, doublet of doublets, J=13 & 3 Hz);
5.20–5.30 (1H, multiplet);
5.57 (1H, doublet, J=7 Hz);
5.87 (2H, doublet, J=10 Hz);
6.66 (1H, doublet, J=10 Hz);
6.93 (2H, doublet, J=8 Hz);
7.03 (2H, doublet, J=8 Hz);
7.19–7.33 (5H, multiplet).

Infrared Absorption Spectrum (KBr), ν$_{max}$ cm$^{-1}$: 3359, 2945, 1651, 1598, 1525, 1448, 700.

EXAMPLE 117

N-[(S)-1-Phenyl-2-(4-methylphenyl)ethyl]-4-methyl-3-oxo-4-azaandrost-5-ene-17β-carboxamide The title compound was prepared in a yield of 58% in a similar manner to that described in Example 1 by reacting 4-methyl-3-oxo-4-azaandrost-5-ene-17β-carboxylic acid (prepared as described in Preparation 5) and (S)-1-phenyl-2-(4-methylphenyl)ethylamine.

Nuclear Magnetic Resonance Spectrum (CDCl$_3$), δ ppm:

0.53 (3H, singlet);
1.01 (3H, singlet);
1.05–2.27 (16H, multiplet);
2.28 (3H, singlet);
2.49–2.54 (2H, multiplet);
3.03–3.07 (2H, multiplet);
3.11 (3H, singlet);
5.02 (1H, doublet of doublets, J=5 & 2 Hz);
5.24 (1H, doublet of doublets, J=15 & 7 Hz);
5.58 (1H, doublet, J=7 Hz);
6.93 (2H, doublet, J=8 Hz);
7.03 (2H, doublet, J=8 Hz);
7.19–7.33 (5H, multiplet).

Infrared Absorption Spectrum (KBr), ν$_{max}$ cm$^{-1}$: 3396, 2945, 1665, 1645, 1627, 1519, 1471, 704.

EXAMPLE 118

N-(Diphenylmethyl)-3-oxo-4-aza-5α-androst-1-ene-17β-carboxamide 640 mg of N-diphenylmethyl-3-oxo-4-aza-5α-androstane-17βcarboxamide were dissolved in 20 ml of dry dioxane, and 310 mg of 2,3-dichloro-5,6-dicyano-p-benzoquinone and 1356 mg of N,O-bis(trimethylsilyl)trifluoroacetamide were added to the resulting solution. The reaction solution was then stirred at room temperature for 4 hours, after which it was heated under reflux for 13 hours. The reaction mixture was then cooled to room temperature and diluted with 100 ml of methylene chloride. It was then washed with 1N aqueous hydrochloric acid, with water, with an aqueous solution of sodium hydrogencarbonate and with a saturated aqueous solution of sodium chloride, in that order, after which it was dried over anhydrous magnesium sulfate and condensed by evaporation under reduced pressure. The resulting residue was purified by column chromatography through 15 g of silica gel. Gradient elution with mixtures of acetone and methylene chloride ranging from 1:9 to 2:3 by volume afforded 360 mg of the title compound.

The Nuclear Magnetic Resonance and Infrared spectra of the title compound are identical to those of the product prepared as described in Example 7.

EXAMPLE 119

N-[1-(4-Acetamidophenyl)-1-methylethyl]-3-oxo-4-aza-5α-androstane-17β-carboxamide The title compound was prepared in a yield of 73% in a similar manner to that described in Example 37 by reacting 3-oxo-4-aza-5α-androstane-17β-carboxylic acid and 4-(1-amino-1-methylethyl)acetanilide.

Nuclear Magnetic Resonance Spectrum ($CDCl_3 + CD_3OD$), δ ppm:
0.65 (3H, singlet);
0.89 (3H, singlet);
0.75-2.20 (18H, multiplet);
1.65 (3H, singlet);
1.68 (3H, singlet);
2.13 (3H, singlet);
2.37-2.43 (2H, multiplet);
3.05 (1H, doublet of doublets, J=12 & 4 Hz);
7.31 (2H, doublet, J=8 Hz);
7.45 (2H, doublet, J=8 Hz).

Infrared Absorption Spectrum (KBr), $v_{max}$ cm$^{-1}$: 3303, 3194, 2940, 2917, 1698, 1672, 1609, 1546, 1495, 1405, 829, 560.

EXAMPLE 120

N-[1-(4-Acetamidophenyl)-1-methylethyl]-3-oxo-4-aza-5α-androst-1-ene-17β-carboxamide The title compound was prepared in a yield of 59% in a similar manner to that described in Example 37 by reacting 3-oxo-4-aza-5α-androst-1-ene-17β-carboxylic acid and 4-(1-amino-1-methylethyl)acetanilide.

Nuclear Magnetic Resonance Spectrum ($CDCl_3 + CD_3OD$), δ ppm:
0.66 (3H, singlet);
0.97 (3H, singlet);
1.00-2.20 (16H, multiplet);
1.66 (3H, singlet);
1.68 (3H, singlet);
2.13 (3H, singlet);
3.32 (1H, doublet of doublets, J=9 & 6 Hz);
5.80 (1H, doublet, J=10 Hz);
6.82 (1H, doublet, J=10 Hz);
7.32 (2H, doublet, J=9 Hz);
7.45 (2H, doublet, J=9 Hz).

Infrared Absorption Spectrum (KBr), $v_{max}$ cm$^{-1}$: 3305, 3193, 2936, 1707, 1672, 1606, 1545, 1495, 1321, 822, 561.

EXAMPLE 121

N-[1-(4-Acetamidophenyl)-1-methylethyl]-3-oxo-4-azaandrost-5-ene-17β-carboxamide The title compound was prepared in a yield of 50% in a similar manner to that described in Example 37 by reacting 3-oxo-4-azaandrost-5-ene-17β-carboxylic acid and 4-(1-amino-1-methylethyl)acetanilide.

Nuclear Magnetic Resonance Spectrum ($CDCl_3 + CD_3OD$), δ ppm:
0.68 (3H, singlet);
1.10 (3H, singlet);
1.00-2.50 (18H, multiplet);
1.66 (3H, singlet);
1.68 (3H, singlet);
2.18 (3H, singlet);
7.32 (2H, doublet, J=9 Hz);
7.45 (2H, doublet, J=9 Hz).

Infrared Absorption Spectrum (KBr), $v_{max}$ cm$^{-1}$: 3300, 3194, 2939, 1705, 1671, 1610, 1574, 1495, 1387, 1322, 1225, 830, 561.

EXAMPLE 122

N-[1-(4-Acetamidophenyl)-1-methylethyl]-4-methyl-3-oxo-4-aza-5α-androstane-17β-carboxamide The title compound was prepared in a yield of 40% in a similar manner to that described in Example 37 by reacting 4-methyl-3-oxo-4-aza-5α-androstane-17β-carboxylic acid (prepared as described in Preparation 2) and 4-(1-amino-1-methylethyl)acetanilide.

Nuclear Magnetic Resonance Spectrum ($CDCl_3$), δ ppm:
0.66 (3H, singlet);
0.90 (3H, singlet);
0.75-2.50 (21H, multiplet);
1.67 (3H, singlet);
1.69 (3H, singlet);
2.15 (3H, singlet);
2.93 (3H, singlet);
3.04 (1H, doublet of doublets, J=12 & 3 Hz);
5.54 (1H, broad);
7.33 (2H, doublet, J=8 Hz);
7.42 (2H, doublet, J=8 Hz).

Infrared Absorption Spectrum (KBr), $v_{max}$ cm$^{-1}$: 3305, 2938, 1688, 1673, 1623, 1530, 1398, 1318, 1252, 834, 557.

EXAMPLE 123

N-[1-(4-Acetamidophenyl)-1-methylethyl]-4-methyl-3-oxo-4-aza-5α-androst-1-ene-7β-carboxamide The title compound was prepared in a yield of 67% in a similar manner to that described in Example 37 by reacting 4-methyl-3-oxo-4-aza-5α-androst-1-ene-17β-carboxylic acid (prepared as described in Preparation 4) and 4-(1-amino-1-methylethyl)acetanilide.

Nuclear Magnetic Resonance Spectrum ($CDCl_3$), δ ppm:
0.67 (3H, singlet);
0.93 (3H, singlet);
0.90-2.20 (17H, multiplet);
1.67 (3H, singlet);
1.70 (3H, singlet);
2.17 (3H, singlet);

2.96 (3H, singlet);
3.35 (1H, doublet of doublets, J=13 & 3 Hz);
5.54 (1H, broad);
5.89 (1H, doublet, J=10 Hz);
6.69 (1H, doublet, J=10 Hz);
7.33 (2H, doublet, J=8 Hz);
7.42 (2H, doublet, J=8 Hz).

Infrared Absorption Spectrum (KBr), $\nu_{max}$ cm$^{-1}$: 3309, 2971, 2936, 1689, 1675, 1605, 1534, 1315, 1256, 824.

EXAMPLE 124

N-[1-(4-Acetamidophenyl)-1-methylethyl]-4-methyl-3-oxo-4-azaandrost-5-ene-17β-carboxamide The title compound was prepared in a yield of 61% in a similar manner to that described in Example 37 by reacting 4-methyl-3-oxo-4-azaandrost-5-ene-17β-carboxylic acid (prepared as described in Preparation 5) and 4-(1-amino-1-methylethyl)acetanilide.

Nuclear Magnetic Resonance Spectrum (CDCl$_3$), δ ppm:
0.69 (3H, singlet);
1.63 (3H, singlet);
1.00-2.30 (17H, multiplet);
1.67 (3H, singlet);
1.70 (3H, singlet);
2.15 (3H, singlet);
2.50-2.58 (2H, multiplet);
3.12 (3H, singlet);
5.04 (1H, doublet of doublets, J=5 & 2 Hz);
5.55 (1H, broad);
7.34 (2H, doublet, J=8 Hz);
7.41 (2H, doublet, J=8 Hz).

Infrared Absorption Spectrum (KBr), $\nu_{max}$ cm$^{-1}$: 3302, 2968, 1667, 1653, 1641, 1529, 1382, 1319, 1264, 835, 560.

EXAMPLE 125

N-(4,4'-Dimethoxydiphenylmethyl)-3-oxo-4-azaandrost-5-ene-17β-carboxamide

The title compound was prepared in a yield of 50% in a similar manner to that described in Example 1 by reacting 3-oxo-4-azaandrost-5-ene-17β-carboxylic acid and 4,4'-dimethoxybenzhydrylamine.

Nuclear Magnetic Resonance Spectrum (CDCl$_3$), δ ppm:
0.70 (3H, singlet);
1.09 (3H, singlet);
1.10-2.30 (20H, multiplet);
2.45-2.50 (2H, multiplet);
3.79 (3H, singlet);
4.77-4.79 (1H, multiplet);
5.81 (1H, doublet, J=8 Hz);
6.18 (1H, doublet, J=8 Hz);
6.82-6.88 (4H, multiplet);
7.11-7.18 (4H, multiplet).

Infrared Absorption Spectrum (KBr), $\nu_{max}$ cm$^{-1}$: 1662, 1609, 1511, 1488, 1248, 1176, 1035, 831.

EXAMPLE 126

N-(4-Methoxydiphenylmethyl)-4-methyl-3-oxo-4-aza-5α-androst-1-ene-17β-carboxamide The title compound was prepared in a yield of 51% in a similar manner to that described in Example 1 by reacting 4-methyl-3-oxo-4-aza-5α-androst-1-ene-17β-carboxylic acid (prepared as described in Preparation 4) and 4-methoxybenzhydrylamine.

Nuclear Magnetic Resonance Spectrum (CDCl$_3$), δ ppm:
0.68 (3H, singlet);
0.91 (3H, singlet);
0.90-1.88 (12H, multiplet);
1.90-2.10 (2H, multiplet);
2.17-2.30 (2H, multiplet);
2.95 (3H, singlet);
3.34 (1H, doublet of doublets, J=13 & 3 Hz);
3.79 (3H, singlet);
5.83-5.87 (1H, multiplet);
5.85 (1H, doublet, J=10 Hz);
6.23 (2H, doublet, J=8 Hz);
6.66 (1H, doublet, J=10 Hz);
6.83-6.87 (2H, multiplet);
7.12-7.16 (2H, multiplet);
7.20-7.36 (5H, multiplet).

Infrared Absorption Spectrum (KBr), $\nu_{max}$ cm$^{-1}$: 3312, 2939, 1663, 1604, 1511, 1248, 820, 699.

EXAMPLE 127

N-(4,4'-Dimentoxydiphenylmethyl)-3-oxo-4-aza-5α-androstane-17β-carboxamide

The title compound was prepared in a yield of 51% in a similar manner to that described in Example 1 by reacting 3-oxo-4-aza-5α-androstane-17β-carboxylic acid and 4,4'-dimethoxybenzhydrylamine.

Nuclear Magnetic Resonance Spectrum (CDCl$_3$), δ ppm:
0.67 (3H, singlet);
0.89 (3H, singlet);
0.70-2.35 (18H, multiplet);
2.37-2.43 (2H, multiplet);
3.04 (1H, doublet of doublets, J=11 & 4 Hz);
3.78 (3H, singlet);
3.79 (3H, singlet);
5.54 (1H, broad);
5.79 (1H, doublet, J=8 Hz);
6.17 (1H, doublet, J=8 Hz);
6.82-6.88 (4H, multiplet);
7.10-7.16 (4H, multiplet).

Infrared Absorption Spectrum (KBr), $\nu_{max}$ cm$^{-1}$: 3305, 2936, 1659, 1511, 1247, 1175, 1034, 830.

PREPARATION 1

Methyl 4-methyl-3-oxo-4-aza-5α-androstane-17β-carboxylate

A suspension of 5.18 g of methyl 3-oxo-4-aza-5α-androstane-17β-carboxylate in 74 ml of dry dimethylformamide was added dropwise to a suspension of 0.82 g of sodium hydride (as a 55% w/w dispersion in mineral oil) in 30 ml of dry dimethylformamide at room temperature, and the suspension was stirred at 70° C. for 1 hour. At the end of this time, 22.1 g of methyl iodide were added dropwise to the mixture at room temperature, and the mixture was stirred at room temperature for 100 minutes and then at 70° C. for a further 1 hour. The reaction mixture was then diluted with diethyl ether, washed with water (twice) and with a saturated aqueous solution of sodium chloride, and dried over anhydrous sodium sulfate; the solvent was then removed by distillation under reduced pressure. The resulting residue was purified by column chromatography through 290 g of silica gel. Gradient elution with mixtures of acetone and methylene chloride ranging from 1:5 to 1:2 by volume afforded 2.95 g of the title compound.

Nuclear Magnetic Resonance Spectrum (CDCl$_3$), δ ppm:
- 0.66 (3H, singlet);
- 0.88 (3H, singlet);
- 0.77–2.60 (20H, multiplet);
- 2.92 (3H, singlet);
- 3.03 (1H, doublet of doublets, J=12 & 3 Hz);
- 3.67 (3H, singlet).

Infrared Absorption Spectrum (KBr), ν$_{max}$ cm$^{-1}$: 2932, 1732, 1649, 1209.

PREPARATION 2

4-Methyl-3-oxo-4-aza-5α-androstane-17β-carboxylic acid 1.68 g of potassium hydroxide (purity 85 w/w %) and 3.0 ml of water were added to a solution of 2.94 g of methyl 4-methyl-3-oxo-4-aza-5α-androstane-17β-carboxylate (prepared as described in Preparation 1) in 12.1 ml of methanol, and the mixture was stirred under reflux for 3 hours. At the end of this time, the reaction mixture was condensed by evaporation under reduced pressure. The resulting residue was acidified by adding aqueous hydrochloric acid. The crystals which precipitated were collected by filtration, washed with water and dried under air to afford 2.20 g of the title compound.

Nuclear Magnetic Resonance Spectrum (CDCl$_3$+CD$_3$OD), δ ppm:
- 0.72 (3H, singlet);
- 0.88 (3H, singlet);
- 0.75–2.60 (21H, multiplet);
- 2.93 (3H, singlet);
- 3.07 (1H, doublet of doublets, J=12 & 3 Hz).

Infrared Absorption Spectrum (KBr), ν$_{max}$ cm$^{-1}$: 2938, 1716, 1604, 1212, 1191, 723.

PREPARATION 3

Methyl 4-methyl-3-oxo-4-aza-5α-androst-1-ene-17β-carboxylate

A solution of 2.99 g of methyl 3-oxo-4-aza-5α-androst-1-ene-17β-carboxylate in 110 ml of dry dimethylacetamide was added dropwise to a suspension of 0.79 g of sodium hydride (as a 55% w/w dispersion in mineral oil) in 10 of dry dimethylacetamide, whilst ice-cooling, and the suspension was stirred at 70° C. for 30 minutes. At the end of this time, 13.0 g of methyl iodide were added dropwise to the suspension at room temperature, and the mixture was stirred at room temperature for 2.5 hours. The reaction mixture was then diluted with diethyl ether, washed with water (three times) and with a saturated aqueous solution of sodium chloride, and dried over anhydrous sodium sulfate; the solvent was then removed by distillation under reduced pressure. The resulting residue was purified by column chromatography through 160 g of silica gel. Gradient elution with mixtures of acetone and methylene chloride ranging from 1:20 to 1:2 by volume afforded 2.15 g of the title compound.

Nuclear Magnetic Resonance Spectrum (CDCl$_3$), δ ppm:
- 0.68 (3H, singlet);
- 0.92 (3H, singlet);
- 0.88–2.20 (15H, multiplet);
- 2.36 (1H, triplet, J=9 Hz);
- 2.96 (3H, singlet);
- 3.36 (1H, doublet of doublets, J=13 & 4 Hz);
- 3.67 (3H, singlet);
- 5.91 (1H, doublet, J=10 Hz);
- 6.71 (1H, doublet, J=10 Hz).

Infrared Absorption Spectrum (KBr), ν$_{max}$ cm$^{-1}$: 2944, 1729, 1660, 1606, 1432, 1218, 1199, 1174, 1154, 822.

PREPARATION 4

4-Methyl-3-oxo-4-aza-5α-androst-1-ene-17β-carboxylic acid 1.22 g of potassium hydroxide (purity 85 w/w %) and 2.2 ml of water were added to a solution of 2.15 g of methyl 4-methyl-3-oxo-4-aza-5α-androst-1-ene-17β-carboxylate (prepared as described in Preparation 3) in 8.8 ml of dioxane, and the mixture was stirred under reflux for 3 hours. At the end of this time, the reaction mixture was condensed by evaporation under reduced pressure. The resulting residue was acidified by adding aqueous hydrochloric acid. The crystals which precipitated were collected by filtration, washed with water and dried under air to afford 2.15 g of the title compound.

Nuclear Magnetic Resonance Spectrum (CDCl$_3$), δ ppm:
- 0.73 (3H, singlet);
- 0.92 (3H, singlet);
- 0.80–2.20 (16H, multiplet);
- 2.37 (1H, triplet, J=9 Hz);
- 2.96 (3H, singlet);
- 3.37 (1H, doublet of doublets, J=13 & 3 Hz);
- 5.88 (1H, doublet, J=10 Hz);
- 6.74 (1H, doublet, J=10 Hz).

Infrared Absorption Spectrum (KBr), ν$_{max}$ cm$^{-1}$: 2939, 1713, 1655, 1589, 1451, 1220, 1213, 1199, 823.

PREPARATION 5

4-Methyl-3-oxo-4-azaandrost-5-ene-17β-carboxylic acid 37 ml of a 40% v/v solution of methylamine in methanol were added to a solution of 26.0 g of 17β-carboxy-5-oxo-A-nor-3,5-secoandrostane-3-carboxylic acid in 150 ml of ethylene glycol at room temperature, and the mixture was stirred at the same temperature for 30 minutes. The reaction mixture was then gradually heated to 180° C., whilst stirring, and was stirred at 180° C. for a further 30 minutes. At the end of this time, the reaction mixture was cooled to room temperature and 200 ml of water were added to it. The crystals which precipitated were collected by filtration, washed with water and dried under air to afford 22.0 g of the title compound.

Nuclear Magnetic Resonance Spectrum (CDCl$_3$), δ ppm:
- 0.77 (3H, singlet);
- 1.05 (3H, singlet);
- 1.00–2.70 (18H, multiplet);
- 3.13 (3H, singlet);
- 5.03–5.06 (1H, multiplet).

Infrared Absorption Spectrum (KBr), ν$_{max}$ cm$^{-1}$: 3459, 2943, 1726, 1616, 1474, 1393, 1329, 1230, 1168, 1057.

TEST EXAMPLE

(1) Preparation of 5α-reductase from Rat Prostate Glands

The prostatic lobes of a mature male rat (body weight 350–450 g, Sprague-Dawley strain) were cut into small pieces with scissors. About three parts by weight of a buffer solution [20 mM potassium phosphate buffer solution (ph 7.4) containing 0.33M sucrose, 1 mM dithiothreitol, 50 μM nicotinamide adenine dinucleotide phosphate-reduced form (NADPH) and 0.001% PMSF (phenylmethyl sulfonyl fluoride)] were added to one part by weight of the tissue pieces, and the mixture was homogenized first by means of a Polytron (trade mark, KINEMATICA GmbH) homogenizer, and then by means of a Teflon (trade mark) glass homogenizer. The prostatic tissue suspension thus homogenized was then centrifuged (140000×g, 60 minutes) to separate the precipitate.

About three parts by weight of the buffer solution described above were added to one part of the precipitate to suspend it, and the suspension was centrifuged again (140000×g, 60 minutes) to wash it and separate a precipitate, which was regarded as a rat 5α-reductase preparation. Sufficient of the buffer solution described above was added to this precipitate for the protein content of the solution to become between 20 and 40 mg/ml. The solution was frozen and stored at −80° C. The protein content was determined by a Bio-Rad protein assay in which bovine γ-globulin (Cohn Fraction II, Sigma) was used as the protein standard.

(2) Assay of Rat 5α-reductase Inhibition

5 μl of a dimethyl sulfoxide or ethanol solution in which a test compound to be tested was dissolved were added to 0.5 ml of a 40 mM potassium phosphate buffer solution (pH 6.5) containing rat 5α-reductase (protein content, 1 mg), 1 μM [$^{14}$C] testosterone, 1 mM dithiothreitol and 500 μM NADPH (final concentration $10^{-8}$M of the test compound), and incubated for 15 to 30 minutes at 37° C. As a control, only the solvent was added to one sample. 2 ml of ethyl acetate containing 10 μg each of testosterone, 5α-dihydrotestosterone and androstenedione were then added to stop the reaction. The mixture was centrifuged (1400×g, 5 minutes). The ethyl acetate layer was separated and transferred to another test tube, where it was evaporated to dryness whilst spraying it with nitrogen gas. The steroids were dissolved in 40 μl of ethyl acetate. The solution was spotted on a thin layer chromatographic plate (LK5DF silica plate, Whatman), and developed with a mixture of ethyl acetate with cyclohexane (1:1 by volume) twice at room temperature. The steroid fraction was identified by color development by ultraviolet radiation or by heating with a 1% cesium sulfate/10% sulfuric acid solution. The radioactivity on the thin layer chromatographic plate was measured by means of a bio-image analyzer (Fuji Film Co. Ltd.). The enzyme activity was given by the amount [conversion rate (%)] of [$^{14}$C] 5α-dihydro-testosterone which was converted from the [$^{14}$C] testosterone initially added. The rat 5α-reductase inhibiting activity of a test sample was calculated from the following equation:

$$\text{Rat 5α-reductase inhibiting activity} = \frac{\text{conversion rate of the sample group}}{\text{conversion rate of the control group}} \times 100\ (\%)$$

The results are shown in the following table.

TABLE 4

| Rat 5α-reductase inhibiting activity | |
|---|---|
| Test compound | Inhibiting activity (%) ($10^{-8}$ M) |
| Example No. 1 | 89.2 |
| Example No. 3 | 89.1 |
| Example No. 4 | 74.1 |
| Example No. 8 | 74.6 |
| Example No. 12 | 78.4 |
| Example No. 20 | 86.7 |
| Example No. 26 | 87.3 |
| Example No. 37 | 82.2 |
| Example No. 40 | 88.6 |
| Example No. 42 | 72.3 |
| Example No. 44 | 73.2 |
| Example No. 62 | 90.1 |
| Example No. 65 | 80.0 |
| Example No. 73 | 80.5 |
| Compound A2 | 30.0 |

We claim:

1. A compound of formula (I):

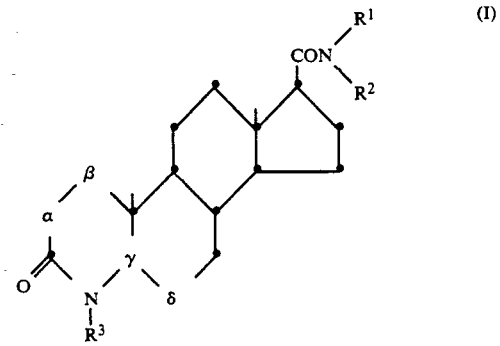

in which:

R$^1$ represents a hydrogen atom, an unsubstituted alkyl group having from 1 to 6 carbon atoms or a substituted alkyl group having from 1 to 6 carbon atoms which is substituted by at least one substituent selected from the group consisting of aryl groups as defined below, aromatic heterocyclic groups as defined below, carboxy groups and hydroxy groups;

R$^2$ represents a substituted alkyl group having from 1 to 6 carbon atoms which is (i) substituted by at least one substituent selected from the group consisting of aryl groups as defined below and aromatic heterocyclic groups as defined below, and (ii) which alkyl group is not further substituted or is additionally substituted by at least one substituent selected from the group consisting of carboxy groups and hydroxy groups, or a diarylamino group;

R$^3$ represents a hydrogen atom, an unsubstituted alkyl group having from 1 to 6 carbon atoms, a substituted alkyl group having from 1 to 6 to carbon atoms which is substituted by at least one substituent selected from the group consisting of aryl groups as defined below, carboxy groups and hydroxy groups, or an alkenyl group having from 3 to 6 carbon atoms; each of the bonds represented by α-β and γ-δ is a carbon-carbon single bond or a carbon-carbon double bond;

said aryl groups are carbocyclic aryl groups which have from 6 to 10 ring carbon atoms and which are unsubstituted or are substituted by at least one substituent selected from the group consisting of alkyl groups having from 1 to 6 carbon atoms, alkoxy groups having from 1 to 6 carbon atoms, alkoxycarbonyl groups having from 2 to 7 carbon atoms, hydroxy groups, halogen atoms and groups of formula —NHR$^a$, where R$^a$ represents an alkanoyl group having from 1 to 5 carbon atoms;

said aromatic heterocyclic groups have 5 or 6 ring atoms of which from 1 to 3 are hetero-atoms selected from the group consisting of nitrogen, oxygen and sulfur hetero-atoms and are unsubstituted or are substituted by at least one substituent selected from the group consisting of alkyl groups having from 1 to 6 carbon atoms, alkoxy groups having from 1 to 6 carbon atoms and halogen atoms;

and pharmaceutically acceptable salts and esters thereof.

2. The compound of claim 1, wherein $R^1$ represents a hydrogen atom, an alkyl group having 3 carbon atoms, a benzyl group, a substituted benzyl group having at least one substituent selected from the group consisting of substituents (a), defined below, a furylmethyl group or a thienylmethyl group; and said substituents (a) are selected from the group consisting of alkyl groups having from 1 to 4 carbon atoms, alkoxy groups having from 1 to 4 carbon atoms, halogen atoms, hydroxy groups, alkoxycarbonyl groups having from 2 to 5 carbon atoms and aliphatic carboxylic acylamino groups having from 1 to 5 carbon atoms.

3. The compound of claim 1, wherein $R^2$ represents a substituted alkyl group having from 1 to 4 carbon atoms and substituted by at least one substituent selected from the group consisting of phenyl groups, substituted phenyl groups having at least one substituent selected from the group consisting of substituents (a), defined below, furyl groups, furyl groups substituted by a $C_1$-$C_4$ alkyl substituent, thienyl groups and thienyl groups substituted by a $C_1$-$C_4$ alkyl substituent, said alkyl groups having no further substituents or being substituted by at least one substituent selected from the group consisting of carboxy groups and hydroxy groups; and said substituents (a) are selected from the group consisting of alkyl groups having from 1 to 4 carbon atoms, alkoxy groups having from 1 to 4 carbon atoms, halogen atoms, hydroxy groups, alkoxycarbonyl groups having from 2 to 5 carbon atoms and aliphatic carboxylic acylamino groups having from 1 to 5 carbon atoms.

4. The compound of claim 1, wherein $R^2$ represents a diphenylamino group in which each phenyl group is unsubstituted or one or both of them are substituted by at least one substituent selected from the group consisting of substituents (a), defined below; and said substituents (a) are selected from the group consisting of alkyl groups having from 1 to 4 carbon atoms, alkoxy groups having from 1 to 4 carbon atoms, halogen atoms, hydroxy groups, alkoxycarbonyl groups having from 2 to 5 carbon atoms and aliphatic carboxylic acylamino groups having from 1 to 5 carbon atoms.

5. The compound of claim 1, wherein $R^3$ represents a hydrogen atoms, an alkyl group having from 1 to 4 carbon atoms, a substituted alkyl group having from 1 to 4 carbon atoms and substituted by at least one substituent selected from the group consisting of phenyl groups, substituted phenyl groups having at least one substituent selected from the group consisting of substituents (a), defined below, carboxy groups and hydroxy groups or an alkenyl group having 3 or 4 carbon atoms; and said substituents (a) are selected from the group consisting of alkyl groups having from 1 to 4 carbon atoms, alkoxy groups having from 1 to 4 carbon atoms, halogen atoms, hydroxy groups, alkoxycarbonyl groups having from 2 to 5 carbon atoms and aliphatic carboxylic acylamino groups having from 1 to 5 carbon atoms.

6. The compound of claim 1, wherein the bond represented by α-β is a carbon-carbon single bond and the bond represented by γ-δ is a carbon-carbon single bond or a carbon-carbon double bond, or the bond represented by α-β is a carbon-carbon double bond and the bond represented by γ-δ is a carbon-carbon single bond.

7. The compound of claim 1, wherein:

$R^1$ represents a hydrogen atom, an alkyl group having 3 carbon atoms, a benzyl group, a substituted benzyl group having at least one substituent selected from the group consisting of substituents (a), defined below, a furylmethyl group or a thienylmethyl group;

$R^2$ represents a substituted alkyl group having from 1 to 4 carbon atoms and substituted by at least one substituent selected from the group consisting of phenyl groups, substituted phenyl groups having at least one substituent selected from the group consisting of substituents (a), defined below, furyl groups, furyl groups substituted by a $C_1$-$C_4$ alkyl substituent, thienyl groups and thienyl groups substituted by a $C_1$-$C_4$ alkyl substituent, said alkyl groups having no further substituents or being substituted by at least one substituent selected from the group consisting of carboxy groups and hydroxy groups; or $R^2$ represents a diphenylamino group in which each phenyl group is unsubstituted or one or both of them are substituted by at least one substituent selected from the group consisting of substituents (a), defined below;

$R^3$ represents a hydrogen atom, an alkyl group having from 1 to 4 carbon atoms, a substituted alkyl group having from 1 to 4 carbon atoms and substituted by at least one substituent selected from the group consisting of phenyl groups, substituted phenyl groups having at least one substituent selected from the group consisting of substituents (a), defined below, carboxy groups and hydroxy groups or an alkenyl group having 3 or 4 carbon atoms;

said substituents (a) are selected from the group consisting of alkyl groups having from 1 to 4 carbon atoms, alkoxy groups having from 1 to 4 carbon atoms, halogen atoms, hydroxy groups, alkoxycarbonyl groups having from 2 to 5 carbon atoms and aliphatic carboxylic acylamino groups having from 1 to 5 carbon atoms; and the bond represented by α-β is a carbon-carbon single bond and the bond represented by γ-δ is a carbon-carbon single bond or a carbon-carbon double bond, or the bond represented by α-β is a carbon-carbon double bond and the bond represented by γ-δ is a carbon-carbon single bond.

8. The compound of claim 1, wherein $R^1$ represents a hydrogen atom, an isopropyl group, a benzyl group, a substituted benzyl group having at least one substituent selected from the group consisting of substituents (b), defined below or a thienylmethyl group; and said substituents (b) are selected from the group consisting of methyl groups, ethyl groups, methoxy groups, ethoxy groups, fluorine atoms, chlorine atoms, bromine atoms, hydroxy groups, ethoxycarbonyl groups, methoxycarbonyl groups, formamido groups and acetamido groups.

9. The compound of claim 1, wherein $R^2$ represents a substituted alkyl group having from 1 to 4 carbon atoms and substituted by at least one substituent selected from the group consisting of phenyl groups, substituted phenyl groups having at least one substituent selected from the group consisting of substituents (b), defined below, furyl groups, substituted furyl groups having a methyl substituent, thienyl groups and substituted thienyl groups having a methyl substituent, said alkyl groups having no further substituents or being substituted by at least one hydroxy substituent or a diphenylamino group in which each phenyl group is unsubstituted or one or both of them are substituted by at least one substituent selected from the group consisting of substituents (b), defined below; and said substituents (b) are selected from the group consisting of methyl groups, ethyl groups, methoxy groups, ethoxy groups, fluorine atoms, chlorine atoms, bromine atoms, hydroxy groups, ethoxycarbonyl groups, methoxycarbonyl groups, formamido groups and acetamido groups.

10. The compound of claim 1, wherein $R^3$ represents a hydrogen atom, a methyl group, an ethyl group, a benzyl group, a substituted benzyl group which is substituted by at least one substituent selected from the group consisting of substituents (b), defined below, a substituted alkyl group having from 1 to 3 carbon atoms and substituted by at least one hydroxy substituent or an allyl group; and said substituents (b) are selected from the group consisting of methyl groups, ethyl groups, methoxy groups, ethoxy groups, fluorine atoms, chlorine atoms, bromine atoms, hydroxy groups, ethoxycarbonyl groups, methoxycarbonyl groups, formamido groups and acetamido groups.

11. The compound of claim 1, wherein:

$R^1$ represents a hydrogen atom, an isopropyl group, a benzyl group, a substituted benzyl group having at least one substituent selected from the group consisting of substituents (b), defined below or a thienylmethyl group;

$R^2$ represents a substituted alkyl group having from 1 to 4 carbon atoms and substituted by at least one substituent selected from the group consisting of phenyl groups, substituted phenyl groups having at least one substituent selected from the group consisting of substituents (b), defined below, furyl groups, substituted furyl groups having a methyl substituent, thienyl groups and substituted thienyl groups having a methyl substituent, said alkyl groups having no further substituents or being substituted by at least one hydroxy substituent or a diphenylamino group in which each phenyl group is unsubstituted or one or both of them are substituted by at least one substituent selected from the group consisting of substituents (b), defined below;

$R^3$ represents a hydrogen atom, a methyl group, an ethyl group, a benzyl group, a substituted benzyl group which is substituted by at least one substituent selected from the group consisting of substituents (b), defined below, a substituted alkyl group having from 1 to 3 carbon atoms and substituted by at least one hydroxy substituent or an allyl group;

said substituents (b) are selected from the group consisting of methyl groups, ethyl groups, methoxy groups, ethoxy groups, fluorine atoms, chlorine atoms, bromine atoms, hydroxy groups, ethoxycarbonyl groups, methoxycarbonyl groups, formamido groups and acetamido groups; and the bond represented by α-β is a carbon-carbon single bond and the bond represented by γ-δ is a carbon-carbon single bond or a carbon-carbon double bond, or the bond represented by α-β is a carbon-carbon double bond and the bond represented by γ-δ is a carbon-carbon single bond.

12. The compound of claim 1, wherein $R^1$ and $R^2$ are the same or different and each represents a benzyl group or a substituted benzyl group having at least one substituent selected from the group consisting of substituents (c), defined below;

said substituents (c) are selected from the group consisting of methyl groups, methoxy groups, fluorine atoms, chlorine atoms, hydroxy groups, and acetamido groups.

13. The compound of claim 1, wherein $R^1$ represents a hydrogen atom and $R^2$ represents a substituted alkyl group having from 1 to 3 carbon atoms and substituted by at least one substituent selected from the group consisting of phenyl groups, substituted phenyl groups having at least one substituent selected from the group consisting of substituents (c), defined below, and thienyl groups or a diphenylamino group in which each phenyl group is unsubstituted or one or both of them are substituted by at least one substituent selected from the group consisting of substituents (c), defined below;

said substituents (c) are selected from the group consisting of methyl groups, methoxy groups, fluorine atoms, chlorine atoms, hydroxy groups, and acetamido groups.

14. The compound of claim 1, wherein $R^3$ represents a hydrogen atom, a methyl group or an ethyl group.

15. The compound of claim 1, wherein:

$R^1$ and $R^2$ are the same or different and each represents a benzyl group or a substituted benzyl group having at least one substituent selected from the group consisting of substituents (c), defined below;

said substituents (c) are selected from the group consisting of methyl groups, methoxy groups, fluorine atoms, chlorine atoms, hydroxy groups, and acetamido groups; and $R^3$ represents a hydrogen atom, a methyl group or an ethyl group.

16. The compound of claim 1, wherein:

$R^1$ represents a hydrogen atom;

$R^2$ represents a substituted alkyl group having from 1 to 3 carbon atoms and substituted by at least one substituent selected from the group consisting of phenyl groups, substituted phenyl groups having at least one substituent selected from the group consisting of substituents (c), defined below, furyl groups and thienyl groups a diphenylamino group in which each phenyl group is unsubstituted or one or both of them are substituted by at least one substituent selected from the group consisting of substituents (c), defined below;

said substituents (c) are selected from the group consisting of methyl groups, methoxy groups, fluorine atoms, chlorine atoms, hydroxy groups, and acetamido groups; and $R^3$ represents a hydrogen atom, a methyl group or an ethyl group; and the bond represented by $\alpha$-$\beta$ is a carbon-carbon single bond and the bond represented by $\gamma$-$\delta$ is a carbon-carbon single bond or a carbon-carbon double bond, or the bond represented by $\alpha$-$\beta$ is a carbon-carbon double bond and the bond represented by $\gamma$-$\delta$ is a carbon-carbon single bond.

17. The compound of claim 1, wherein $R^1$ represents a hydrogen atom, an unsubstituted alkyl group having from 1 to 6 carbon atoms or a substituted alkyl group having from 1 to 6 carbon atoms which is substituted by at least one substituent selected from the group consisting of aryl groups as defined below, aromatic heterocyclic groups as defined below and carboxy groups;

said aryl groups are carbocyclic aryl groups which have from 6 to 10 ring carbon atoms and which are unsubstituted or are substituted by at least one substituent selected from the group consisting of alkyl groups having from 1 to 4 carbon atoms, alkoxy groups having from 1 to 4 carbon atoms, hydroxy groups and halogen atoms;

said aromatic heterocyclic groups have 5 or 6 ring atoms of which from one to three is a hetero-atom selected from the group consisting of nitrogen, oxygen and sulfur hetero-atoms and are unsubstituted or are substituted by at least one substituent selected from the group consisting of alkyl groups having from 1 to 4 carbon atoms, alkoxy groups having from 1 to 4 carbon atoms and halogen atoms.

18. The compound of claim 1, wherein $R^2$ represents a substituted alkyl group having from 1 to 6 carbon atoms which is substituted by at least one substituent selected from the group consisting of aryl groups as defined below and aromatic heterocyclic groups as defined below, said aryl groups are carbocyclic aryl groups which have from 6 to 10 ring carbon atoms and which are unsubstituted or are substituted by at least one substituent selected from the group consisting of alkyl groups having from 1 to 4 carbon atoms, alkoxy groups having from 1 to 4 carbon atoms, hydroxy groups and halogen atoms;

said aromatic heterocyclic groups have 5 or 6 ring atoms of which from one is to three a hetero-atom selected from the group consisting of nitrogen, oxygen and sulfur hetero-atoms and are unsubstituted or are substituted by at least one substituent selected from the group consisting of alkyl groups having from 1 to 4 carbon atoms, alkoxy groups having from 1 to 4 carbon atoms and halogen atoms.

19. The compound of claim 1, wherein $R^3$ represents a hydrogen atom, an unsubstituted alkyl group having from 1 to 6 carbon atoms, a substituted alkyl group having from 1 to 6 carbon atoms which is substituted by at least one substituent selected from the group consisting of aryl groups as defined below, carboxy groups and hydroxy groups, said aryl groups are carbocyclic aryl groups which have from 6 to 10 ring carbon atoms and which are unsubstituted or are substituted by at least one substituent selected from the group consisting of alkyl groups having from 1 to 4 carbon atoms, alkoxy groups having from 1 to 4 carbon atoms, hydroxy groups and halogen atoms.

20. A method of treating prostatic hypertrophy, which comprises administering to an animal at least one active compound, wherein the active compound is at least one compound of formula (I) or a pharmaceutically acceptable salt or ester thereof, as claimed in claim 1.

21. The compound of claim 1, wherein:

$R^1$ represents a hydrogen atom, an unsubstituted alkyl group having from 1 to 6 carbon atoms or a substituted alkyl group having from 1 to 6 carbon atoms which is substituted by at least one substituent selected from the group consisting of aryl groups as defined below, aromatic heterocyclic groups as defined below and carboxy groups;

$R^2$ represents a substituted alkyl group having from 1 to 6 carbon atoms which is substituted by at least one substituent selected from the group consisting of aryl groups as defined below and aromatic heterocyclic groups as defined below, $R^3$ represents a hydrogen atom, an unsubstituted alkyl group having from 1 to 6 carbon atoms, a substituted alkyl group having from 1 to 6 carbon atoms which is substituted by at least one substituent selected from the group consisting of aryl groups as defined below, carboxy groups and hydroxy groups, said aryl groups are carbocyclic aryl groups which have from 6 to 10 ring carbon atoms and which are unsubstituted or are substituted by at least one substituent selected from the group consisting of alkyl groups having from 1 to 4 carbon atoms, alkoxy groups having from 1 to 4 carbon atoms, hydroxy groups and halogen atoms;

said aromatic heterocyclic groups have 5 or 6 ring atoms of which from one to three is a hetero-atom selected from the group consisting of nitrogen, oxygen and sulfur hetero-atoms and are unsubstituted or are substituted by at least one substituent selected from the group consisting of alkyl groups having from 1 to 4 carbon atoms, alkoxy groups having from 1 to 4 carbon atoms and halogen atoms.

22. The compound of claim 1, wherein $R^1$ represents a hydrogen atom, an unsubstituted alkyl group having from 1 to 4 carbon atoms or a substituted alkyl group having from 1 to 4 carbon atoms which is substituted by one substituent selected from the group consisting of phenyl groups, substituted phenyl groups having at least one substituent selected from the group consisting of $C_1$-$C_4$ alkyl, $C_1$-$C_4$ alkoxy, halogen and hydroxy substituents, a furyl group and a thienyl group.

23. The compound of claim 1, wherein $R^2$ represents a substituted alkyl group having from 1 to 4 carbon atoms and substituted by from 1 to 3 substituents selected from the group consisting of phenyl groups, substituted phenyl groups having at least one substituent selected from the group consisting of alkyl groups having from 1 to 4 carbon atoms, alkoxy groups having from 1 to 4 carbon atoms, halogen atoms and hydroxy groups, a furyl group or a thienyl group.

24. The compound of claim 1, wherein $R^3$ represents a hydrogen atom, an alkyl group having from 1 to 4 carbon atoms, a substituted alkyl group having from 1 to 4 carbon atoms and having at least one substituents selected from the group consisting of phenyl groups, carboxy groups and hydroxy groups, or an alkenyl group having 3 or 4 carbon atoms.

25. The compound of claim 1, wherein the bond represented by $\alpha$-$\beta$ is a carbon-carbon single bond and the bond represented by $\gamma$-$\delta$ is a carbon-carbon single bond or a carbon-carbon double bond.

26. The compound of claim 1, wherein the bond represented by $\alpha$-$\beta$ is a carbon-carbon double bond and the bond represented by $\gamma$-$\delta$ is a carbon-carbon single bond.

27. The compound of claim 1, wherein:
$R^1$ represents a hydrogen atom, an unsubstituted alkyl group having from 1 to 4 carbon atoms or a substituted alkyl group having from 1 to 4 carbon atoms which is substituted by one substituent selected from the group consisting of phenyl groups, substituted phenyl groups having at least one substituent selected from the group consisting of $C_1$-$C_4$ alkyl, $C_1$-$C_4$ alkoxy, halogen and hydroxy substituents, a furyl group and a thienyl group;
$R^2$ represents a substituted alkyl group having from 1 to 4 carbon atoms and substituted by from 1 to 3 substituents selected from the group consisting of phenyl groups, substituted phenyl groups having at least one substituent selected from the group consisting of alkyl groups having from 1 to 4 carbon atoms, alkoxy groups having from 1 to 4 carbon atoms, halogen atoms and hydroxy groups, a furyl group or a thienyl group;
$R^3$ represents a hydrogen atom, an alkyl group having from 1 to 4 carbon atoms, a substituted alkyl group having from 1 to 4 carbon atoms and having at least one substituents selected from the group consisting of phenyl groups, carboxy groups and hydroxy groups, or an alkenyl group having 3 or 4 carbon atoms; and
the bond represented by $\alpha$-$\beta$ is a carbon-carbon single bond and the bond represented by $\gamma$-$\delta$ is a carbon-carbon single bond or a carbon-carbon double bond; or
the bond represented by $\alpha$-$\beta$ is a carbon-carbon double bond and the bond represented by $\gamma$-$\delta$ is a carbon-carbon single bond.

28. The compound of claim 1, wherein $R^1$ represents a hydrogen atom and and $R^2$ represents a group of formula:

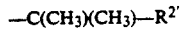
—C(CH₃)(CH₃)—R²' in which $R^{2'}$ represents a phenyl group, a substituted phenyl group having at least one substituent selected from the group consisting of methyl, methoxy, chloro, fluoro and hydroxy substituents, or a substituted alkyl group having from 1 to 3 carbon atoms and having 2 or 3 substituents selected from the group consisting of phenyl groups, substituted phenyl groups having at least one substituent selected from the group consisting of methyl, methoxy, fluoro, chloro and hydroxy substituents, furyl groups and thienyl groups.

29. The compound of claim 1, wherein $R^1$ and $R^2$ are same or different and each represents a substituted alkyl group having from 1 to 3 carbon atoms and having one substituent selected from the group consisting of phenyl groups, substituted phenyl groups having at least one substituent selected from the group consisting of methyl, methoxy, fluoro, chloro and hydroxy substituents, furyl groups and thienyl groups.

30. The compound of claim 1, wherein $R^3$ represents a hydrogen atom, a methyl group, an ethyl group, an allyl group or a benzyl group.

31. The compound of claim 1, wherein the bond represented by $\alpha$-$\beta$ is a carbon-carbon single bond or a carbon-carbon double bond and the bond represented by $\gamma$-$\delta$ is a carbon-carbon single bond.

32. The compound of claim 1, wherein:
$R^1$ represents a hydrogen atom and $R^2$ represents a group of formula:

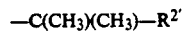
—C(CH₃)(CH₃)—R²' in which $R^{2'}$ represents a phenyl group, a substituted phenyl group having at least one substituent selected from the group consisting of methyl, methoxy, chloro, fluoro and hydroxy substituents, or a substituted alkyl group having from 1 to 3 carbon atoms and having 2 or 3 substituents selected from the group consisting of phenyl groups, substituted phenyl groups having at least one substituent selected from the group consisting of methyl, methoxy, fluoro, chloro and hydroxy substituents, furyl groups and thienyl groups;
$R^3$ represents a hydrogen atom, a methyl group, an ethyl group, an allyl group or a benzyl group; and
the bond represented by $\alpha$-$\beta$ is a carbon-carbon single bond or a carbon-carbon double bond and the bond represented by $\gamma$-$\delta$ is a carbon-carbon single bond.

33. The compound of claim 1, wherein:
$R^1$ and $R^2$ are same or different and each represents a substituted alkyl group having from 1 to 3 carbon atoms and having one substituent selected from the group consisting of phenyl groups, substituted phenyl groups having at least one substituent selected from the group consisting of methyl, methoxy, fluoro, chloro and hydroxy substituents, furyl groups and thienyl groups;
$R^3$ represents a hydrogen atom, a methyl group, an ethyl group, an allyl group or a benzyl group; and
the bond represented by $\alpha$-$\beta$ is a carbon-carbon single bond or a carbon-carbon double bond and the bond represented by $\gamma$-$\delta$ is a carbon-carbon single bond.

34. The compound of claim 1, wherein $R^1$ represents a hydrogen atom and $R^2$ represents a diphenylmethyl group, substituted diphenylmethyl group having at least one substituent selected from the group consisting of methyl, methoxy, fluoro, chloro or hydroxy substituents, a 1,2-diphenylethyl group, a substituted 1,2-diphenylethyl group having at least one substituent selected from the group consisting of methyl, methoxy, fluoro, chloro or hydroxy substituents, a 1,1-diphenylethyl group or a substituted 1,1-diphenylethyl group having at least one substituent selected from the group consisting of methyl, methoxy, fluoro, chloro or hydroxy substituents.

35. The compound of claim 1, wherein $R^3$ represents a hydrogen atom, a methyl group, or an ethyl group.

36. The compound of claim 1, wherein:
$R^1$ represents a hydrogen atom;
$R^2$ represents a diphenylmethyl group, substituted diphenylmethyl group having at least one substituent selected from the group consisting of methyl, methoxy, fluoro, chloro or hydroxy substituents, a 1,2-diphenylethyl group, a substituted 1,2- diphenylethyl group having at least one substituent selected from the group consisting of methyl, methoxy, fluoro, chloro or hydroxy substituents, a 1,1-diphenylethyl group or a substituted 1,1-diphenylethyl group having at least one substituent selected from the group consisting of methyl, methoxy, fluoro, chloro or hydroxy substituents;

$R^3$ represents a hydrogen atom, a methyl group, or an ethyl group; and the bond represented by $\alpha$-$\beta$ is a carbon-carbon single bond or a carbon-carbon double bond and the bond represented by $\gamma$-$\delta$ is a carbon-carbon single bond.

37. The compound of claim 1, which is N-(1,2-diphenylethyl)-3-oxo-4-aza-5α-androstane-17β-carboxamide.

38. The compound of claim 1, which is N-(diphenylmethyl)-3-oxo-4-aza-5α-androstane-17β-carboxamide.

39. The compound of claim 1, which is N-(1,1-diphenylethyl)-3-oxo-4-aza-5α-androstane-17β-carboxamide.

40. The compound of claim 1, which is N-(diphenylmethyl)-4-methyl-3-oxo-4-aza-5α-androstane-17β-carboxamide.

41. The compound of claim 1, which is N-(1,2-diphenylethyl)-4-methyl-3-oxo-4-aza-5α-androstane-17β-carboxamide.

42. The compound of claim 1, which is N-(1-methyl-1-phenylethyl)-3-oxo-4-aza-5α-androstane-17β-carboxamide.

43. The compound of claim 1, which is N-[1-methyl-1-(2-thienyl)ethyl]-3-oxo-4-aza-5α-androstane-17β-carboxamide.

44. The compound of claim 1, which is N-[1-methyl-1-(2-thienyl)ethyl]-4-methyl-3-oxo-4-aza-5α-androstane-17β-carboxamide.

45. The compound of claim 1, which is N-(1-methyl-1-phenylethyl)-4-methyl-3-oxo-4-aza-5α-androstane-17β-carboxamide.

46. The compound of claim 1, which is N-[2-(4-methylphenyl)-1-phenylethyl]-4-methyl-3-oxo-4-aza-5α-androstane-17β-carboxamide.

47. The compound of claim 1, which is N-[2-(4-methylphenyl)-1-phenylethyl]-3-oxo-4-aza-5α-androstane-17β-carboxamide.

48. The compound of claim 1, which is N-(1,1-diphenylethyl)-4-methyl-3-oxo-4-aza-5α-androstane-17β-carboxamide.

49. The compound of claim 1, which is N-[α-(4-hydroxyphenyl)benzyl]-3-oxo-4-aza-5α-androstane-17β-carboxamide.

50. The compound of claim 1, which is N-[α-(4-hydroxyphenyl)benzyl]-4-methyl-3-oxo-4-aza-5α-androstane-17β-carboxamide.

51. The compound of claim 1, which is N-[1-(4-methoxyphenyl)-1-methylethyl]-3-oxo-4-aza-5α-androstane-17β-carboxamide.

52. The compound of claim 1, which is N-[1-(4-methoxyphenyl)-1-methylethyl]-4-methyl-3-oxo-4-aza-5α-androstane-17β-carboxamide.

53. The compound of claim 1, which is N,N-diphenyl-3-oxo-4-aza-5α-androstane-17β-carbohydrazide.

54. The compound of claim 1, which is N,N-diphenyl-4-methyl-3-oxo-4-aza-5α-androstane-17β-carbohydrazide.

55. The compound of claim 1, which is N-[1-(3-methoxyphenyl)-1-methylethyl]-4-methyl-3-oxo-4-aza-5α-androstane-17β-carboxamide.

56. The compound of claim 1, which is N-(1,2-diphenylethyl)-3-oxo-4-aza-5α-androst-1-ene-17β-carboxamide.

57. The compound of claim 1, which is N-(1,2-diphenylethyl)-4-methyl-3-oxo-4-aza-5α-androst-1-ene-17β-carboxamide.

58. The compound of claim 1, which is N-(diphenylmethyl)-3-oxo-4-aza-5α-androst-1-ene-17β-carboxamide.

59. The compound of claim 1, which is N-(diphenylmethyl)-4-methyl-3-oxo-4-aza-5α-androst-1-ene-17β-carboxamide.

60. The compound of claim 1, which is N-[1-phenyl-2-(4-methylphenyl)ethyl]-3-oxo-4-aza-5α-androst-1-ene-17β-carboxamide.

61. The compound of claim 1, which is N-[1-phenyl-2-(4-methylphenyl)ethyl]-4-methyl-3-oxo-4-aza-5α-androst-1-ene-17β-carboxamide.

62. The compound of claim 1, which is N-(1,1-diphenylethyl)-3-oxo-4-aza-5α-androst-1-ene-17β-carboxamide.

63. The compound of claim 1, which is N-(1,1-diphenylethyl)-4-methyl-3-oxo-4-aza-5α-androst-1-ene-17β-carboxamide.

64. The compound of claim 1, which is N-(1-methyl-1-phenylethyl)-3-oxo-4-aza-5α-androst-1-ene-17β-carboxamide.

65. The compound of claim 1, which is N-(1-methyl-1-phenylethyl)-4-methyl-3-oxo-4-aza-5α-androst-1-ene-17β-carboxamide.

66. The compound of claim 1, which is N-[1-methyl-1-(2-thienyl)ethyl]-3-oxo-4-aza-5α-androst-1-ene-17β-carboxamide.

67. The compound of claim 1, which is N-[1-methyl-1-(2-thienyl)ethyl]-4-methyl-3-oxo-4-aza-5α-androst-1-ene-17β-carboxamide.

68. The compound of claim 1, which is N-[α-(4-hydroxyphenyl)benzyl]-3-oxo-4-aza-5α-androst-1-ene-17β-carboxamide.

69. The compound of claim 1, which is N-[α-(4-hydroxyphenyl)benzyl]-4-methyl-3-oxo-4-aza-5α-androst-1-ene-17β-carboxamide.

70. The compound of claim 1, which is N-[1-(4-methoxyphenyl)-1-methylethyl]-3-oxo-4-aza-5α-androst-1-ene-17β-carboxamide.

71. The compound of claim 1, which is N-[1-(4-methoxyphenyl)-1-methylethyl]-4-methyl-3-oxo-4-aza-5α-androst-1-ene-17β-carboxamide.

72. The compound of claim 1, which is N-(2-hydroxy-1,2-diphenylethyl)-3-oxo-4-aza-5α-androst-1-ene-17β-carboxamide.

73. The compound of claim 1, which is N,N-diphenyl-3-oxo-4-aza-5α-androst-1-ene-17β-carbohydrazide.

74. The compound of claim 1, which is N,N-diphenyl-4-methyl-3-oxo-4-aza-5α-androst-1-ene-17β-carbohydrazide.

75. The compound of claim 1, which is N-[1-(2-methoxyphenyl)-1-methylethyl]-3-oxo-4-aza-5α-androst-1-ene-17β-carboxamide.

76. The compound of claim 1, which is N-(1,2-diphenylethyl)-3-oxo-4-azaandrost-5-ene-17β-carboxamide.

77. The compound of claim 1, which is N-(1,2-diphenylethyl)-4-methyl-3-oxo-4-azaandrost-5-ene-17β-carboxamide.

78. The compound of claim 1, which is N-(diphenylmethyl)-3-oxo-4-azaandrost-5-ene-17β-carboxamide.

79. The compound of claim 1, which is N-(diphenylmethyl)-4-methyl-3-oxo-4-azaandrost-5-ene-17β-carboxamide.

80. The compound of claim 1, which is N-[2-(4-methylphenyl)-1-phenylethyl]-3-oxo-4-azaandrost-5-ene-17β-carboxamide.

81. The compound of claim 1, which is N-[2-(4-methylphenyl)-1-phenylethyl]-4-methyl-3-oxo-4-azaandrost-5-ene-17β-carboxamide.

82. The compound of claim 1, which is N-(1,1-diphenylethyl)-3-oxo-4-azaandrost-5-ene-17β-carboxamide.

83. The compound of claim 1, which is N-(1,1-diphenylethyl)-4-methyl-3-oxo-4-azaandrost-5-ene-17β-carboxamide.

84. The compound of claim 1, which is N-(1-methyl-1-phenylethyl)-3-oxo-4-azaandrost-5-ene-17β-carboxamide.

85. The compound of claim 1, which is N-(1-methyl-1-phenylethyl)-4-methyl-3-oxo-4-azaandrost-5-ene-17β-carboxamide.

86. The compound of claim 1, which is N-[1-methyl-1-(2-thienyl)ethyl]-3-oxo-4-aza-androst-5-ene-17β-carboxamide.

87. The compound of claim 1, which is N-[1-methyl-1-(2-thienyl)ethyl]-4-methyl-3-oxo-4-azaandrost-5-ene-17β-carboxamide.

88. The compound of claim 1, which is N-[α-(4-hydroxyphenyl)benzyl]-3-oxo-4-azaandrost-5-ene-17β-carboxamide.

89. The compound of claim 1, which is N-[α-(4-hydroxyphenyl)benzyl]-4-methyl-3-oxo-4-azaandrost-5-ene-17β-carboxamide.

90. The compound of claim 1, which is N-[1-(4-methoxyphenyl)-1-methylethyl]-3-oxo-4-azaandrost-5-ene-17β-carboxamide.

91. The compound of claim 1, which is N-[1-(4-methoxyphenyl)-1-methylethyl]-4-methyl-3-oxo-4-azaandrost-5-ene-17β-carboxamide.

92. The compound of claim 1, which is N-(2-hydroxy-1,2-diphenylethyl)-4-methyl-3-oxo-4-azaandrost-5-ene-17β-carboxamide.

93. The compound of claim 1, which is N,N-diphenyl-3-oxo-4-azaandrost-5-ene-17β-carbohydrazide.

94. The compound of claim 1, which is N,N-diphenyl-4-methyl-3-oxo-4-azaandrost-5-ene-17β-carbohydrazide.

95. The compound of claim 1, which is N-[1-(3-methoxyphenyl)-1-methylethyl]-3-oxo-4-azaandrost-5-ene-17β-carboxamide.

96. The compound of claim 1, which is N-[1-(2-methoxyphenyl)-1-methylethyl]-4-methyl-3-oxo-4-azaandrost-5-ene-17β-carboxamide.

97. A composition for the treatment or prophylaxis of prostatic hypertrophy, which comprises an effective amount of at least one active compound in admixture with a carrier or diluent, wherein the active compound is at least one compound of formula (I) or a pharmaceutically acceptable salt or ester thereof, as claimed in claim 1.

98. The composition of claim 97, wherein said active compound is selected from the group consisting of:
N-(1,2-diphenylethyl)-3-oxo-4-aza-5α-androstane-17β-carboxamide;
N-(diphenylmethyl)-3-oxo-4-aza-5α-androstane-17β-carboxamide;
N-(1,1-diphenylethyl)-3-oxo-4-aza-5α-androstane-17β-carboxamide;
N-(diphenylmethyl)-4-methyl-3-oxo-4-aza-5α-androstane-17β-carboxamide;
N-(1,2-diphenylethyl)-4-methyl-3-oxo-4-aza-5α-androstane-17β-carboxamide;
N-(1-methyl-1-phenylethyl)-3-oxo-4-aza-5α-androstane-17β-carboxamide;
N-[1-methyl-1-(2-thienyl)ethyl]-3-oxo-4-aza-5α-androstane-17β-carboxamide;
N-[1-methyl-1-(2-thienyl)ethyl]-4-methyl-3-oxo-4-aza-5α-androstane-17β-carboxamide;
N-(1-methyl-1-phenylethyl)-4-methyl-3-oxo-4-aza-5α-androstane-17β-carboxamide;
N-[2-(4-methylphenyl)-1-phenylethyl]-4-methyl-3-oxo-4-aza-5α-androstane-17β-carboxamide;
N-[2-(4-methylphenyl)-1-phenylethyl]-3-oxo-4-aza-5α-androstane-17β-carboxamide;
N-(1,1-diphenylethyl)-4-methyl-3-oxo-4-aza-5α-androstane-17β-carboxamide;
N-[α-(4-hydroxyphenyl)benzyl]-3-oxo-4-aza-5α-androstane-17β-carboxamide;
N-[α-(4-hydroxyphenyl)benzyl]-4-methyl-3-oxo-4-aza-5α-androstane-17β-carboxamide;
N-[1-(4-methoxyphenyl)-1-methylethyl]-3-oxo-4-aza-5α-androstane-17β-carboxamide;
N-[1-(4-methoxyphenyl)-1-methylethyl]-4-methyl-3-oxo-4-aza-5α-androstane-17β-carboxamide;
N,N-diphenyl-3-oxo-4-aza-5α-androstane-17β-carbohydrazide;
N,N-diphenyl-4-methyl-3-oxo-4-aza-5α-androstane-17β-carbohydrazide;
N-[1-(3-methoxyphenyl)-1-methylethyl]-4-methyl-3-oxo-4-aza-5α-androstane-17β-carboxamide;
N-[1-methyl-1-(2-furyl)ethyl]-3-oxo-4-aza-5α-androstane-17β-carboxamide;
N-(1,2-diphenylethyl)-3-oxo-4-aza-5α-androst-1-ene-17β-carboxamide;
N-(1,2-diphenylethyl)-4-methyl-3-oxo-4-aza-5α-androst-1-ene-17β-carboxamide;
N-(diphenylmethyl)-3-oxo-4-aza-5α-androst-1-ene-17β-carboxamide;
N-(diphenylmethyl)-4-methyl-3-oxo-4-aza-5α-androst-1-ene-17β-carboxamide;
N-[1-phenyl-2-(4-methylphenyl)ethyl]-3-oxo-4-aza-5α-androst-1-ene-17β-carboxamide;
N-[1-phenyl-2-(4-methylphenyl)ethyl]-4-methyl-3-oxo-4-aza-5α-androst-1-ene-17β-carboxamide;
N-(1,1-diphenylethyl)-3-oxo-4-aza-5α-androst-1-ene-17β-carboxamide;
N-(1,1-diphenylethyl)-4-methyl-3-oxo-4-aza-5α-androst-1-ene-17β-carboxamide;
N-(1-methyl-1-phenylethyl)-3-oxo-4-aza-5α-androst-1-ene-17β-carboxamide;
N-(1-methyl-1-phenylethyl)-4-methyl-3-oxo-4-aza-5α-androst-1-ene-17β-carboxamide;
N-[1-methyl-1-(2-thienyl)ethyl]-3-oxo-4-aza-5α-androst-1-ene-17β-carboxamide;
N-[1-methyl-1-(2-thienyl)ethyl]-4-methyl-3-oxo-4-aza-5α-androst-1-ene-17β-carboxamide;
N-[α-(4-hydroxyphenyl)benzyl]-3-oxo-4-aza-5α-androst-1-ene-17β-carboxamide;
N-[α-(4-hydroxyphenyl)benzyl]-4-methyl-3-oxo-4-aza-5α-androst-1-ene-17β-carboxamide;
N-[1-(4-methoxyphenyl)-1-methylethyl]-3-oxo-4-aza-5α-androst-1-ene-17β-carboxamide;
N-[1-(4-methoxyphenyl)-1-methylethyl]-4-methyl-3-oxo-4-aza-5α-androst-1-ene-17β-carboxamide;
N-(2-hydroxy-1,2-diphenylethyl)-3-oxo-4-aza-5α-androst-1-ene-17β-carboxamide;

N,N-diphenyl-3-oxo-4-aza-5α-androst-1-ene-17β-carbohydrazide;
N,N-diphenyl-4-methyl-3-oxo-4-aza-5α-androst-1-ene-17β-carbohydrazide;
N-[1-(2-methoxyphenyl)-1-methylethyl]-3-oxo-4-aza-5α-androst-1-ene-17β-carboxamide;
N-[1-methyl-1-(2-furyl)ethyl]-3-oxo-4-aza-5α-androst-1-ene-17β-carboxamide;
N-(1,2-diphenylethyl)-3-oxo-4-azaandrost-5-ene-17β-carboxamide;
N-(1,2-diphenylethyl)-4-methyl-3-oxo-4-azaandrost-5-ene-17β-carboxamide;
N-(diphenylmethyl)-3-oxo-4-azaandrost-5-ene-17β-carboxamide;
N-(diphenylmethyl)-4-methyl-3-oxo-4-azaandrost-5-ene-17β-carboxamide;
N-[2-(4-methylphenyl)-1-phenylethyl]-3-oxo-4-azaandrost-5-ene-17β-carboxamide;
N-[2-(4-methylphenyl)-1-phenylethyl]-4-methyl-3-oxo-4-azaandrost-5-ene-17β-carboxamide;
N-(1,1-diphenylethyl)-3-oxo-4-azaandrost-5-ene-17β-carboxamide;
N-(1,1-diphenylethyl)-4-methyl-3-oxo-4-azaandrost-5-ene-17β-carboxamide;
N-(1-methyl-1-phenylethyl)-3-oxo-4-azaandrost-5-ene-17β-carboxamide;
N-(1-methyl-1-phenylethyl)-4-methyl-3-oxo-4-azaandrost-5-ene-17β-carboxamide;
N-[1-methyl-1-(2-thienyl)ethyl]-3-oxo-4-azaandrost-5-ene-17β-carboxamide;
N-[1-methyl-1-(2-thienyl)ethyl]-4-methyl-3-oxo-4-azaandrost-5-ene-17β-carboxamide;
N-[α-(4-hydroxyphenyl)benzyl]-3-oxo-4-azaandrost-5-ene-17β-carboxamide;
N-[α-(4-hydroxyphenyl)benzyl]-4-methyl-3-oxo-4-azaandrost-5-ene-17β-carboxamide;
N-[1-(4-methoxyphenyl)-1-methylethyl]-3-oxo-4-azaandrost-5-ene-17β-carboxamide;
N-[1-(4-methoxyphenyl)-1-methylethyl]-4-methyl-3-oxo-4-azaandrost-5-ene-17β-carboxamide;
N-(2-hydroxy-1,2-diphenylethyl)-4-methyl-3-oxo-4-azaandrost-5-ene-17β-carboxamide;
N,N-diphenyl-3-oxo-4-azaandrost-5-ene-17β-carbohydrazide;
N,N-diphenyl-4-methyl-3-oxo-4-azaandrost-5-ene-17β-carbohydrazide;
N-[1-(3-methoxyphenyl)-1-methylethyl]-3-oxo-4-azaandrost-5-ene-17β-carboxamide;
N-[1-(2-methoxyphenyl)-1-methylethyl]-4-methyl-3-oxo-4-azaandrost-5-ene-17β-carboxamide; and
N-[1-methyl-1-(2-furyl)ethyl]-4-methyl-3-oxo-4-azaandrost-5-ene-17β-carboxamide.

99. The method of claim 20, wherein said active compound is selected from the group consisting of:
N-(1,2-diphenylethyl)-3-oxo-4-aza-5α-androstane-17β-carboxamide;
N-(diphenylmethyl)-3-oxo-4-aza-5α-androstane-17β-carboxamide;
N-(1,1-diphenylethyl)-3-oxo-4-aza-5α-androstane-17β-carboxamide;
N-(diphenylmethyl)-4-methyl-3-oxo-4-aza-5α-androstane-17β-carboxamide;
N-(1,2-diphenylethyl)-4-methyl-3-oxo-4-aza-5α-androstane-17β-carboxamide;
N-(1-methyl-1-phenylethyl)-3-oxo-4-aza-5α-androstane-17β-carboxamide;
N-[1-methyl-1-(2-thienyl)ethyl]-3-oxo-4-aza-5α-androstane-17β-carboxamide;
N-[1-methyl-1-(2-thienyl)ethyl]-4-methyl-3-oxo-4-aza-5α-androstane-17β-carboxamide;
N-(1-methyl-1-phenylethyl)-4-methyl-3-oxo-4-aza-5α-androstane-17β-carboxamide;
N-[2-(4-methylphenyl)-1-phenylethyl]-4-methyl-3-oxo-4-aza-5α-androstane-17β-carboxamide;
N-[2-(4-methylphenyl)-1-phenylethyl]-3-oxo-4-aza-5α-androstane-17β-carboxamide;
N-(1,1-diphenylethyl)-4-methyl-3-oxo-4-aza-5α-androstane-17β-carboxamide;
N-[α-(4-hydroxyphenyl)benzyl]-3-oxo-4-aza-5α-androstane-17β-carboxamide;
N-[α-(4-hydroxyphenyl)benzyl]-4-methyl-3-oxo-4-aza-5α-androstane-17β-carboxamide;
N-[1-(4-methoxyphenyl)-1-methylethyl]-3-oxo-4-aza-5α-androstane-17β-carboxamide;
N-[1-(4-methoxyphenyl)-1-methylethyl]-4-methyl-3-oxo-4-aza-5α-androstane-17β-carboxamide;
N,N-diphenyl-3-oxo-4-aza-5α-androstane-17β-carbohydrazide;
N,N-diphenyl-4-methyl-3-oxo-4-aza-5α-androstane-17β-carbohydrazide;
N-[1-(3-methoxyphenyl)-1-methylethyl]-4-methyl-3-oxo-4-aza-5α-androstane-17β-carboxamide;
N-[1-methyl-1-(2-furyl)ethyl]-3-oxo-4-aza-5α-androstane-17β-carboxamide;
N-(1,2-diphenylethyl)-3-oxo-4-aza-5α-androst-1-ene-17β-carboxamide;
N-(1,2-diphenylethyl)-4-methyl-3-oxo-4-aza-5α-androst-1-ene-17β-carboxamide;
N-(diphenylmethyl)-3-oxo-4-aza-5α-androst-1-ene-17β-carboxamide;
N-(diphenylmethyl)-4-methyl-3-oxo-4-aza-5α-androst-1-ene-17β-carboxamide;
N-[1-phenyl-2-(4-methylphenyl)ethyl]-3oxo-4-aza-5α-androst-1-ene-17β-carboxamide;
N-[1-phenyl-2-(4-methylphenyl)ethyl]-4-methyl-3-oxo-4-aza-5α-androst-1-ene-17β-carboxamide;
N-(1,1-diphenylethyl)-3-oxo-4-aza-5α-androst-1-ene-17β-carboxamide;
N-(1,1-diphenylethyl)-4-methyl-3-oxo-4-aza-5α-androst-1-ene-17β-carboxamide;
N-(1-methyl-1-phenylethyl)-3-oxo-4-aza-5α-androst-1-ene-17β-carboxamide;
N-(1-methyl-1-phenylethyl)-4-methyl-3-oxo-4-aza-5α-androst-1-ene-17β-carboxamide;
N-[1-methyl-1-(2-thienyl)ethyl]-3-oxo-4-aza-5α-androst-1-ene-17β-carboxamide;
N-[1-methyl-1-(2-thienyl)ethyl]-4-methyl-3-oxo-4-aza-5α-androst-1-ene-17β-carboxamide;
N-[α-(4-hydroxyphenyl)benzyl]-3-oxo-4-aza-5α-androst-1-ene-17β-carboxamide;
N-[α-(4-hydroxyphenyl)benzyl]-4-methyl-3-oxo-4-aza-5α-androst-1-ene-17β-carboxamide;
N-[1-(4-methoxyphenyl)-1-methylethyl]-3-oxo-4-aza-5α-androst-1-ene-17β-carboxamide;
N-[1-(4-methoxyphenyl)-1-methylethyl]-4-methyl-3-oxo-4-aza-5α-androst-1-ene-17β-carboxamide;
N-(2-hydroxy-1,2-diphenylethyl)-3-oxo-4-aza-5α-androst-1-ene-17β-carboxamide;
N,N-diphenyl-3-oxo-4-aza-5α-androst-1-ene-17β-carbohydrazide;
N,N-diphenyl-4-methyl-3-oxo-4-aza-5α-androst-1-ene-17β-carbohydrazide;
N-[1-(2-methoxyphenyl)-1-methylethyl]-3-oxo-4-aza-5α-androst-1-ene-17β-carboxamide;
N-[1-methyl-1-(2-furyl)ethyl]-3-oxo-4-aza-5α-androst-1-ene-17β-carboxamide;

N-(1,2-diphenylethyl)-3-oxo-4-azaandrost-5-ene-17β-carboxamide;
N-(1,2-diphenylethyl)-4-methyl-3-oxo-4-azaandrost-5-ene-17β-carboxamide;
N-(diphenylmethyl)-3-oxo-4-azaandrost-5-ene-17β-carboxamide;
N-(diphenylmethyl)-4-methyl-3-oxo-4-azaandrost-5-ene-17β-carboxamide;
N-[2-(4-methylphenyl)-1-phenylethyl]-3-oxo-4-azaandrost-5-ene-17β-carboxamide;
N-[2-(4-methylphenyl)-1-phenylethyl]-4-methyl-3-oxo-4-azaandrost-5-ene-17β-carboxamide;
N-(1,1-diphenylethyl)-3-oxo-4-azaandrost-5-ene-17β-carboxamide;
N-(1,1-diphenylethyl)-4-methyl-3-oxo-4-azaandrost-5-ene-17β-carboxamide;
N-(1-methyl-1-phenyethyl)-3-oxo-4-azaandrost-5-ene-17β-carboxamide;
N-(1-methyl-1-phenylethyl)-4-methyl-3-oxo-4-azaandrost-5-ene-17β-carboxamide;
N-[1-methyl-1-(2-thienyl)ethyl]-3-oxo-4-azaandrost-5-ene-17β-carboxamide;
N-[1-methyl-1-(2-thienyl)ethyl]-4-methyl-3-oxo-4-azaandrost-5-ene-17β-carboxamide;
N-[α-(4-hydroxyphenyl)benzyl]-3-oxo-4-azaandrost-5-ene-17β-carboxamide;
N-[α-(4-hydroxyphenyl)benzyl]-4-methyl-3-oxo-4-azaandrost-5-ene-17β-carboxamide;
N-[1-(4-methoxyphenyl)-1-methylethyl]-3-oxo-4-azaandrost-5-ene-17β-carboxamide;
N-[1-(4-methoxyphenyl)-1-methylethyl]-4-methyl-3-oxo-4-azaandrost-5-ene-17β-carboxamide;
N-(2-hydroxy-1,2-diphenylethyl)-4-methyl-3-oxo-4-azaandrost-5-ene-17β-carboxamide;
N,N-diphenyl-3-oxo-4-azaandrost-5-ene-17β-carbohydrazide;
N,N-diphenyl-4-methyl-3-oxo-4-azaandrost-5-ene-17β-carbohydrazide;
N-[1-(3-methoxyphenyl)-1-methylethyl]-3-oxo-4-azaandrost-5-ene-17β-carboxamide;
N-[1-(2-methoxyphenyl)-1-methylethyl]-4-methyl-3-oxo-4-azaandrost-5-ene-17β-carboxamide; and
N-[1-methyl-1-(2-furyl)ethyl]-4-methyl-3-oxo-4-azaandrost-5-ene-17β-carboxamide.

100. A method of inhibiting testosterone 5α-reductase in a patient in need of such inhibition, said method comprising administering to said patient an effective testosterone 5α-reductase inhibiting amount of at least one compound of formula (I) or a pharmaceutically acceptable salt or ester thereof, as claimed in claim 1.

101. The method of claim 100, wherein said compound is selected from the group consisting of:
N-(1,2-diphenylethyl)-3-oxo-4-aza-5α-androstane-17β-carboxamide;
N-(diphenylmethyl)-3-oxo-4-aza-5α-androstane-17β-carboxamide;
N-(1,1-diphenylethyl)-3-oxo-4-aza-5α-androstane-17β-carboxamide;
N-(diphenylmethyl)-4-methyl-3-oxo-4-aza-5α-androstane-17β-carboxamide;
N-(1,2-diphenylethyl)-4-methyl-3-oxo-4-aza-5α-androstane-17β-carboxamide;
N-(1-methyl-1-phenylethyl)-3-oxo-4-aza-5α-androstane-17β-carboxamide;
N-[1-methyl-1-(2-thienyl)ethyl]-3-oxo-4-aza-5α-androstane-17β-carboxamide;
N-[1-methyl-1-(2-thienyl)ethyl]-4-methyl-3-oxo-4-aza-5α-androstane-17β-carboxamide;
N-(1-methyl-1-phenylethyl)-4-methyl-3-oxo-4-aza-5α-androstane-17β-carboxamide;
N-[2-(4-methylphenyl)-1-phenylethyl]-4-methyl-3-oxo-4-aza-5α-androstane-17β-carboxamide;
N-[2-(4-methylphenyl)-1-phenylethyl]-3-oxo-4-aza-5α-androstane-17β-carboxamide;
N-(1,1-diphenylethyl)-4-methyl-3-oxo-4-aza-5α-androstane-17β-carboxamide;
N-[α-(4-hydroxyphenyl)benzyl]-3-oxo-4-aza-5α-androstane-17β-carboxamide;
N-[α-(4-hydroxyphenyl)benzyl]-4-methyl-3-oxo-4-aza-5α-androstane-17β-carboxamide;
N-[1-(4-methoxyphenyl)-1-methylethyl]-3-oxo-4-aza-5α-androstane-17β-carboxamide;
N-[1-(4-methoxyphenyl)-1-methylethyl]-4-methyl-3-oxo-4-aza-5α-androstane 17β-carboxamide;
N,N-diphenyl-3-oxo-4-aza-5α-androstane-17β-carbohydrazide;
N,N-diphenyl-4-methyl-3-oxo-4-aza-5α-androstane-17β-carbohydrazide;
N-[1-(3-methoxyphenyl)-1-methylethyl]-4-methyl-3-oxo-4-aza-5α-androstane-17β-carboxamide;
N-[1-methyl-1-(2-furyl)ethyl]-3-oxo-4-aza-5α-androstane-17β-carboxamide;
N-(1,2-diphenylethyl)-3-oxo-4-aza-5α-androst-1-ene-17β-carboxamide;
N-(1,2-diphenylethyl)-4-methyl-3-oxo-4-aza-5α-androst-1-ene-17β-carboxamide;
N-(diphenylmethyl)-3-oxo-4-aza-5α-androst-1-ene-17β-carboxamide;
N-(diphenylmethyl)-4-methyl-3-oxo-4-aza-5α-androst-1-ene-17β-carboxamide;
N-[1-phenyl-2-(4-methylphenyl)ethyl]-3-oxo-4-aza-5α-androst-1-ene-17β-carboxamide;
N-[1-phenyl-2-(4-methylphenyl)ethyl]-4-methyl-3-oxo-4-aza-5α-androst-1-ene-17β-carboxamide;
N-(1,1-diphenylethyl)-3-oxo-4-aza-5α-androst-1-ene-17β-carboxamide;
N-(1,1-diphenylethyl)-4-methyl-3-oxo-4-aza-5α-androst-1-ene-17β-carboxamide;
N-(1-methyl-1-phenylethyl)-3-oxo-4-aza-5α-androst-1-ene-17β-carboxamide;
N-(1-methyl-1-phenylethyl)-4-methyl-3-oxo-4-aza-5α-androst-1-ene-17β-carboxamide;
N-[1-methyl-1-(2-thienyl)ethyl]-3-oxo-4-aza-5α-androst-1-ene-17β-carboxamide;
N-[1-methyl-1-(2-thienyl)ethyl]-4-methyl-3-oxo-4-aza-5α-androst-1-ene-17β-carboxamide;
N-[α-(4-hydroxyphenyl)benzyl]-3-oxo-4-aza-5α-androst-1-ene-17β-carboxamide;
N-[α-(4-hydroxyphenyl)benzyl]-4-methyl-3-oxo-4-aza-5α-androst-1-ene-17β-carboxamide;
N-[1-(4-methoxyphenyl)-1-methylethyl]-3-oxo-4-aza-5α-androst-1-ene-17β-carboxamide;
N-[1-(4-methoxyphenyl)-1-methylethyl]-4-methyl-3-oxo-4-aza-5α-androst-1-ene-17β-carboxamide;
N-(2-hydroxy-1,2-diphenylethyl)-3-oxo-4-aza-5α-androst-1-ene-17β-carboxamide;
N,N-diphenyl-3-oxo-4-aza-5α-androst-1-ene-17β-carbohydrazide;
N,N-diphenyl-4-methyl-3-oxo-4-aza-5α-androst-1-ene-17β-carbohydrazide;
N-[1-(2-methoxyphenyl)-1-methylethyl]-3-oxo-4-aza-5α-androst-1-ene-17β-carboxamide;
N-[1-methyl-1-(2-furyl)ethyl]-3-oxo-4-aza-5α-androst-1-ene-17β-carboxamide;
N-(1,2-diphenylethyl)-3-oxo-4-azaandrost-5-ene-17β-carboxamide;

N-(1,2-diphenylethyl)-4-methyl-3-oxo-4-azaandrost-5-ene-17β-carboxamide;
N-(diphenylmethyl)-3-oxo-4-azaandrost-5-ene-17β-carboxamide;
N-(diphenylmethyl)-4-methyl-3-oxo-4-azaandrost-5-ene-17β-carboxamide;
N-[2-(4-methylphenyl)-1-phenylethyl]-3-oxo-4-azaandrost-5-ene-17β-carboxamide;
N-[2-(4-methylphenyl)-1-phenylethyl]-4-methyl-3-oxo-4-azaandrost-5-ene-17β-carboxamide;
N-(1,1-diphenylethyl)-3-oxo-4-azaandrost-5-ene-17β-carboxamide;
N-(1,1-diphenylethyl)-4-methyl-3-oxo-4-azaandrost-5-ene-17β-carboxamide;
N-(1-methyl-1-phenylethyl)-3-oxo-4-azaandrost-5-ene-17β-carboxamide;
N-(1-methyl-1-phenylethyl)-4-methyl-3-oxo-4-azaandrost-5-ene-17β-carboxamide;
N-[1-methyl-1-(2-thienyl)ethyl]-3-oxo-4-azaandrost-5-ene-17β-carboxamide;
N-[1-methyl-1-(2-thienyl)ethyl]-4-methyl-3-oxo-4-azaandrost-5-ene-17β-carboxamide;
N-[α-(4-hydroxyphenyl)benzyl]-3-oxo-4-azaandrost-5-ene-17β-carboxamide;
N-[α-(4-hydroxyphenyl)benzyl]-4-methyl-3-oxo-4-azaandrost-5-ene-17β-carboxamide;
N-[1-(4-methoxyphenyl)-1-methylethyl]-3-oxo-4azaandrost-5-ene-17β-carboxamide;
N-[1-(4-methoxyphenyl)-1-methylethyl]-4-methyl-3-oxo-4-azaandrost-5-ene-17β-carboxamide;
N-(2-hydroxy-1,2-diphenylethyl)-4-methyl-3-oxo-4-azaandrost-5-ene-17β-carboxamide;
N,N-diphenyl-3-oxo-4-azaandrost-5-ene-17β-carbohydrazide;
N,N-diphenyl-4-methyl-3-oxo-4-azaandrost-5-ene-17β-carbohydrazide;
N-[1-(3-methoxyphenyl)-1-methylethyl]-3-oxo-4-azaandrost-5-ene-17β-carboxamide;
N-[1-(2-methoxyphenyl)-1-methylethyl]-4-methyl-3-oxo-4-azaandrost-5-ene-17β-carboxamide; and
N-[1-methyl-1-(2-furyl)ethyl]-4-methyl-3-oxo-4-azaandrost-5-ene-17β-carboxamide.

* * * * *